United States Patent
Shelton

(10) Patent No.: US 8,056,358 B1
(45) Date of Patent: Nov. 15, 2011

(54) METHOD AND APPARATUS FOR DISINFECTING A REFRIGERATED WATER COOLER RESERVOIR

(75) Inventor: James J. Shelton, Pontchatoula, LA (US)

(73) Assignee: S.I.P. Technologies L.L.C., New Orleans, LA (US)

( * ) Notice: Subject to any disclaimer, the term of this patent is extended or adjusted under 35 U.S.C. 154(b) by 152 days.

(21) Appl. No.: 12/652,421

(22) Filed: Jan. 5, 2010

Related U.S. Application Data

(63) Continuation of application No. 10/463,870, filed on Jun. 17, 2003, now Pat. No. 7,640,766, which is a continuation-in-part of application No. 10/173,133, filed on Jun. 17, 2002, now abandoned, and a continuation-in-part of application No. PCT/US02/19158, filed on Jun. 17, 2002.

(60) Provisional application No. 60/389,439, filed on Jun. 18, 2002.

(51) Int. Cl.
*F25D 3/00* (2006.01)
*B67D 7/76* (2010.01)

(52) U.S. Cl. .................. 62/392; 62/289; 222/190

(58) Field of Classification Search .................. 62/318, 62/389, 392; 222/185.1, 146.6, 190
See application file for complete search history.

(56) References Cited

U.S. PATENT DOCUMENTS

| | | |
|---|---|---|
| 1,403,025 A | 1/1922 | Haase |
| 2,093,619 A | 9/1937 | Powell |
| 2,947,525 A | 8/1960 | Klein |
| 3,448,045 A | 6/1969 | Hess et al. |
| 3,692,180 A | 9/1972 | LaRaus |
| 3,726,404 A | 4/1973 | Troglione |
| 3,967,131 A | 6/1976 | Slipiec et al. |
| 3,970,731 A | 7/1976 | Oksman |
| 4,019,986 A | 4/1977 | Burris et al. |
| 4,035,657 A | 7/1977 | Carlson |
| 4,410,495 A | 10/1983 | Bassler et al. |
| 4,764,349 A | 8/1988 | Arff et al. |
| 4,776,127 A | 10/1988 | Jackson |
| 4,805,808 A | 2/1989 | Larson |
| 4,842,723 A | 6/1989 | Parks et al. |
| 5,015,394 A | 5/1991 | McEllhenney et al. |
| 5,106,495 A | 4/1992 | Hughes |
| 5,256,282 A | 10/1993 | Chang et al. |
| 5,295,519 A | 3/1994 | Baker et al. |
| 5,328,059 A | 7/1994 | Campbell |
| 5,366,619 A | 11/1994 | Matsui et al. |
| 5,431,861 A | 7/1995 | Nagahiro et al. |

(Continued)

FOREIGN PATENT DOCUMENTS

EP 0163750 12/1985

(Continued)

*Primary Examiner* — Chen Wen Jiang
(74) *Attorney, Agent, or Firm* — Garvey, Smith, Nehrbass & North, L.L.C.; Charles C. Garvey, Jr.

(57) ABSTRACT

A method and apparatus for providing sanitized water in a cabinet and spigot type bottled water dispenser features an ozone generating system to generate ozone for sanitizing the water. Ozone is generated and collected within an ozone generator housing. A blower transmits air to the ozone generator housing. The air carries the ozone that is generated through a flow line to an air diffuser that is positioned upstream of the spigot (or spigots) used to dispense water. In one embodiment, a valve that is activated on the spigot to dispense water also activates the blower and ozone generator. In other embodiments, a flow sensor activates the ozone generator and blower. Various spigot and flow sensor arrangements are disclosed as a part of the overall apparatus and method.

26 Claims, 31 Drawing Sheets

U.S. PATENT DOCUMENTS

| | | |
|---|---|---|
| 5,503,809 A | 4/1996 | Coate et al. |
| 5,531,908 A | 7/1996 | Matsumoto et al. |
| 5,567,322 A | 10/1996 | Rundle et al. |
| 5,567,332 A | 10/1996 | Mehta |
| 5,582,717 A | 12/1996 | Di Santo |
| 5,587,089 A | 12/1996 | Vogel et al. |
| 5,632,268 A | 5/1997 | Ellis et al. |
| 5,669,221 A | 9/1997 | LeBleu et al. |
| 5,698,164 A | 12/1997 | Kishioka et al. |
| 5,871,701 A | 2/1999 | Long |
| 6,085,540 A | 7/2000 | Davis |
| 6,149,804 A | 11/2000 | Chung et al. |
| 6,270,733 B1 | 8/2001 | Rodden |
| 6,289,690 B1 | 9/2001 | Davis |
| 6,361,686 B1 | 3/2002 | Conrad |
| 6,405,387 B1 | 6/2002 | Barnes |
| 6,532,760 B2 | 3/2003 | Davis |
| 6,568,900 B2 | 5/2003 | Conrad et al. |
| 7,640,766 B2 | 1/2010 | Shelton |
| 2002/0041041 A1 | 4/2002 | Johnson |

FOREIGN PATENT DOCUMENTS

| | | |
|---|---|---|
| EP | 739312 | 10/1996 |
| GB | 2022979 | 12/1979 |
| JP | 61103595 | 5/1986 |
| WO | WO 88/04279 | 6/1988 |
| WO | WO 92/04969 | 4/1992 |
| WO | WO 93/17725 | 9/1993 |
| WO | WO 97/42924 | 11/1997 |
| WO | WO 00/38815 | 7/2000 |

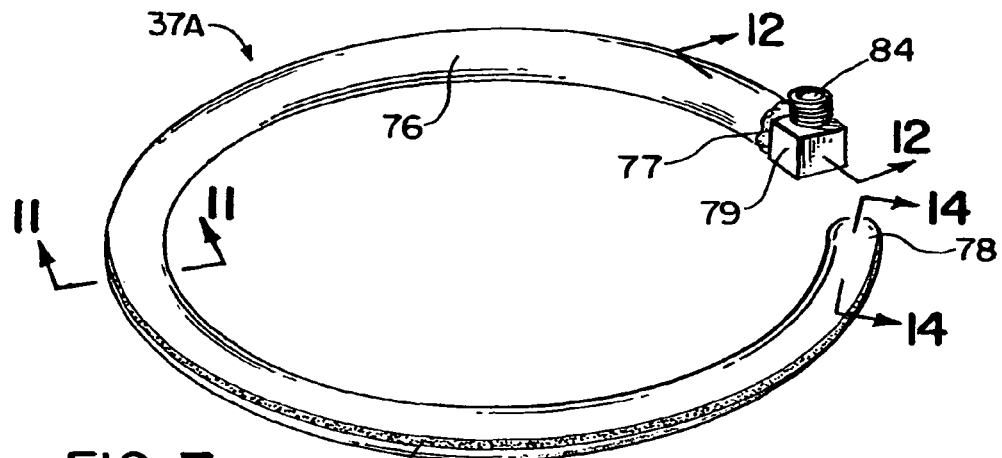
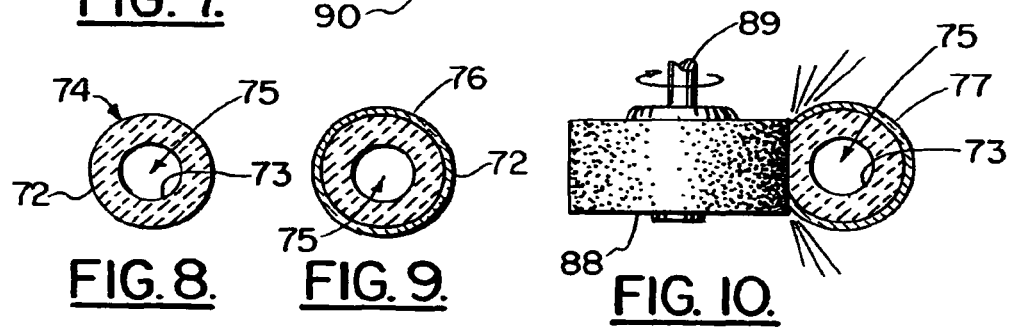
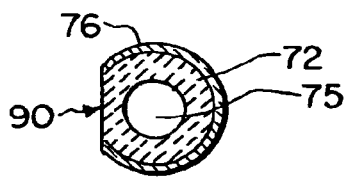
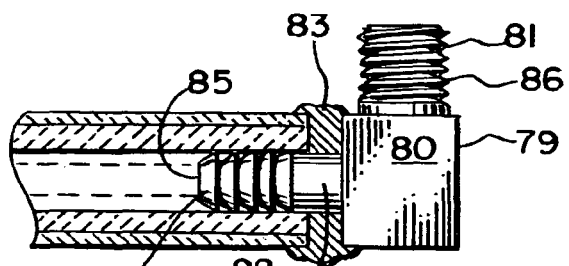
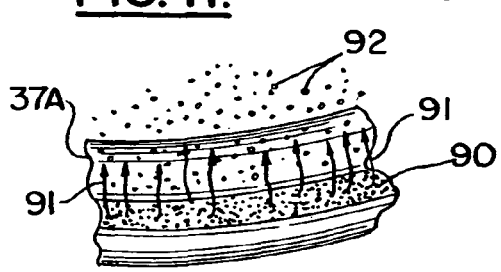
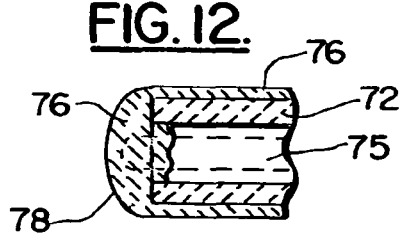

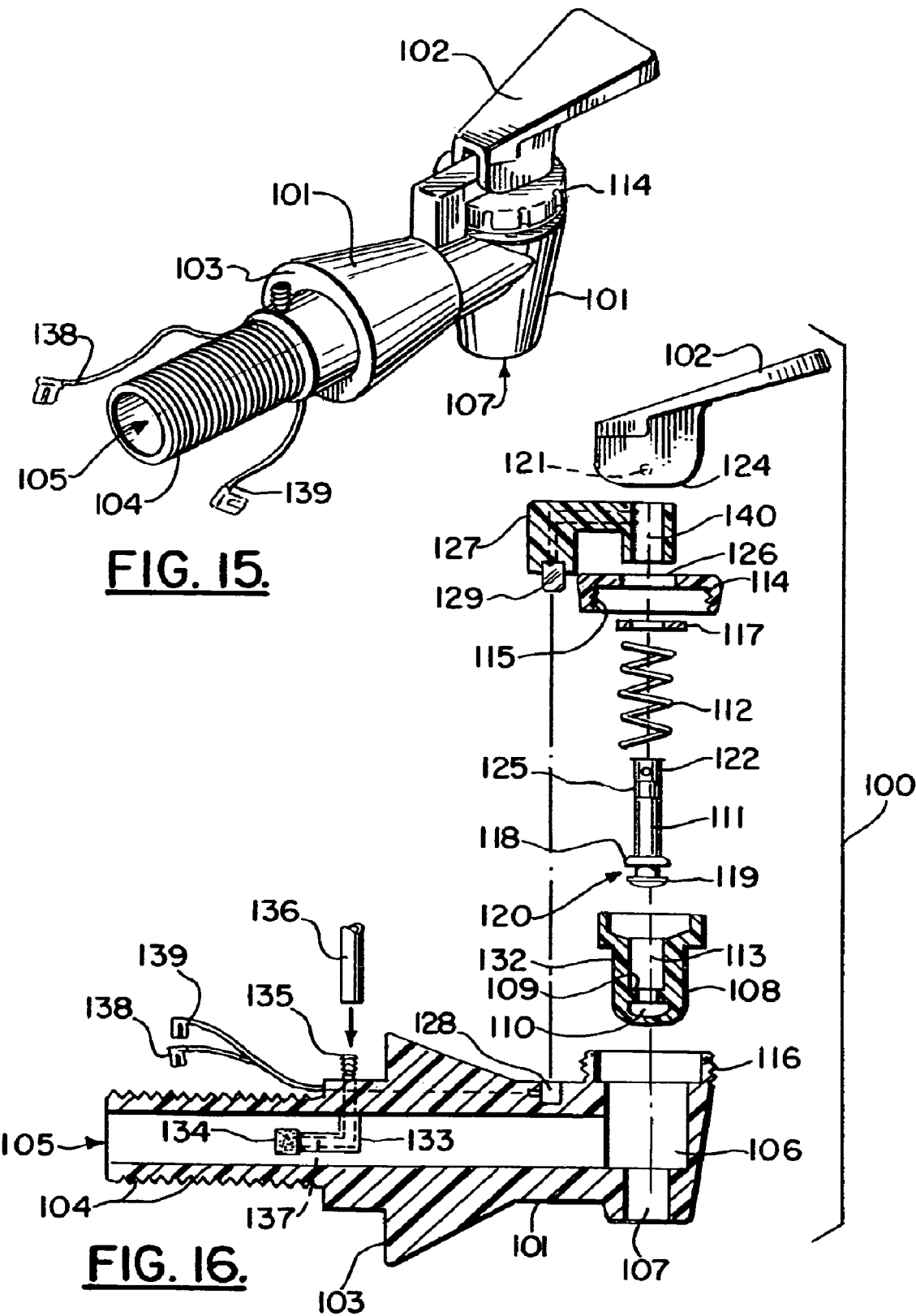

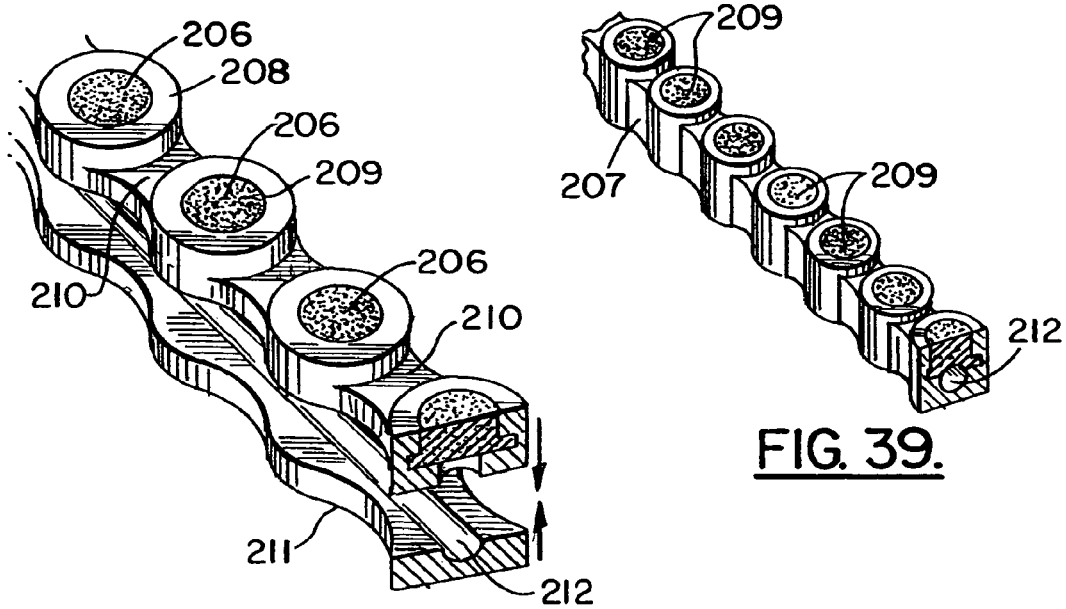
FIG. 38.
FIG. 39.
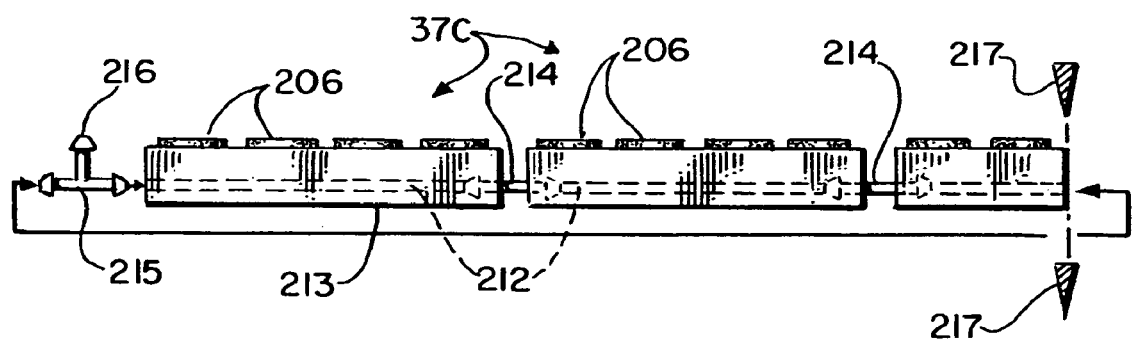
FIG. 40.

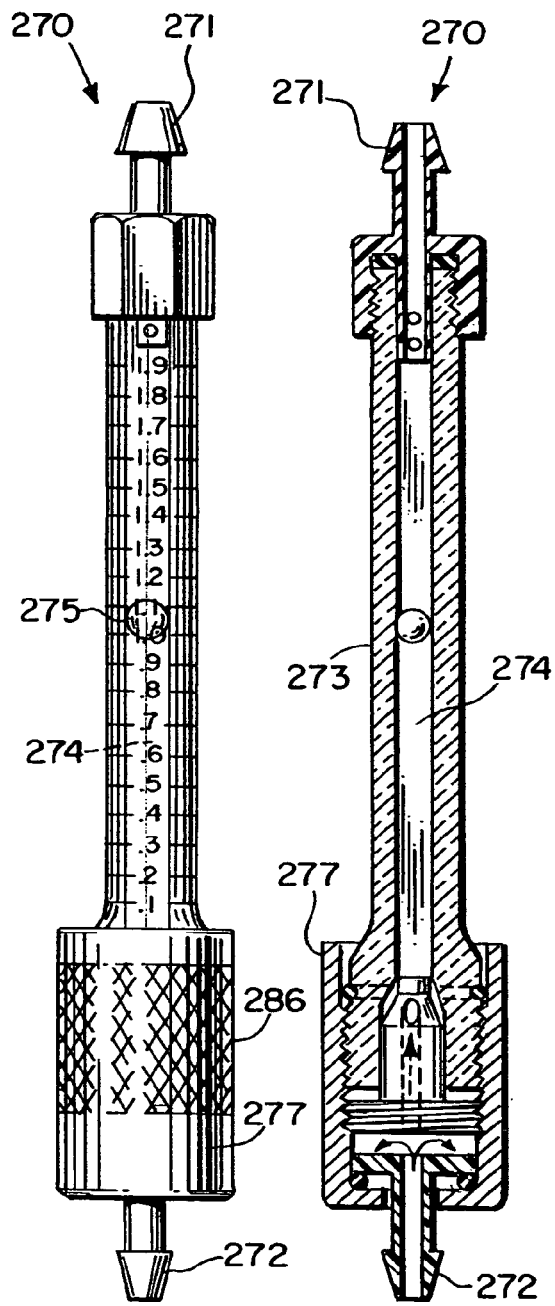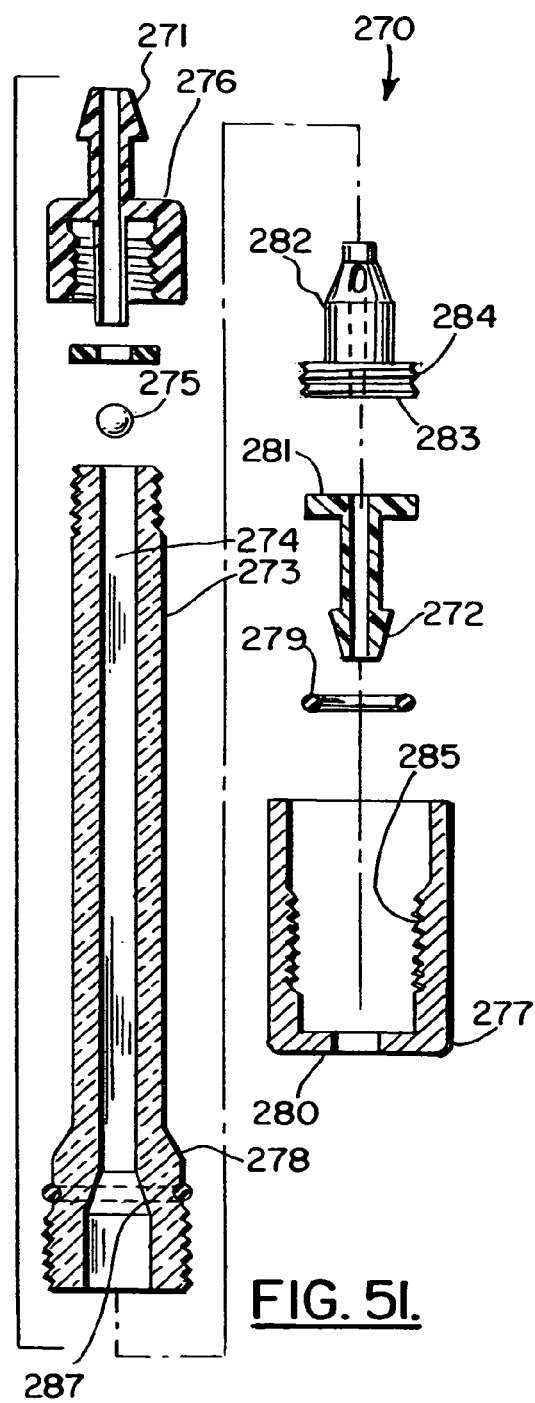
FIG. 49.  FIG. 50.  FIG. 51.

METHOD AND APPARATUS FOR DISINFECTING A REFRIGERATED WATER COOLER RESERVOIR

CROSS-REFERENCE TO RELATED APPLICATIONS

This is a continuation application of U.S. patent application Ser. No. 10/463,870, filed Jun. 17, 2003 (now U.S. Pat. No. 7,640,766), which claimed priority to U.S. Provisional patent application No. 60/389,439, filed 17 Jun. 2002, is a continuation-in-part of U.S. patent application Ser. No. 10/173,133, filed 17 Jun. 2002, and of International Patent Application No. PCT/US02/19158, also filed 17 Jun. 2002. Priority of each of these applications is hereby claimed and incorporated herein by reference.

Hereby incorporated herein by reference are U.S. patent application Ser. No. 09/996,328, filed 28 Nov. 2001; U.S. patent application Ser. No. 09/881,796 filed 15 Jun. 2001; U.S. patent application Ser. No. 09/954,849, filed 18 Sep. 2001; U.S. patent application Ser. No. 09/472,320, filed 23 Dec. 1999; and U.S. patent application Ser. No. 09/220,554, filed 23 Dec. 1998.

STATEMENT REGARDING FEDERALLY SPONSORED RESEARCH OR DEVELOPMENT

Not applicable

REFERENCE TO A "MICROFICHE APPENDIX"

There is no microfiche appendix, but see the text and drawings labeled as "Appendix A" attached to U.S. Provisional Patent Application No. 60/389,439, filed 17 Jun. 2002, hereby incorporated herein by reference.

BACKGROUND OF THE INVENTION

1. Field of the Invention

The present invention relates to bottled water (preferably refrigerated) dispensers, and more particularly to an improved bottled water dispenser for dispensing water that has been sanitized using ozone and more particularly to an improved method and apparatus for sanitizing water that is to be dispensed from a water cooler of the type having a cabinet with one or more spigots that are manually operable to dispense water from a reservoir water supply that is hidden inside the cabinet, and wherein air diffusers of improved configuration are disclosed that can be used to diffuse air into the reservoir.

2. General Background of the Invention

There are several types of cabinet type water dispensers in use today. One of the most common types of such water dispensers is a floor standing cabinet having an open top that receives a large inverted bottle. The bottle is typically of a plastic or glass material having a constricted neck. The bottle is turned upside down and placed on the top of the cabinet with the neck of the bottle extending into a water filled reservoir so that the water seeks its own level in the reservoir during use. As a user draws water from a spigot dispenser, the liquid level in the reservoir drops until it falls below the neck of the bottle at which time water flows from the bottle and bubbles enter the bottle until pressure has equalized. Inverted bottle type water dispensers are sold by a number of companies in the United States and elsewhere. Many are refrigerated.

Other types of water dispensers have an outer cabinet that contains a reservoir or water supply. These other types of water dispensers having a cabinet include one type that stores a large bottle (such as three or five gallon) at the bottom of the cabinet. A pump transfers water from the large bottle to the reservoir. At the reservoir, the water is typically refrigerated.

Another type of water dispenser simply connects a water supply (eg. city water, well water) directly to a reservoir that is hidden inside the cabinet. A float valve or other water level controller can be provided to insure that the reservoir is always filled with water but does not overflow. Water that is transferred from city water, well water or another source can be filtered or otherwise treated before being transmitted to the reservoir.

All of these types of water dispensers that employ cabinets typically have one or more water dispensing spigots on the outside of the cabinet. These spigots are typically manually operated, but can be automatically operated. For example, water vending machines dispense after a consumer pays for water. The water is automatically dispensed when coins are fed to the machine.

One of the problems with cabinet style water dispensers is that of cleansing the reservoir from time to time. Because the reservoir is not air tight, it breathes so that bacteria can easily enter the reservoir over a period of time. The reservoirs are typically contained within the confines of the cabinet and are not easily accessed and cleaned by consumers or end users.

For inverted bottle type dispensers, in addition to the problem of an open top, the five gallon bottles are themselves a source of bacteria and germs. Most of these bottles are transported on trucks where the bottles are exposed to outside air. They are handled by operators that typically grab the bottle at the neck, the very part of the bottle that communicates with the open reservoir during use. Unfortunately, it is difficult to convince every person that handles these bottles to wash their hands frequently enough.

In order to properly sanitize such a water dispenser or cooler, the user must carefully clean the neck of the bottle prior to combining the bottle with the cabinet. Further, the user should drain and sanitize the reservoir from time to time. The cleansing of the reservoir in such a water dispenser is a time consuming project that is typically not performed at regular intervals.

The dispensing spigots that are provided on common cabinet type water dispensers can also be a source of contamination. These spigots are typically manually operated and are therefore a source of contamination from the users that operate them. Very small children have also been known to drink directly from the spigot, probably because the spigot is located at a distance above the ground that closely matches the elevation of a child's mouth at an early age. Therefore, sanitation of the spigots as well as the reservoir should be a part of routine maintenance.

Process ozone diffusion by bubble reactor method in small static volumes of water with abbreviated water columns to diffused ozone levels satisfactory to disinfect microorganisms in brief time periods can be difficult to achieve. The chief hurdle involved is ozone diffusion contact surface area and time. The present invention is directed to an economical means of overcoming each of the factors that limit process ozone's potential disinfecting capacity. It is concerned with the optimization of each point in small automated ozonation systems both upstream and downstream from the ozonator. The object of this effort is to devise a single, economical, high longevity system capable of sanitizing all of the shapes and sizes of water dispensers in use today.

Until recently, the ozone water and related equipment sanitization and disinfection industry has been geared to large scale commercial, industrial and municipal applications not under space or equipment cost restraint. However, a growing demand for suitable sized ozone equipment with economy of scale for addressing less demanding, small sanitization and disinfection applications like water dispenser device sanitization has surfaced.

The chief difference between small and large applications is small applications are typically concerned with ozonating small, fixed, static volumes of water over adjustable dwell time intervals until adequate levels of disinfection or sanitization are achieved as opposed to large applications ozonation of continuously exchanged, large water volumes. The lowered number of variables offered by reduced temperature, static water volumes ozonated over time is the only built-in advantage available to small applications. During the process of re-engineering equipment and reducing costs to fit small application needs, it was found that beyond basic principles, much of the available industrial technology proved of limited value.

Attempts at using prior art to address small applications have resulted in either failure to achieve minimal levels of sanitization or where success was achieved, systems that could not remain cost competitive.

A number of factors influencing ozone diffusion into water by bubble reactor methods and their technical limitations related to small applications follows. Due to cost and space constraints small applications are limited to the use of small ambient air fed ozonators capable of generating less than 1% by weight ozone. This is contrasted by large scale applications' use of chilled LOX fed ozonators capable of generating up to 12% ozone by weight. Ozone is much more soluble in cold water than room temperature or warm water. A particular small application has little control over this factor. The water dispenser application is fortunate in the sense that average water temperatures are in an optimal 4-8 degree Celsius range. A large hurdle for small applications exhibiting static water volumes with a short (i.e., a few inches) water column is the ozone to water contact time. Bubble reactors usually vent more process ozone than they diffuse. The available options are longer dwell times, reduced airflow and smaller bubble size. Compare an average water dispenser's 1-3 liter volume, 4-6 inch water columns (0.15-0.21 psi back pressure), and 0.5-2 second bubble contact time at 1% ozone concentration with a large scale operation's 16-20 inches, 6-8.5 psi column's 15-20 second contact time with 12% ozone by weight. Since small systems are chiefly intermittent, auto-cyclic, programmable devices, this factor can be optimized by critical dwell time control and use of variable output ozonators for controlling both cycle width and ozone concentration tailored to water species, water volume and column height. Additional optimization is achieved by diffuser material choice and controlled airflow. Since small systems are chiefly scheduled for use in inside environments, over ozonation, using too high an ozone concentration and venting of surplus process ozone to air raises an air quality concern. It is imperative that small applications optimization addresses this potential health hazard. Small water dispenser applications (especially those using inverted water bottle) cannot blow large volumes of ozonated air into a small open systems bubble reactor reservoir containing a small volumes of water without either causing air displacement flooding of the reservoir or producing a substantial vapor phase that vents most of the water from the reservoir and reserve by evaporation. An additional difficulty is the loss of minimal head pressure, production of a large bubble with inadequate surface contact area resulting in a near total systems loss of process ozone. These factors are subject to optimization and are key to small applications success. Though large applications address flow control through fine bubble diffusers, its use is confined to high ozone concentration feed gas, fed through a high volume of fine bubble diffusers primarily for oxidation of bio-solids in moving volumes of water where bubble retention time is not critical. The data does not deal with potable water disinfection or sanitization parameters. Consequently the data on diffused gas to water and diffuser area to water volume ratios do not apply to low ozone concentration, time dependent small systems potable water sanitization.

Diffuser materials producing smaller bubbles per unit ozonated air volume exhibit a much greater surface area than like volumes of large bubbles. The higher the surface area, the greater the contact diffusion. Within limits, this factor can be optimized and is one of the main keys to successful small applications.

Internal Bubble Pressure: Small bubbles produced by fine bubble diffusers exhibit higher internal bubble pressures, hence greater diffusion by pressure/temperature relationship. In addition, their greater pressure retards their rise velocity, thus increasing contact and pressure/temperature diffusion time and affords higher structural integrity making them less subject to expansion and coalescence. This factor is optimized by diffuser material choice and control of airflow and is another key to successful small applications.

While prior patents have addressed water dispenser ozonators in general, various component, the present invention provides the means for optimization of ozone diffusion utilizing unique airflow control and diffuser technology. The purpose behind optimizing airflow is primarily twofold: first, to increase air dwell time across a cold plasma coronal discharge tube to increase ozone concentration and second, to reduce the large bubble fraction generated at the surface of a diffuser. The generation of small bubble sizes in gas diffusion bubble reaction chambers in order to increase surface area and contact time has long been an industry dream. However, the lack of need generated by past engineering success has caused industry to stop short of original goals.

Diffuser manufacturers have engineered small pore size, low permeable diffusers that in some cases require greater pump pressures for flow initiation. Higher pressure materials are not optimal for small low pressure/volume open systems applications as they decrease pump life and often do not supply an adequate volume of small bubbles for ozonation. Quite often, they are more subject to pore plugging than lower initial bubble pressure materials. The author's testing indicates that different manufacturer processing techniques for a single given media exhibiting identical mean particle and resulting pore size generate large variations in a diffuser's initial bubble pressure where at lowered IBPs, a diffuser will not only produce like sized bubbles, but a greater quantity of bubbles for less work. As a rule, the lower internal bubble pressure per same material and parameter diffuser will exhibit a greater spacing between active surface pore channels. Additionally, the less flow restricted material produces higher volumes of like sized bubbles with reduced vertical bubble velocity differentials and turbulence.

These preferred characteristics lead to decreased lateral and vertical bubble coalescing, reduced bubble expansion and rise rates, hence higher diffusion efficiency. Lower initial bubble pressure materials require a greater wall thickness and surface area to match the performance of higher initial bubble pressure materials. Otherwise, bubble size will increase to non-optimal proportions.

Conditions for minimal adverse bubble reactions in specific mean pore diameter/internal bubble pressure diffuser material producing specific bubble sizes at 0.05-1 liter/minute flow volumes in water columns ranging from 1-50 inch heights, include active pore spacings equaling thrice the bubble diameter both laterally and vertically at the diffuser surface where mean pore to bubble diameter ratio ranges from about 1:12.5 to 1:50. Application of these ratios to media diffuser surface area is tied to performance test treatment studies involving given water volumes and column heights, independently varying airflow rates at known ozone concentrations, and noting bubble size and bubble population size with respect to dissolved ozone concentration over a given time interval.

Once transfer efficiencies are determined for each situation, variable diffuser surface area tests noting bubble size and bubble population are performed and transfer efficiencies determined. By comparing the various flow and time varying studies against diffuser area studies and comparing bubble sizes and populations, one arrives at the optimal diffuser material surface area, flow rate and dwell time.

Prior art for commercial and industrial sized applications represents a balance between bubble size and bubble volume. Industry experience has been negatively influenced by misapplication of fine pore size diffusers to high solids and TDS fluids that promote rapid pore plugging, experience that crossed over to low mineral and solids water species like potable water disinfection. Furthermore, large commercial and industrial applications could not afford downtime on dynamic systems that operate 24 hours a day.

The use of very fine pore size diffusers application was largely abandoned by wastewater and potable water treatment out of past reservations and lack of research data for generating optimally engineered materials. To date, the recent interest in small applications has not triggered mainstream development of new diffuser materials/geometry innovations.

Although diffuser manufacturers typically produce fine pore diffusers to relatively homogeneous mean pore size standards, large pore sizes that channel high air volumes away from the smaller interconnected pore diameters occur in virtually every material tested. This is often complicated by an inability to effectively seal off material connection air leaks. Testing revealed that high permeability channel flows are the first to terminate large bubble production when airflow rates are reduced. This adjustment allows existing diffusers to operate at near rated design capacity and will serve as a stopgap measure until better solutions emerge. The optimal diffuser-airflow balance of small bubbles with reduced large bubble fraction displaying adequate remaining small bubble volumes suitable for ozonation occurs at approximately 50% of open flow rate on average for any given diffuser and water column height. This air volume reduction approximately equals the large gas bubble volume displaying poor diffusion characteristics.

The present invention thus provides an improved self sanitizing water dispenser apparatus as well as a method for generating ozone for cleaning the reservoir and the water contained within it.

BRIEF SUMMARY OF THE INVENTION

The present invention provides a self sanitizing cabinet type water dispenser that includes a cabinet having upper and lower end portions, the upper end portion of the cabinet having a cover. The upper end portion can house a reservoir that receives water (eg. filtered) from a municipal water system, well, or from a contained bottle. An upper opening can be provided in some models for receiving and holding an inverted a bottle of water (e.g. 3-5 gallons) to be dispensed. The bottle contains water to be dispensed, and provides a neck portion and a dispensing outlet portion.

A reservoir contained within the cabinet holds water to be cooled and dispensed. A refrigeration system cools the water within the reservoir. The reservoir can optionally be heated. A diffuser (e.g. ring) emits bubbles into the reservoir, the diffuser being disposed within the reservoir at the lower end portion thereof and preferably next to the reservoir wall so that bubbles emitted by the diffuser help scrub the reservoir wall.

An ozone generator is supported within the housing. Flow lines communicate with an air pump to carry ozone from the ozone generator housing to the diffuser. A blower generates flow and a flow line connects the blower to the ozone generator housing. In the preferred embodiment, ozone can be transmitted to the reservoir or to a flow channel that is upstream of the water dispensing spigot(s).

The spigot is provided with a switch for activating the ozone generator for a selected time interval. The ozone generator is activated for a selected time interval (e.g. a few minutes). After the selected time interval, the ozone generator is shut off. The air pump continues air flow for a time period (e.g. a few minutes) in order to help disperse any odor of ozone. The air pump is then shut off and the refrigeration system compressor starts operation again to cool the water.

The diffuser can be a ring shape, positioned around the side of the reservoir at the bottom of the reservoir. Such a ring diffuser can be positioned close to the intersection of the reservoir bottom wall and reservoir side wall. The diffuser can be of a composite construction that includes a porous core that is partially covered with a non-porous coating. The reservoir preferably has a center portion and the diffuser ring preferably has openings positioned to direct air away from the center portion of the reservoir. The reservoir can include a generally vertical side wall. The diffuser can be positioned to discharge bubbles against the side wall so that the side wall is scrubbed with ozone bubbles during sanitizing of the reservoir.

The ozone generator housing can be comprised of an upper housing section, a lower housing section and a gasket positioned in between the upper and lower sections. An ozone generator is contained within the interior of the housing. Fittings on the housing enable air to flow into and out of the housing. A blower generates air flow to carry air into the ozone housing and from the ozone generator housing to the air diffuser. Optionally, a HEPA filter can be provided as the air intake removes airborne microorganisms.

The present invention provides a compact, brief, high intensity, automated ozonation cycle and water cooler sanitization system and an improved ozone generating "tube" (see FIGS. 30-35). The engineering function dictating compactness is the space constraint of the insulated upper reservoir chilling compartment of a typical cooler reservoir. The present invention provides a self-contained ozonator module for achieving the shortest possible delivery path of process ozone to an in-reservoir diffusion system for minimizing chemically unstable ozone degradation losses and for taking advantage of immediate proximity to the reservoir cooling coil's lower air temperature as opposed to that of the compressor compartment.

A final need for systems integration and compactness is unit component cost, simplicity and reliability. The present invention provides an apparatus that is simple, reliable, rugged, and cost effective, and displays the ability to deliver a low cost, concentrated stream of ozone to a diffusion system needed to repeatedly "spike ozonate" small, changing static volumes of water or to an on demand faucet dispensed water flow stream. With the present invention, contact-diffusion brevity is imperative in achieving levels of sanitization not previously possible by micro-ozonation systems and small UV sanitization systems alike. This level of ozone concentration from air fed mini-ozonators has not been available for water cooler sanitization in the past, being available only in bulky form requiring either chilled feed gas, bottled oxygen or LOX as feed gas.

The present invention provides high output mini- and micro-ozonators suitable for intermittent short cycle ozonation. In this manner, in addition to cooler sanitation, the dispensed water quality is assured of being sanitary for consumption at all times. The present invention provides a spigot/faucet configured with a microswitch connected to an ozonator power circuit causing circuit activation during the time interval that the microswitch remains depressed. Alternatively, a faucet can be configured so that if depressed several times repeatedly, it signals a timer/controller to activate an air pump and ozonator until released.

In another embodiment, a reservoir volume-pressure change float sensor or air- or water-borne differential pressure transducer can be mounted in the cooler reservoir, which can be used to cause the ozonator to remain in operation until pressure restabilizes after dispensing is terminated.

Ozone is supplied by an ozonator/pump to a faucet water channel via flow stream to an additional diffuser located in the spigot water channel. This construction injects small quantities of diffused ozone into the flow stream for making and dispensing freshly ozonated water without fear of an ozone in air safety hazard. The safe and effective antiseptic properties of freshly ozonated water are known and offer a safe and effective means for sanitizing cooler exterior, drinking utensils or for neutralizing potential biohazards and hazardous organic chemical spills.

The present invention provides an energy efficient, low cost, intermittent repetitive reservoir and reservoir water spike treatment with a concentrated ozone cycle activated either by cooler compressor cycle or through timer/controller circuit with cooler compressor remaining in operation, brief ozonation time to bacteria-static levels followed by passive dissipation time interval, cycling continuously over a 24 hour daily period, and/or manual ozonator activation for dispensing freshly ozonated water, ozonated to non-taste, non-harmful, bacteria-static levels. In this fashion, no harmful bacteria is contained in the remaining bottled water or cooler reservoir or water dispensed from a municipal source fed point of use.

The present invention's higher outputs and alternative cycling has been demonstrated effective in mixing transfer of diffused ozone and resultant secondary peroxyl group residuals from cooler reservoir water to water contained in water bottles over time by standard indigo dye test where indigo dye is introduced into a cooler reservoir, a water bottle containing water is added, dye dissolves and transfers to a bottled water coloring the water blue. After an ozonation cycle is run, the diffused ozone mixing transfer to water bottle is observed when the oxidant sensitive dye degrades and water color returns to transparent.

These new features extend the water service industry's onsite automatic sanitization options to include not only cooler reservoir and bottled water sanitization, but to faucet watercourses and dispensed water as well. The same timer/controller circuit found on auto-cycling cooler sanitizers with sufficient micro-chip memory can be programmed to include both long cycle compressor disconnect, ice ring melting, ozonation to antiseptic conditions, subsequent dissipation, compressor reconnect and intermittent repetitive bacteria-static cycle cooler sanitization cycles as well as the manual override activated freshly ozonated, dispensed water function.

Where only an intermittent spike ozonation cycle is required, the timer circuit in some cases may be eliminated and a more simple, cost effective ozonator-pump-diffuser set-up can be installed on a cooler by power circuit attachment to the cooler compressor so that pump and ozonator cycle with the cooling cycle.

In the event a compressor cycle is longer than needed for achieving antiseptic conditions, the above set-up may require a simplified programmable timer/controller circuit that allows for start-up with the compressor, but shuts off after a bacteria-static diffused ozone level cycle width has occurred. The cycles that are available with the present invention were not formerly possible or provided for by prior art examples of retro-fitted or integral auto-cycling water cooler air-fed micro-ozonator due to their inability to achieve ozone concentrations and diffusion transfer needed to "spike ozonate" a standard cooler's static two liter volume maximum of water much less that of larger volume coolers exceeding 1 gallon reservoir volumes or small dispensing flow stream's flow rate maximum of 2 l/minute to at least bacteria-static levels under the imposed time constraints.

The ozone concentration required to spike ozonate water with the proper diffusion technology operating at low pressure is 3-4 times the output of the highest output prior art micro-ozonators known to applicant, meaning a micro-ozonator capable of continuously delivering 600-800 mg/hr ozone concentration in air coupled to a state of the art low bubble pressure, micro-porous, hydrophobic ceramic material diffuser (preferably of a ring shape) mounted on the cooler reservoir bottom like that disclosed in prior U.S. Pat. No. 6,289,690. The desired ozone output has been accomplished by simple substitution of this discharge tube embodiment for prior art in said prior art's power circuit contained within its existing case.

The intermittent repetitive cycle widths for a cooler micro-ozonator system activated by timer/controller circuit can be based effectively on how different water species respond to ozone. Acidic water species are easy to ozonate, but require more time for diffused ozone to dissipate from the water to below taste levels, whereas basic or alkaline water species resist ozonation and will not hold diffused ozone for any length of time at any given water temperature.

Ideally, for a given cooler, reservoir water temperature average of 40° F., the intermittent, repetitive cycle ozonation cycle should be based on the length of time it takes to spike ozonate a pH 9 water volume to bacteria-static levels with a dissipation time equal to that requiring pH 5.2 distilled water to be free of dissolved ozone content in order to accommodate all water species using a single pre-programmed timer cycle.

An additional factor of concern related to spike ozonation cycles is the presence of bromine in source waters. Ozonation above certain levels of diffused ozone in water converts bromine and certain bromine compounds to bromate, a suspected carcinogen. FDA Safe Drinking Water Act regulations have recently been amended to include a maximum contaminant level for bromate in drinking water of 10 mg/l, possible decreasing to 5 mg/l within a year. Ozone oxidation of bromine to bromates is a function of ozone concentration, exposure time, temperature and water pH.

The various solute bearing water species at risk for oxidative conversion of bromine to bromate range in pH from 1-7, more specifically fresh and processed water supplies of pH 5-7, the range from distilled water through pH neutral mineral bearing water sources commonly used in bottled product. Thus spike ozonation may be the only safe, effective and cost effective means for controlling bromate production in water undergoing ozonation while achieving adequate levels of disinfection and/or sanitization. Luckily, cooler water temperatures are low enough to alleviate some of the potential difficulty. Water briefly spiked with ozone, held at levels below the diffused ozone concentration threshold for bromate production over brief intervals will result in minimal production of bromates in waters containing elevated levels of bromine and its compounds.

Spike ozonation can also be accomplished without a timer/controller by altering a cooler's compressor cycles to correspond to these timed cycles provided the alteration does not adversely affect a cooler's ability to operate within its chill water volume design parameters. If water remains in a cooler reservoir unused over repeated cycles, the bacteria-static oxidation level will move to a bactericidal oxidation state, as more of the static biophage is rendered non-living and inert.

The present invention provides an improved coronal discharge tube arrangement. Whereas a prior art 200 mg/hr ozonator is capable of achieving bacteria-static diffused ozone levels in 1-2 liters of water in 20 minutes with proper diffusion technology that may better approximate a cooler chill cycle and offer better ozone dissipation time through reduced diffused ozone quantity present in water, said ozonator is incapable of spike ozonating a flow stream of water dispensing from a cooler to any degree at all to form a multifunction water cooler ozonation system or a system capable of spike ozonating cooler reservoir water volumes to like bacteria-static levels in under 5 minutes operating time and allowing the remaining 15 minutes to be spent dissipating the ozone to below taste levels.

The shorter the cycle widths, the greater the surety of sanitized cooler and water. Additionally, said smaller output miniozonators cannot effectively sanitize larger reservoir volume coolers of the type whose water volumes exceeds one or more gallons in a timely fashion. Poorly thought out and engineered past attempts at ozone sanitizing water coolers include methods such as continuous ozonation of water using low output small ozonators. This effort has a threefold disadvantage. First the continuous introduction of ozonated ambient air causes an added energy debt to a compressor having to run all the time to cool the water, thus effectively shortening compressor, ozonator and pump life. Secondly, the continuous introduction of dust, organics and micro-organisms found in air shortens discharge tube life and unnecessarily introduces pollutants into the reservoir and contained water, thus increasing oxidation load and rendering the water potentially non-potable. If the discharge tube fails by overheating caused by dust and/or moisture build-up on an electrode or the dielectric, the system continuously introduces an unoxidized, unsanitary load into the cooler reservoir or builds up in the discharge tube to the point that the resulting blockage causes pump failure. This is one reason why this embodiment offers an inexpensive, quick-change throwaway, sanitary discharge tube option that is far below the cost of the less expensive UV sanitization system replacement tube requiring more frequent replacement. Third, ozonators specified for this purpose frequently have too small an output to oxidize the load found in water where the small quantity of diffused ozone either dissipates or does not have time to build to adequate levels to perform its function when coolers are subject to heavy use.

In addition to air dielectric breakdown leading to ionization, ozone generation by the coronal discharge method generates light and heat. A portion of said light lies in the far ultra-violet ionizing radiation spectrum and is responsible for cleaving the diatomic oxygen molecular bond. This preparatory bond cleaving is necessary for ozone formation. Such far UV ionizing radiation light fraction can be conserved and recycled by reflection. When a cylindrical mirrored reflecting surface is employed, a dramatic increase in oxygen to ozone conversion efficiency is noted over prior art.

In a further embodiment of the apparatus of the present invention, a water dispenser is provided that includes a cabinet having upper and lower end portions and an interior. A reservoir is contained within the cabinet, the reservoir containing water with a water surface. One or more spigots is in fluid communication with the reservoir for dispensing water from the cabinet. Each spigot preferably provides a manually operable valve handle that opens the spigot to dispense water from the spigot.

A refrigeration system for cooling water within the reservoir can be optionally provided. An ozone generator housing is supported next to and preferably inside of the cabinet, the ozone generator housing having an ozone generator inside and air flow lines for transmitting air to and from the housing interior and to the reservoir.

Air pumps that are used as part of the present invention need be of sufficient capacity to overcome system pressure losses and provide a continuous adequate volume of ozonated air necessary to achieve water and reservoir surface disinfection within the largest water dispensers and vending machines without causing permanent deformation of pump materials, overheating or conditions leading to premature capacity loss or failure. Automated systems ozonating small static water volumes are designed for brief, intermittent cyclic operation, conditions under which pumps are given adequate time for thermal dissipation and elastic materials recovery; therefore air pumps need not be of a type normally associated with long-term continuous operation.

To preclude potential damage by back-feed of residual process ozone after shutdown, only pump components specified as ozone resistant are selected and claimed. Suitable ozone resistant elastic materials include, for example, Viton and silicone polymers and in less demanding applications the EPDM rubber material. Hard ozone resistant components include 316 stainless steel, ceramics, glasses and polymer materials such as polycarbonate, teflon, kynar and certain formulations of polypropylene.

The present invention discloses high longevity, low volume, low pressure air pump manufacturer parameter ratings proven suitable for water dispenser sanitization application and include a "shut in" pressure maximum of 5 psi, unrestricted open flow pressure of 0.1 psi with unrestricted flow rates of between 1-10 L/minute, with an ideal range of between about 3.4-4 psi, and optimally about 0.1 psi open flow with unrestricted flow rates between about 1.2-4 L/minute. These pumps can be typically of the 100-110/220-240 VAC, 2-12 W, 50-60 Hz or 6-24 VAC or DC electromagnetic, diaphragm type with or without built-in variable flow control valve or variable motor speed flow control, low voltage rotary AC or DC motor diaphragm type.

These pumps exhibit sufficient pressure to pump against all systems losses and a water column hydrostatic head of 50"=1.8 psi at mean sea level with surplus airflow for operation at elevations above 10,000' under air flow rate control. We claim pumps with these specifications for use with water dispenser sanitization systems.

The present invention, in one embodiment extends the acceptable diffuser design geometries while retaining the original ring concept and function to allow for greater flexibility of ring shapes and material types that conform to varying dimensions of reservoirs and reservoir shapes found on different water dispensers and defines specific range of diffuser materials parameters and performance characteristics suitable for use with pumps of the above listed pressures and outputs. It also teaches a new materials, configuration and principles art for fine bubble diffusers and diffusion.

One ring geometry alternative to a fixed, single material design is a universal, flexible, segmented diffuser concept that can be made in extended lengths, can easily be joined to other lengths of the same material with common barbed fittings, can be cross-cut to specific lengths and can be easily bent to conform to any reservoir shape or dimension. This diffuser emits bubbles from its exterior edge against the side walls of a water dispenser reservoir for promoting a scrubbing action and inward and downward convection water flow promoted by small bubble viscous drag of the reservoir water fraction to aid in elimination of gas bubbles entering bottles found on water dispenser types using an inverted water bottle and all other types, for the extended purpose of recycling slow or counter-rising very small bubble flow whose dimensions are such that they do not rise appreciably like larger bubbles, thus increasing bubble retention and ozone contact time.

The present invention utilizes small diffuser material segments, configured in cylindrical hat shaped tablets (see FIGS. 37A-37F) or stepped rectangular segments with radiused corners having distinct ninety degree edges. These segments are embedded in a continuous ozone resistant silicone or Viton elastic housing material (see FIGS. 36-40). During the heat forming polymerization process, liquid polymer feedstock is injected under pressure into a mold cavity containing said segments. The silicone or Viton housing conforms to the rugose surface of the segmented diffuser material and edges, that upon cooling and removal from the mold. The polymer body shrinks around the individual diffuser segment surfaces and edges, forming a permanent pressure seal that encapsulates each segment on all but the exterior flat face. The opposing face is open to an interior, common airflow channel and a connection to an air flow pump. A continuous air channel in connection with each diffuser segment is provided in the diffuser encapsulating elastic material. Sufficient space is provided between diffusers to allow for flexibility with sufficient wall thickness so as to preclude airflow restriction of the common airway supply channel and to conform to upsets found on many types of water dispenser reservoir bases. Once formed, extended lengths of the flexible material can be either cut to desired length, or joined to other lengths end to end and bent to configure to a specific reservoir near basal cross-sectional dimension and T-barbed to ozonated air supply line. Diffuser ring OD should be undersized by a minimum of 0.25 inches to provide a sufficient annular gap between reservoir ID and diffuser OD to minimize bubble coalescing after being emitted from a diffuser via collision rebound off the reservoir wall back into the diffuser face where bubbles are forming as well as supply an annular channel guide for bubbles rising against reservoir wall and convection water flow around diffuser.

Complete reservoir water volume toroidial convection flow is the only type of turbulence acceptable to this embodiment. A food grade and ozone proof diffuser material is specified for this diffuser design that are porous fused alumina or silicon carbide particles or porous sintered particle stainless steel or titanium. The specific advantage of a flexible diffuser material manufactured in long lengths is that application is not limited to a single closed loop diameter of the material, but can be configured in several wraps of the cost effective material in a flat coil to provide more diffuser surface area when needed.

A second, alternative universal, flexible diffuser design features a continuous thin, narrow strip of either food grade sintered particle stainless steel or titanium metal diffuser material. Normally these types of materials are subject to breakage when bent. However, the availability of a newer thin strip or ribbon configuration of this material, 1 mm in thickness across the flats allows for bending to all but the tightest radiuses for housing in either a thin walled, food grade stainless steel or polymer backing with integral, common air channel. This design displays the least cross-sectional dimensions possible of any material for minimizing water displacement of reservoir water fraction and ease of wrapping tight, flat heli-coils of the material to the desired surface area requirement for any given diffusion application. The advantage of wrapping additional loops or having a narrow double sided diffuser surface area with desired spacing between coils lies in surface area increase, avoidance of bubble collision coalescing and promotion of multiple convection water flows for better diffusion mixing and elimination of the possibility of rising bubbles entering water bottles and generating displacement dispenser flooding.

A third alternative diffuser media is an elastic tube membrane diffuser. This media consists of a preferentially slotted elastomeric tubing that is permeable to air and impermeable to water, thus forming its own check-valve. Its chief advantages are its flexibility and resistance to pore plugging. A small diameter, thin walled elastic tubing, displaying several rows of offset slots whose slot length is here specified at 0.25 mm or less, spaced 1-2 mm apart are inlet through one side of the tubing to form a directional diffuser tubing that will blow 0.25 mm diameter or less, non-coalescing bubble streams that instantly release from the media. Instant release can be insured by a teflon coating of the material's exterior surface. The material wall thickness is preferably on the order of 0.25-0.5 mm to achieve the desired results. A specified ⅜"-¾" OD tubing is cut to length, bent to conform to the reservoir perimeter with opposing ends configured to a T-barb fitting, slots facing outwards toward the reservoir walls to form the diffuser ring. Alternatively, a greater length is cut and formed in a flat coiled arrangement if application calls for a greater surface area diffuser. If sufficiently small tubing is unavailable, short lengths of large diameter membrane diffuser tubing may be used. The tubing is fitted over a ring housing displaying a channel cross-section with flanges facing outward. Tubing section placed over the open channel is then pressure sealed along the edges of the channel by two snap rings applied to upsets provided on the channel forming the elastic material's pressure seal. A barb is let through one face of the channel ring's flats to serve as an air supply connection to the common ring air channel.

Acceptable diffuser materials suitable for water dispenser sanitization applications can typically and will preferably exhibit the following parameters and characteristics. Such diffusers have an ability to function optimally at all water column heights under consideration within the specified operating capacity range of air pumps. They display the ability to produce an adequate volume of small bubbles in a preferred size range of 0.1-1 mm diameters that display the preferred rise rates of 1-10 cm/second to achieve good bubble retention ozone contact time and the greatest level of diffused ozone. Hard diffuser materials having this capacity under air flow controls display mean surface pore size dimensions ranging from 10-60 microns with wetted media initial bubble pressures measured in air of between 0.1-0.7 psi when operating at air flow volume rates of between 0.05-2 L/min depending on water column height and volume being ozonated. The optimal parameter range is from 10-50 micron mean pore size dimension, wet media initial bubble pressures of 0.1-0.55 psi and flow rates between 0.1-0.5 L/min.

Where possible, use of hydrophilic, polar or nanoparticle veneers applied over diffuser surfaces that do not close off pores for increasing surface energy at the pore opening, thus promoting small bubble production is recommended. Veneer thickness is minimal and more or less protected by the pore indention to resist abrasion. Since the light powder coating is minimal and does not extend to any depth within the pore channel, the risk of pore channel plugging or fouling or permeability restriction is minimized. Applied veneers suitable for this purpose include, for example, polar metal nano-particles, alumina, silica or silicon carbide spherical nano-particles, zeolites or silica gel nano materials fused to the exterior surface and ground off such that their presence is limited to the area immediately around the pore opening indentation. Such diffusers minimize the production volume of large fast rising bubbles that generate eddy current turbulent flow contributing to lateral and vertical bubble coalescing. Such diffusers also minimize the vertical bubble flow velocity differential that contributes to bubble stream coalescing that occurs during the first 2 inches of bubble rise above a diffuser.

The diffusers of the present invention present a new principle of diffusion technology. Bubble reactors rely exclusively on diffuser materials to generate bubbles for surface contacting of a gas during buoyant rise through a water column. During experimentation with various semi-permeable exterior mineral coatings for directionally gating air bubble flow, a new phenomenon was observed. Samples taken immediately below the bubble streams emitted by the gated diffuser displayed anomalously high levels of diffused ozone. Like non-permeable coated diffuser rings were tested at the same points for comparison. The second group of diffusers did not exhibit these same high levels of diffused ozone. Examination of the non-glazed coatings revealed that they were semi-permeable to water and wettable or hydrophilic in nature. After the coating hydrated, it exhibited enough remaining permeability to wick free water by capillary pressure back into the diffuser material when assisted by the weight of the water column working against the diffuser's internal air pressure. After a period of operation in a water column, airflow through a permeable diffuser material exhibits a tendency to dry out internally through evaporation. It is not known if this evaporation includes the bound water fraction, but certainly includes most of the free water fraction. Measurements of diffused ozone concentrations taken in static volumes of water over time normally exhibit an initial high diffusion rate that levels off and flattens over time. Although this is chiefly due to the gradual saturation of the fluid with ozone, a percentage of it may be due to evaporation of water from within the stone. The principle at work here is exposure of evaporative cold water under pressure to an atmosphere of ozone gas causing ozone saturated water vapor and free water phase within the diffuser material being ejected along with bubbles. The saturated free water and vapor phase is infinitely soluble compared to ozone gas in water. We know that every vapor droplet that strikes the liquid surface enters the liquid since it immediately experiences large forces pulling it into the liquid. At any given vapor temperature, the number of molecules per second striking the unit area of the surface is proportional to the vapor pressure; thus, immediate recondensation to a liquid phase occurs. Since ozone dissolves better in cold water and at higher pressures, an ultra high surface area cold vapor approach to ozone diffusion will yield gas saturated vapor and resolution of the vapor phase back into the liquid in brief time intervals.

Two diffuser technologies are revealed for capturing this in-diffuser cold water vapor diffusion method. The first method utilizes the passive approach of applied partial semi-permeable capillary material coatings over an existing diffuser material exterior surface for wicking moisture back into the diffuser mass, assisted only by the water column. A particular diffuser material is selected that exhibits an excess of surface area equaling diffuser exposed surface to match water volume for bubble diffusion plus the surface available for coating and estimated air flow rates needed to achieve bubble diffusion mass transfer over unit time. A coating that displays the needed permeability to water and non-permeability to the pressurized air fraction is then applied. This entails selection of a high surface energy coating placed against a low surface energy diffuser material to achieve fluid transfer back into the diffuser for resultant diffuser rewetting when assisted by the specific water column pressure. A suitable coating tailorable to both permeability requirements and addition of hydrophilic or polar materials dispersed phase aggregates is the HERA Corporation's cold process, alumno-silicate, microporous, pseudo-ceramic, hydrolytic cement. This material eliminates the need for additional kiln firing or sintering of the coating onto the diffuser that might adversely affect permeability. In fact low cost diffusers can be made exclusively from the material. Once configured, continuous water circulation back into a diffuser and generation of a cold water vapor phase by evaporation within the diffuser is insured. The nano-droplet vapor phase exposed to an atmosphere of ozone will produce a vapor saturated with ozone that immediately transfers to the reactor's water volume when emitted from the diffuser, greatly enhancing the diffusion efficiency of the bubble reactor.

A second means disclosed is an active method for generating the water vapor and ozone gas mixed phase within the diffuser internal air supply cavity or chamber. Here both ozonated air and a fine water mist are pumped into the chamber for pre-mixing and diffusing ozone into the vapor phase within the diffuser cavity prior to the mixed phase's diffusion through the more permeable diffuser into water. This type of diffuser consists of an internal micro-fine pore diffuser, preferably axially mounted within the air bubble diffuser. Pure water is pumped through the micro-fine diffuser and converted to cold water vapor phase within the annular air supply channel where it is mixed with the pressurized ozonated air supply and pumped through the higher permeability air bubble diffuser material. The annular volume reaction chamber is sufficiently large to allow enough contact time for the pressurized gas to dissolve into the cold vapor fraction prior to release through the more permeable bubble diffuser. Since a high fraction of the gas is now diffused into the water vapor that immediately dissolves in the main water volume, the lower quantity of remaining gas surrounded by the vapor fraction being extruded through the wetted pore capillary elastic water membrane venturi orifice allows for production of smaller more diffusive bubbles and anti-bubbles. An anti-bubbles is a known double layer form consisting of a higher density cold water droplet core surrounded by a thin layer of gas in bulk water. This type of bubble will not rise, but counter-flows, diffusing its annular trapped gas into both the bulk fluid and contained water droplet until extinction. This form of diffusion offers gas diffusion mass transfer efficiencies equal to or greater than static mixer assisted, venturi siphon-jet diffusion. Since this process is occurring at point of use, the normal ozone recycling loop and instability losses associated with the venturi-siphon jet method are eliminated. Since a smaller gas phase to bubble fraction is involved, this method is preferred over all other methods for sanitization of water dispensers. When properly engineered for complete mixed phase gas solution within a diffuser, the method will replace bubble reactors altogether. This new principal of diffusion and two new diffusion technical innovations are claimed for use with water dispenser ozone sanitization systems.

Two designs for are disclosed manually adjusting or otherwise controlling or metering air flow through an ozonator and diffuser for the purpose of increasing oxidant concentration and/or regulation of bubble size, bubble population size and rise characteristics are disclosed herein for use on water dispenser sanitization systems.

While more sophisticated automated feedback control means may be available for metering ozone sanitization systems air flow and flow controlled pumps are available either through motor RPM voltage adjustment or needle valve mounted on a pump housing, this first design relates to an orifice type needle valve flow adjustment during visual observation of bubble size changes in a reservoir. In this case, flow controlling valve made of either an ozone resistant metal or polymer is placed either between air pump and ozone discharge tube or downstream from discharge tube housed inside the single module along with a timer cycle controller circuit. A valve stem extends through a hole in module case and a vertically striated knob with dial pointer is inserted over valve stem. A circular veneer decal, calibrated to flow rate and adjustable over a 340 degree turn radius from closed to full open is provided on the external casing along with a pointed upset molded into the casing whose set stop point sets into the knob grooved striations provided, serves as a ratcheting set to secure a preferred optimized flow rate.

A second flow control design consists of a variable inline flow meter for attachment to the vertical segment of ozone supply line tubing.

A third and preferred method for auto-controlling systems air flow through ozonator and diffuser for water dispenser sanitization systems is disclosed. A type of existing airflow regulator known as a spring-loaded variable orifice is herein modified for this application. This modification includes dual adjustable orifices, a screw adjustment for altering orifice restriction, and a thin bimetal material forming the valve body that acts as both heat sink and secondary regulating mechanism or thermostat. This type of device maintains a specific flow rate while responding to changes in temperature and airflow. Addition of the tension adjustment screw allows the flow parameters to be adjusted to a specific flow rate. Once adjusted, flow is maintained in the conventional sense as outlined above. In this case this auto-flow regulating mechanism is located downstream from the ozonator.

The purpose of the bimetal material possessing two dissimilar linear coefficients of thermal expansion is for better response to changes in temperature where outer material doubles as an ozone resistant material, preferably nickel plated copper. Since a bimetal material is designed to respond to temperature in a spring-like manner.

The need for the addition of a temperature dependent flow control lies in the fact that while suppressing airflow across an ozonator can and does elevate levels of process ozone, it also elevates air density and temperature. If flow is suppressed for a sufficient period of time, the elevated temperatures can destroy process ozone and thermal expansion of air will increase flow rate while decreasing air density. Thus a means for temporarily increasing airflow is provided to vent excess heat and prevent the destruction of process ozone.

Heat from the ozonated air is transferred to the thin bimetal walled, heli-coiled bellows valve body, promoting linear expansion of same, thus allowing a slightly greater airflow to diffuser until air temperature is again in an optimal range. In this case the auto-valving flow control mechanism resembles the conventional water cooled engine's thermostat with addition of a flow adjustment. Since air is a poor conductor of heat, airflow is made to spiral around the entire helical surface of the bimetal bellows to ensure a maximum, even heat transfer to the metal. The second adjustable orifice or thermostat orifice and seat is located at the base of the valve/bellows. Once first orifice is adjusted for airflow during cold operation, the mechanism is free to respond to changes in temperature for secondarily regulating airflow and air temperature automatically. Device is simple, consists of minimum quantities of readily available inexpensive materials and can be fabricated and sold inexpensively. Device is claimed for use with water dispenser ozone sanitization equipment as an auto-airflow/temperature control optimizer.

BRIEF DESCRIPTION OF THE DRAWINGS

For a further understanding of the nature, objects, and advantages of the present invention, reference should be made to the following detailed description, read in conjunction with the following drawings, wherein like reference numerals denote like elements and wherein:

FIG. 7 is a fragmentary view of the preferred embodiment of the apparatus of the present invention illustrating an alternate construction for the diffuser;

FIG. 8 is a fragmentary, sectional view of the diffuser of FIG. 7 showing the porous body portion thereof;

FIG. 9 is a fragmentary, sectional view of the diffuser of FIG. 7 prior to a grinding of part of the non-porous surface therefrom;

FIG. 10 is a schematic, fragmentary view illustrating the diffuser of FIG. 7 during construction;

FIG. 11 is a sectional view taken along lines 11-11 of FIG. 7;

FIG. 12 is a sectional view taken along lines 12-12 of FIG. 7;

FIG. 13 is a fragmentary, perspective view illustrating the diffuser of FIG. 7;

FIG. 14 is a sectional view taken along lines 14-14 of FIG. 7;

FIG. 15 is a partial perspective view of a second embodiment of the apparatus of the present invention;

FIG. 16 is a partial sectional elevation view of the second embodiment of the apparatus of the present invention;

FIGS. 38-40 are partial perspective views of the third embodiment of the apparatus of the present invention illustrating the improved diffuser and methods of manufacturing same;

FIGS. 43A-45C show a diffuser that is similar to the diffuser of FIGS. 43-45, and that utilizes a sintered metal sheet that ozone diffuses through during use.

FIG. 49 is an elevation view an in line, variable flow flowmeter with air control valve for use with any of the embodiments the present invention;

FIG. 50 is an exploded sectional view of the control valve of FIG. 49;

FIG. 51 is an exploded sectional view of the control valve of FIGS. 49-50;

DETAILED DESCRIPTION OF THE INVENTION

Figure 1:
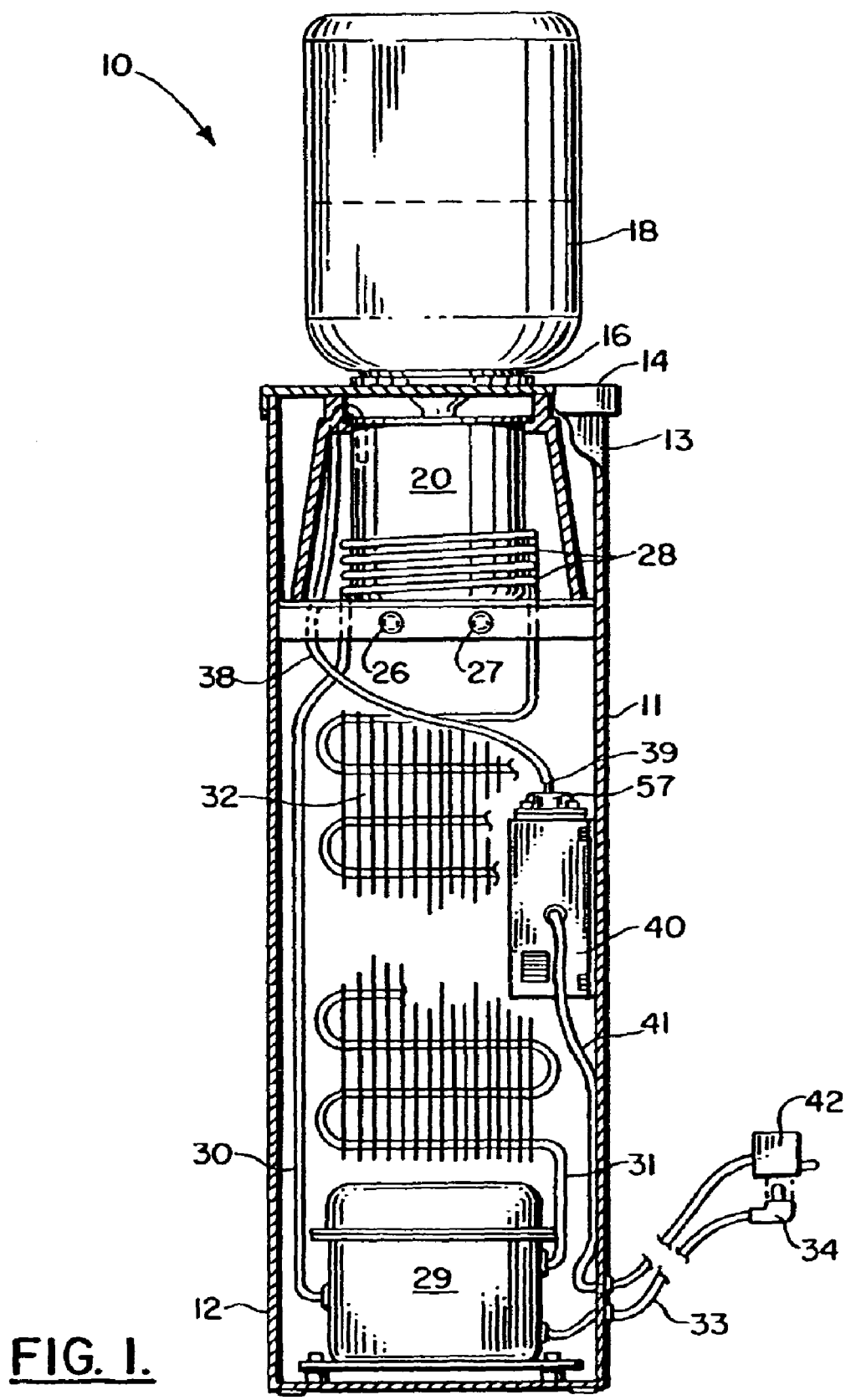
FIG. 1 is a sectional elevational view of the preferred embodiment of the apparatus of the present invention.
Figure 2:
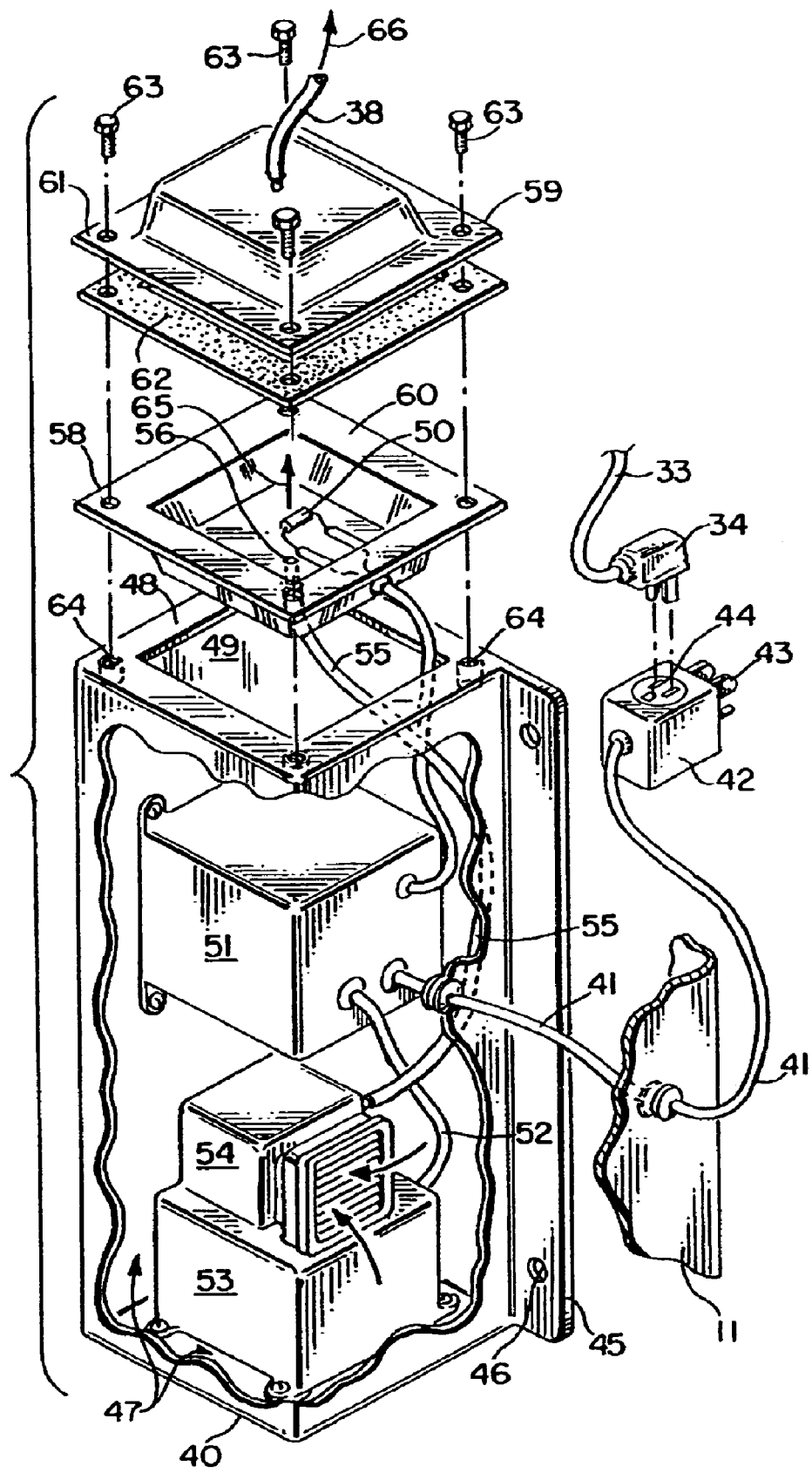
FIG. 2 is a partial perspective exploded view of the preferred embodiment of the apparatus of the present invention illustrating the ozone generator portion thereof.
Figure 3:
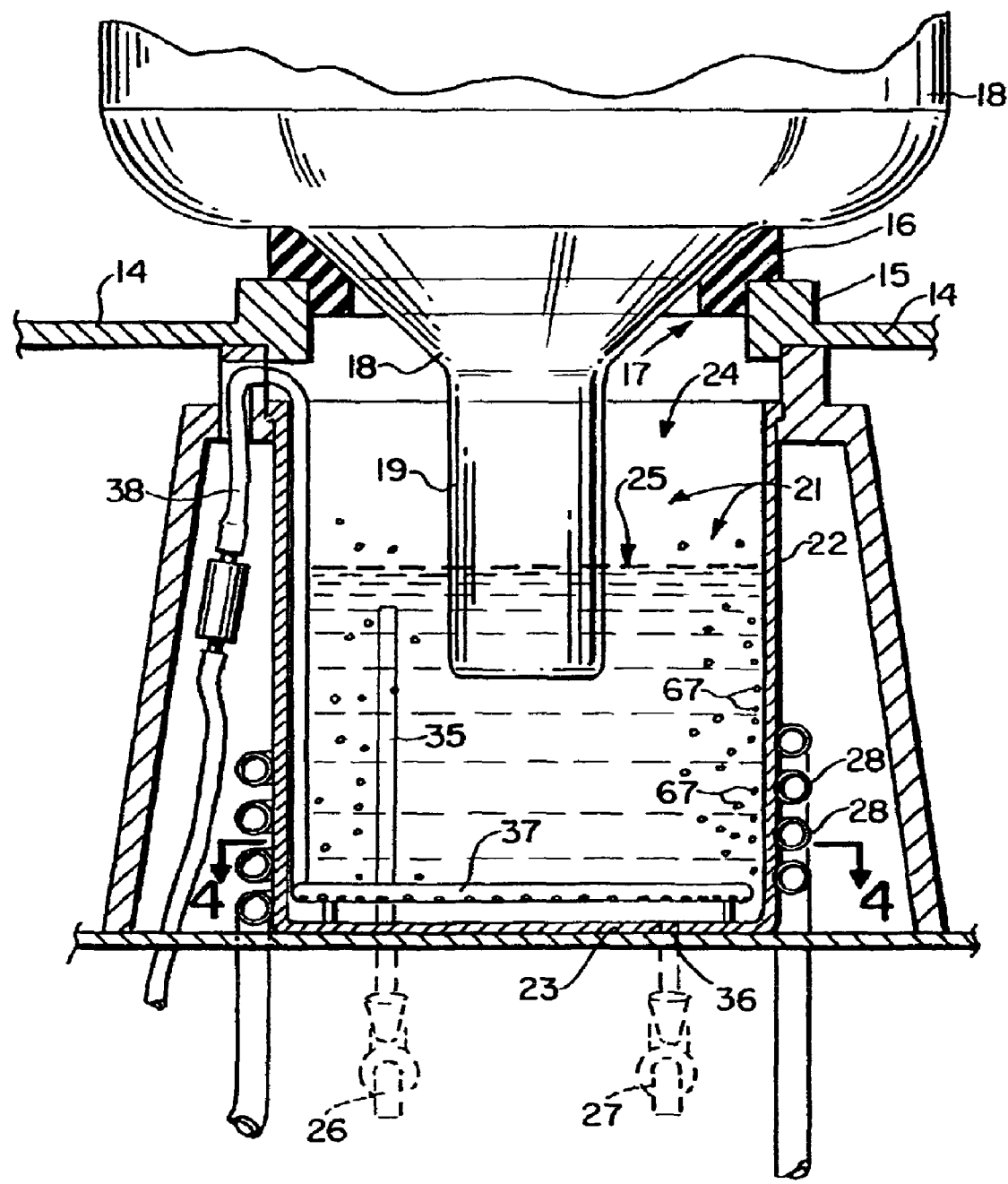
FIG. 3 is a partial sectional elevational view of the preferred embodiment of the apparatus of the present invention illustrating the reservoir, bottle, and ozone diffuser portions thereof.

FIGS. 1-3 show generally the preferred embodiment of the apparatus of the present invention designated by the numeral 10 in FIG. 1. Water dispenser 10 provides an improved apparatus that sanitizes the open reservoir from time to time with ozone. The apparatus 10 includes a cabinet 11 having a lower end portion 12 and an upper end portion 13. The upper end portion 13 carries a cover 14 having an opening 17.

The opening 17 provides an annular flange 15 and a gasket 16 that defines an interface with bottle 18. The bottle 18 is a commercially available bottle that is typically of a several gallon volume (e.g. five gallons) in the United States. The bottle 18 provides a constricted bottled neck 19 that is placed inside an open reservoir 20 as shown in FIGS. 1 and 3 during use. The bottle neck 19 has an opening for communicating with a reservoir 20 at the interior of the cabinet 11 that holds the water product to be dispensed and consumed. When the reservoir 20 is lowered during use, air bubbles enter the bottle 18 and water replenishes the reservoir 20 until pressure equalizes.

The reservoir 20 has an interior 21 surrounded by reservoir sidewall 22 and reservoir bottom wall 23. The reservoir can be, for example, generally cylindrically shaped and of a stainless steel or plastic material. The reservoir 20 provides an open top 24 for communicating with the neck 19 of bottle 18.

During use, reservoir 20 has a water surface 25 that fluctuates slightly as water is dispensed and then replenished by bottle 18. One or more spigots 26, 27 can be provided for withdrawing water contained in reservoir 20. In the embodiment shown in FIG. 3, for example, a left hand spigot 26 has a flow line 35 that extends up to and near the surface 25 of water contained in reservoir 20. The spigot 26 thus removes ambient temperature water from reservoir 20 that is not in close proximity to the refrigeration or cooling coils 28. The spigot 27 provides a port 36 for communicating with water contained in reservoir 20. Because the refrigeration coils 28 are positioned at the lower end of reservoir 20, the spigot 26 withdraws cool water. As a practical matter, a water dispenser apparatus 10 could provide either ambient temperature water, cold water or heated water if, for example, a flow line 35 were to be provided with a heating element.

For cooling the water at the lower end portion of the reservoir 20, a cooling system that includes a compressor 29 can be provided. The refrigeration system includes flow lines 30, 31 in combination with compressor 29 to transmit cooling fluid to coils 28 and then to heat exchanger 32 as part of a system for cooling water in reservoir 20. Power to the apparatus 10 is provided by electrical lines, including an electrical line 33 provided with plug 34. The plug 34 can be fitted to controller 42 having receptacle 44 and plug 43 as shown in FIG. 2. In this fashion, electricity can be selectively routed to the compressor 29 via electrical line 33 or to the housing 40 containing ozone generator 50 using electrical line 41. This feature enables the compressor to be deactivated when the ozone generator 50 is to be used to transmit ozone to reservoir 20 for cleaning water contained in it and for scrubbing the inside walls of reservoir 20.

In FIGS. 1 and 2, the housing 40 includes an ozone generator 50 that generates ozone for cleaning water contained in reservoir 20. Additionally, the housing 40 contains a motor drive 53 and blower 54 that move air through an ozone generator housing 57 to diffuser 37. Air line 38 communicates between ozone generator housing 57 and ozone diffuser 37. Fitting 39 provides a connection for attaching the exit air flow line 38 to ozone generator 57 as shown in FIGS. 1 and 2.

Housing 40 can be provided with flanges 45 and openings 46 for enabling the housing 40 to be retrofitted to an existing cabinet 11 by bolting the housing 40 to the cabinet 11 as shown in FIG. 1.

In FIG. 2, housing 40 includes a lower end portion 47 and an upper end portion 48. The upper end portion 48 provides an opening 49 to which ozone generator housing 57 can be affixed. An ozone generator 50 is contained within the housing 57 as shown in FIG. 2. Housing 57 includes a lower housing section 58 and an upper housing section 59. Flange 60 of lower housing section 58 and flange 61 of upper housing section 59 each engage gasket 62 upon assembly.

Bolted connections 63 can be used for attaching the housing 57 to housing 40 at internally threaded openings 64 on housing 40 as shown in FIGS. 1 and 2. During use, the controller 42 normally deactivates the ozone generator 50 during normal hours when the users are dispensing water from the apparatus 10. Because the ozone used to disinfect reservoir 20 has a distinctive smell, it is preferable to clean the water contained in reservoir 20, to clean the inside walls of reservoir 20 and the bottle neck 19, at a selected time. The controller 42 could be activated for example during early morning hours (e.g. 3:00 a.m.-4:00 a.m.) and can be a commercially available controller that activates transformer 51 and motor drive 53 only after compressor 29 and the refrigeration system have been deactivated by the controller 42. This accomplished by shutting off the flow of electricity to plug 34 and electric line 33 that supply electricity to compressor 29.

Figure 4:
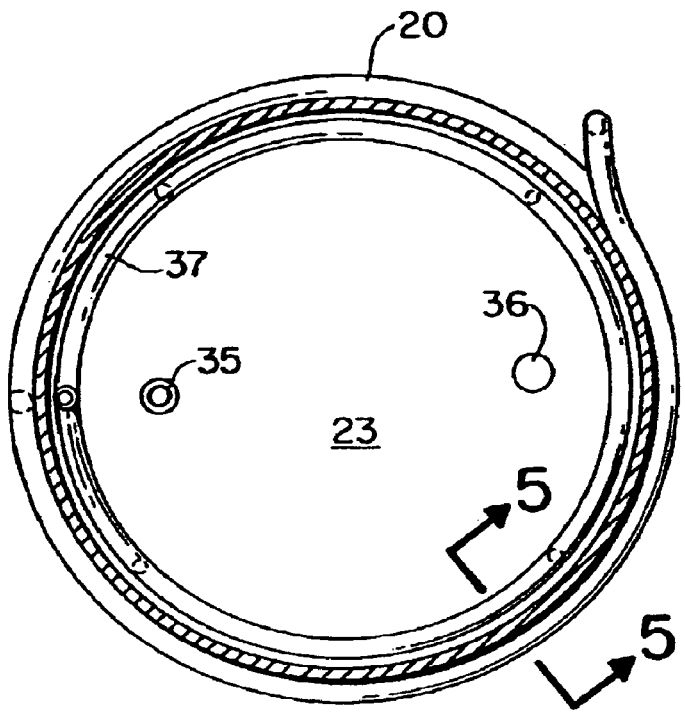
FIG. 4 is a fragmentary view of the preferred embodiment of the apparatus of the present invention illustrating the open reservoir and ozone diffuser.

After electricity is disconnected from compressor 29, transformer 51 and motor drive 53 are activated. The transformer 51 produces electricity with a very high voltage at ozone generator 50 for generating ozone within the confines of ozone generator housing 57. As this ozone is generated within housing 57, air is pumped with air pump 54 into inlet flow line 55 and via opening 56 into the interior of housing 57. HEPA filter 71 removes airborne microorganism before they can enter air pump 54 and flow line 55. This positive flow of air pressure into housing 57 causes a simultaneous discharge of air through fitting 39 into air flow line 38. The air flow line 38 then carries air to diffuser 37 or 37A (FIGS. 7-14) that is contained at the bottom at the side wall of reservoir 20. The specific placement of diffuser 37 or 37A and the flow of air therefrom containing ozone is shown more particularly in FIGS. 4-14. In FIG. 4, a top view of the reservoir shows that the diffuser 37 or 37A preferably extends 360 degrees about the periphery of reservoir 20 and at the sidewall 22 thereof. This is preferable because ozone bubbles 67 are used to scrub the side wall 22 at the inside surface as shown in FIG. 3.

Figure 6:
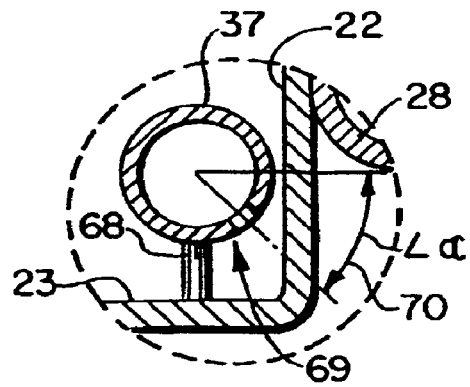
FIG. 6 is a fragmentary elevational view illustrating the ozone diffuser and its position in relation to the reservoir.
Figure 5:
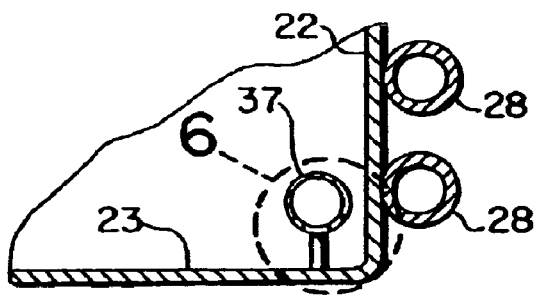
FIG. 5 is a sectional view taken along lines 5-5 of FIG. 4.

The diffuser 37 or 37A can be is supported by a plurality of feet 68 that extend between the diffuser 37 or 37A and a bottom wall 23 of reservoir 20. Openings 69 in diffuser 37 are directed at an angle with respect to the bottom wall 23 and side wall 22 of reservoir 20 as shown in FIG. 6. An angle 70 of preferably about 45 degrees defines the orientation of openings 69 with respect to the walls 22, 23. This configuration of the openings 69 relative to the walls 22, 23 ensures that bubbles 67 will be discharged outwardly toward side wall 22, to maximize the scrubbing effect at the interior wall 22 of reservoir 20. This scrubbing action using ozone bubbles 67 cleans the sidewall 22 and produces a rolling flow of water within reservoir 20. The bubbles 67 will strike the surface 25 of the reservoir 20 and flow inwardly. Such a circulation ensures that all of the water within the reservoir 20 is cleaned. Further, directing the bubbles from diffuser 37 outwardly toward wall 22 ensures that none of the bubbles 67 will enter bottle 18 via neck 19 which would cause the device to overflow.

FIGS. 7-14 show an alternate construction of the diffuser, wherein the diffuser is designated generally by the numeral 37A. Diffuser 37A has a porous body 72 as shown in FIG. 8 that begins with a cylindrically shaped hollow cross section. Porous body 72 can be a food grade porous ceramic material. The porous body 72 is generally C shaped as shown in FIG. 7, but provides the cross section shown in FIG. 11. FIGS. 8, 9 and 10 show the method of construction of the diffuser 37A which begins with porous body 72. In FIG. 8, porous body 72 has an inner surface 73 that surrounds hollow bore 75 and an outer surface 74. In FIG. 9, a non-porous coating (e.g. food grade non-porous epoxy that can be fired) is provided on porous body 72 to provide an outer coating 76 that is substantially impervious to the escape of air. In FIG. 10, rotary grinding tool 88 having rotary shaft 89 is used to grind away part of the non-porous coating 76 to provide an exposed face 90 (see FIGS. 10 and 11).

When air is injected through inlet elbow fitting 79, the air enters hollow bore 75 and then diffuses through porous body 72. Coating 76 prevents the escape of air so that air can only escape through exposed face 90. Exposed face 90 is positioned on the outer portion of C shaped diffuser 37A as shown in FIGS. 7 and 11. An enlarged view of this exposed face 90 is shown in FIG. 13 with arrows 91 indicating the escape of bubbles 92.

The inlet elbow fitting 79 has a body 80 with two legs 81, 82 extending therefrom. Coupling material 83 such as food grade epoxy can be used to join the combination of porous body 72 and its coating 76 to inlet elbow fitting 79. Each of the legs 81, 82 provides an internal hollow flow bore, said bores 84 and 85 intersecting at body 80 so that air flow can proceed from bore 84 of leg 81 to bore 85 of leg 82. The leg 81 can provide external threads 86 so that it can be connected to an influent air flow line 38. Other connectors could be used on leg 81 such as a stab fitting type connection, clamp connection or the like. Elbow fitting 79 at leg 82 can provide similar connective material for forming a connection with porous body 72 at its inner surface 73. This connective structure on leg 82 can be a stab fitting type connection as shown in FIG. 12, external threads, or like connective structure.

In FIG. 7, the diffuser 37A has closed end portion 78 and end portion 79 that receives elbow fitting 79. Closed end 78 can be closed by using the same material that constitutes coating 76 as shown in FIG. 14.

FIGS. 15-27 show an alternate and second embodiment of the apparatus of the present invention. The second embodiment provides a manually operable dispensing spigot 100 with a special switch arrangement that automatically activates an ozone generator such as the generator shown and described with respect to the preferred embodiment of FIGS. 1-14. It should be understood that the alternate embodiment of FIGS. 15-18 includes the spigot 100 as well as a cabinet 11, reservoir 20, and the various flow lines of the embodiments of FIGS. 1-14. In other words, in the alternate embodiment, spigot 100 replaces spigots 26, 27 of FIGS. 1-14. The spigot 100 triggers ozone generation and the transmission of ozone to the water contained within the reservoir. Ozone is also transmitted to a channel that connects the reservoir to the spigot, disinfecting water to be consumed.

In FIGS. 15-18, spigot 100 includes a spigot housing 101 to which is attached a handle 102 that enables a user to activate the handle 102 during the dispensing of water from the spigot 100.

Figure 18:
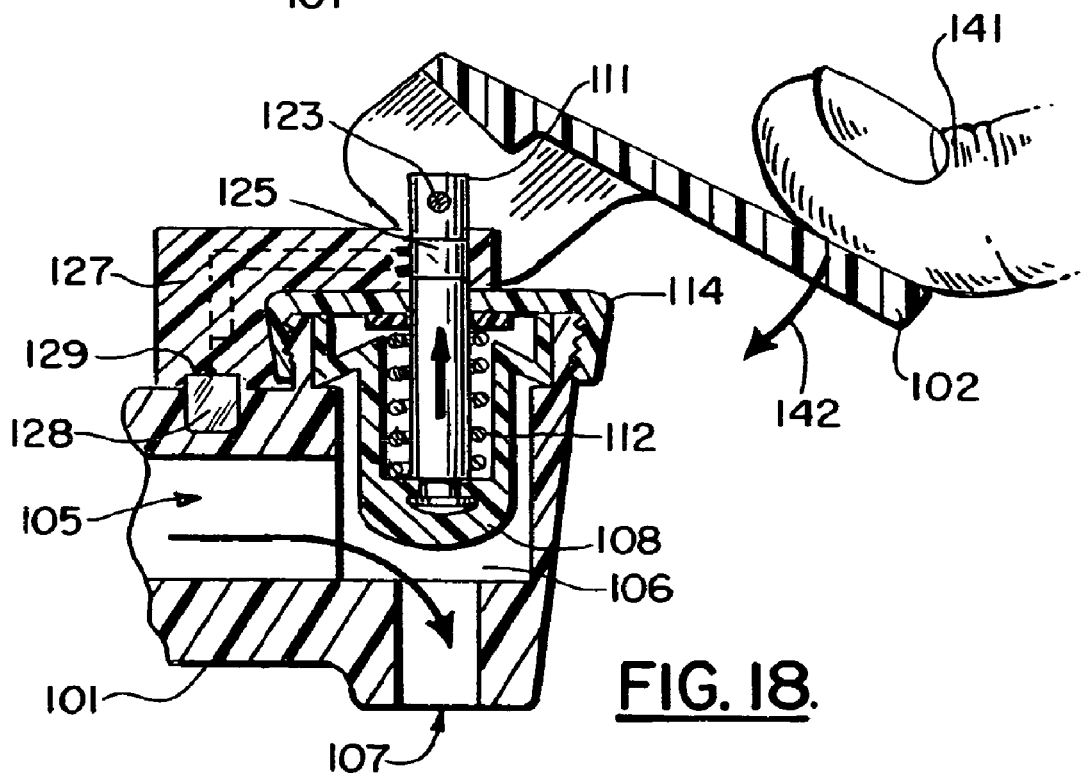
FIG. 18 is a partial sectional elevation view of the second embodiment of the apparatus of the present invention showing the spigot and valve in an opened position.

When the user 141 depresses the handle 102 to a dispensing, open valve position as shown in FIG. 18, not only is water dispensed into a container that the user is holding, but ozone is generated to sanitize an influent channel or horizontal bore 105 that communicates with flow outlet 107. The dispensing of ozone to horizontal bore 105 is in a very small concentration that is sufficient to disinfect water being dispensed, but not to generate an undesirable smell or taste.

Spigot 100 provides housing 101 that has an annular flange 103 that can engage the front surface of a cabinet such as the cabinet 11 that is shown and described with respect to the preferred embodiment of FIGS. 1-14. Flange 103 acts as a stop for the housing 101 after it is inserted at threaded portion 104 through an opening formed in the front surface of the cabinet 11. Threaded portion 104 enables a nut or other fastener to be threadably attached to the externally threaded section 104 for holding the spigot housing 101 to an opening in the front of the cabinet 11.

Water that is being dispensed from a reservoir of the cabinet 11 flows through a reservoir or flow channel that connects with horizontal bore 105. Vertical bore 106 extends from horizontal bore 105 to flow outlet 107.

Figure 17:
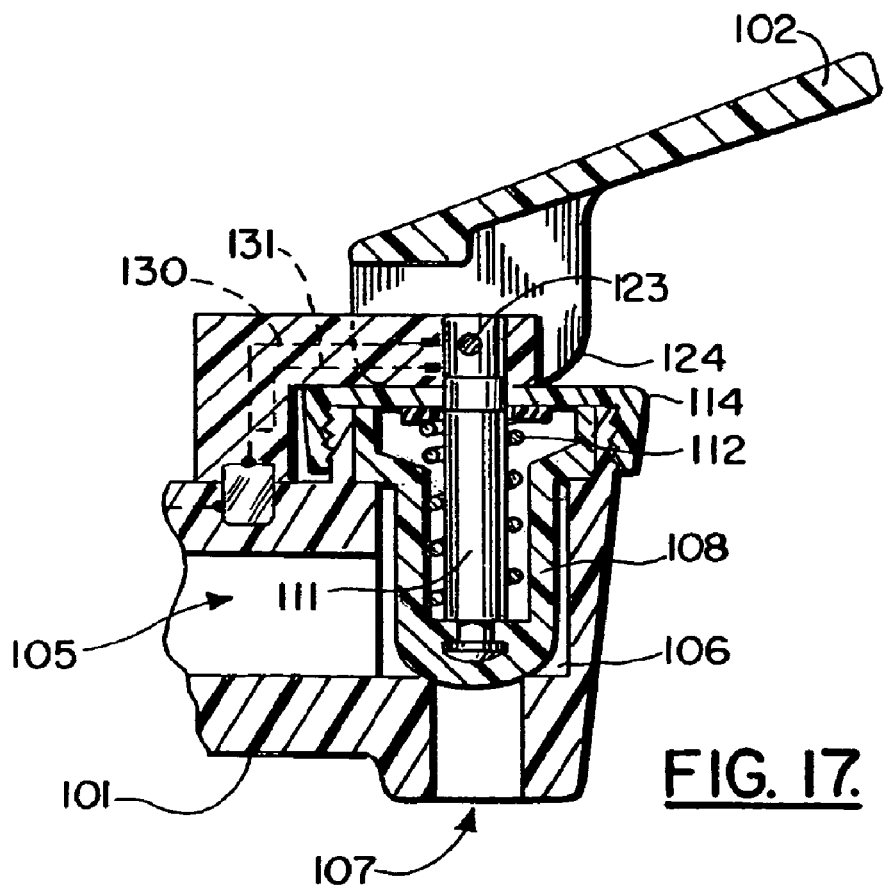
FIG. 17 is a partial sectional elevation view of the second embodiment of the apparatus of the present invention showing the spigot and valve in a closed position.

A valve body 108 is provided for opening and closing the flow outlet 107 as shown by the drawings in FIGS. 17 and 18. In FIG. 17, the flow outlet is closed. In FIG. 18, the flow outlet 107 is opened so that water can be dispensed. Valve body 108 (see FIG. 16) has an annular shoulder 109 and an operating rod socket 110. Operating rod 111 has an annular flange 119 that occupies socket 110 during use as shown in FIGS. 17 and 18. The operating rod 111 has an annular grove 120 that is provided in between a lower annular flange 119 and an upper annular flange 118. Basically, the annular shoulder 109 occupies annular groove 120 upon assembly.

Return spring 112 insures that the valve 108 will always return to a closed position when a user 141 is not depressing the handle 102. Rod 111 occupies socket 113 of valve body 108. A waterproof seal 132 is provided at the upper end portion of valve body 108. waterproof seal 132 engages cap 114 forming a water tight seal therewith.

Internal threads 115 of cap 114 engage external threads 116 on valve housing 101. Retainer 117 is provided for forming an attachment between cap 114 and dual contact barrel 127. A central opening 126 in cap 114 allows operating rod 111 to pass through cap 114. Similarly, a vertical, generally cylindrically shaped passageway 140 is provided on dual contact barrel 127 enabling operating rod 111 to pass through it. The upper end portion of operating rod 111 provides a transverse opening 122 that can align with the transverse opening 121 on handle 102. A pin 123 forms a connection between handle 102 at opening 121 and operating rod 111 at opening 122 as shown in FIGS. 16-18.

Handle 102 provides a cam surface 124 that lifts operating rod 111 when the handle 102 is pushed downwardly by a user 141 as illustrated in FIG. 107 by arrow 142. A metallic collar 125 is provided at the upper end portion of operating rod 111 as shown in FIG. 16. The collar 125 is part of a switch arrangement for activating the ozone generator when the handle 102 is depressed to the position shown in FIG. 18. The collar 125 contacts electrical lines 130, 131 of dual contact barrel 127. The metallic collar 125 closes a circuit to activate an ozone generator and blower when it contacts both of the electrical lines 130, 131 as seen in FIG. 18.

A receptacle 128 on valve housing 101 receives plug 129 of dual contact barrel 127. Electrical lines 138, 139 on valve body 101 communicate with socket 128 and thus plug 129 as shown in FIG. 18. Electrical lines 138, 139 are connected to the ozone generator and blower that are shown and described with respect to the preferred embodiment of FIGS. 1-14. When the handle 102 is depressed to the position shown in FIG. 18, the ozone generator and air pump are simultaneously activated so that ozone flows in flow tube 136 to ozone supply fitting 133 that is positioned in horizontal bore 105 of housing 101. Alternatively, the ozone generator and air pump can be activated by a timer that is activated when handle 102 is depressed. The ozone supply fitting 133 has a bore 137 and diffuser 134 that dispensing ozone to water that is contained in the bore 105. A barbed connector 135 can be provided for enabling a connection to be made between tubing 136 that supplies ozone and fitting 133.

Figure 19:
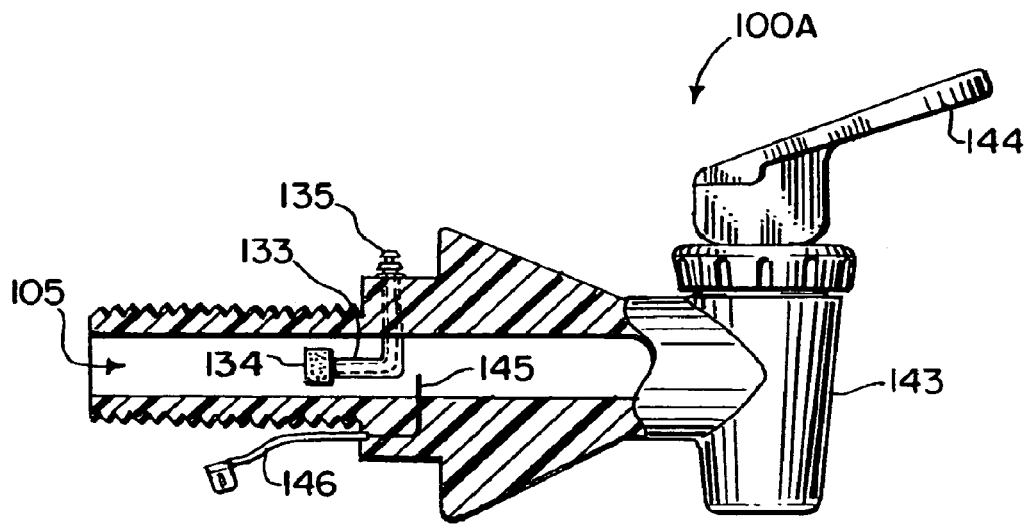
FIG. 19 is a partial, cut away, elevation view of the second embodiment of the apparatus of the present invention illustrating the spigot with a flow meter switch.
Figure 20:
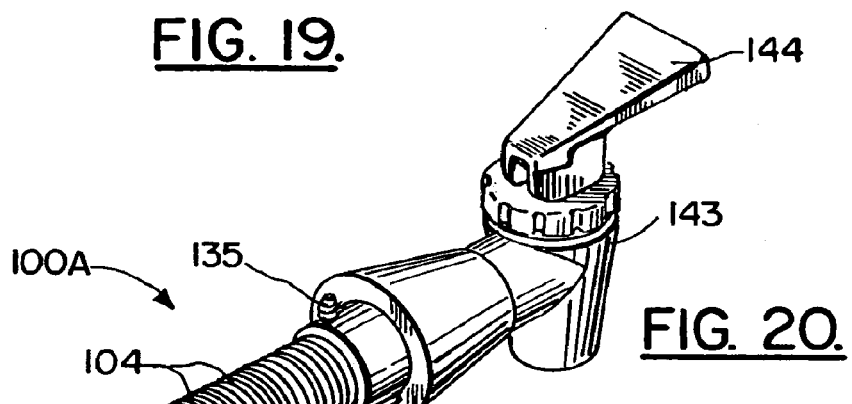
FIG. 20 is a partial perspective view of the second embodiment of the apparatus of the present invention illustrating the spigot of FIG. 19.
Figure 21:
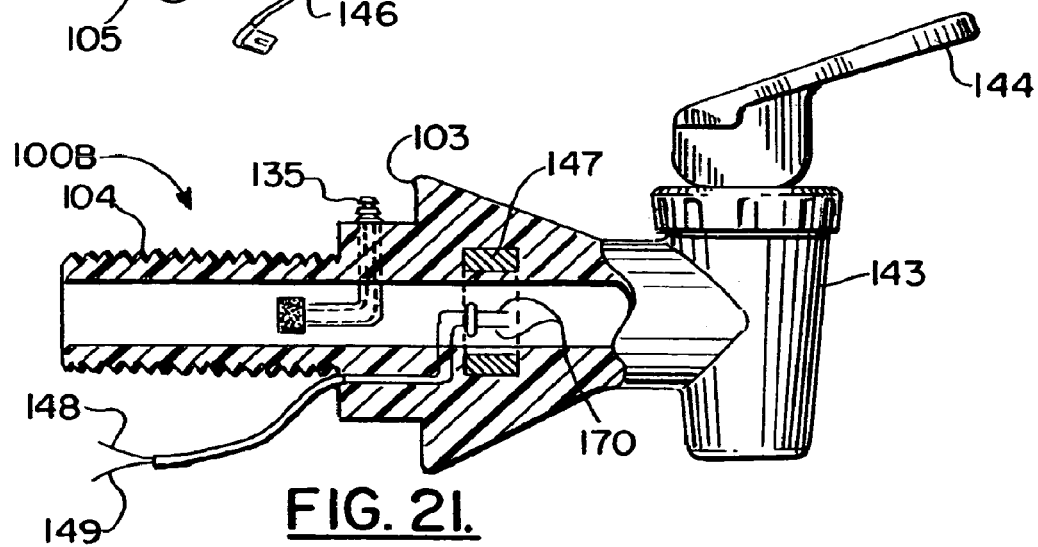
FIG. 21 is a partially cut away elevation view showing an alternate construction for the spigot that is a part of the second embodiment of the apparatus of the present invention.
Figure 22:
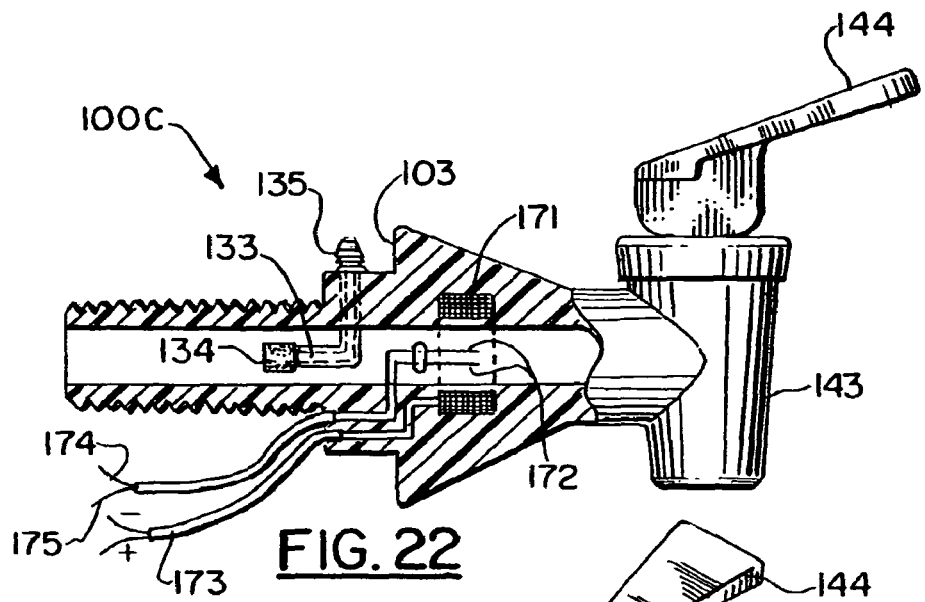
FIG. 22 is a partially cut away elevation view showing alternate construction for the spigot that is a part of the second embodiment of the apparatus of the present invention.
Figure 23:
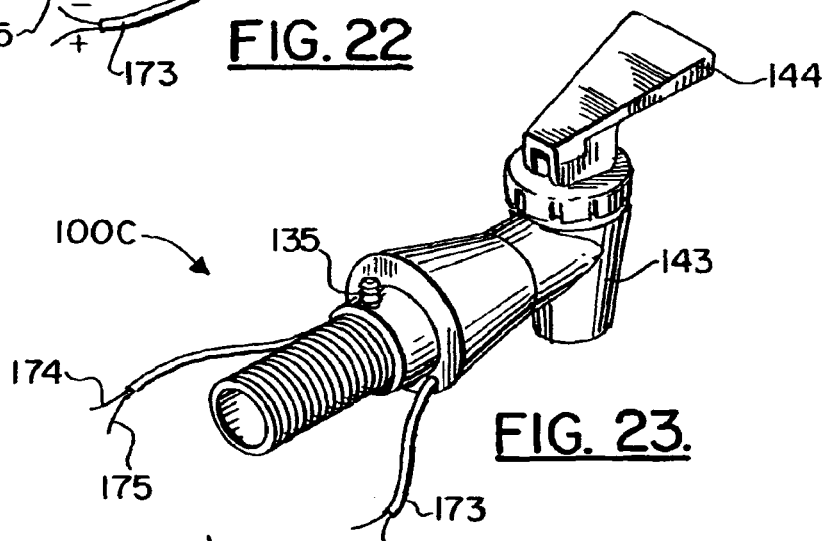
FIG. 23 is a partial perspective view showing the spigot of FIG. 22.
Figure 24:
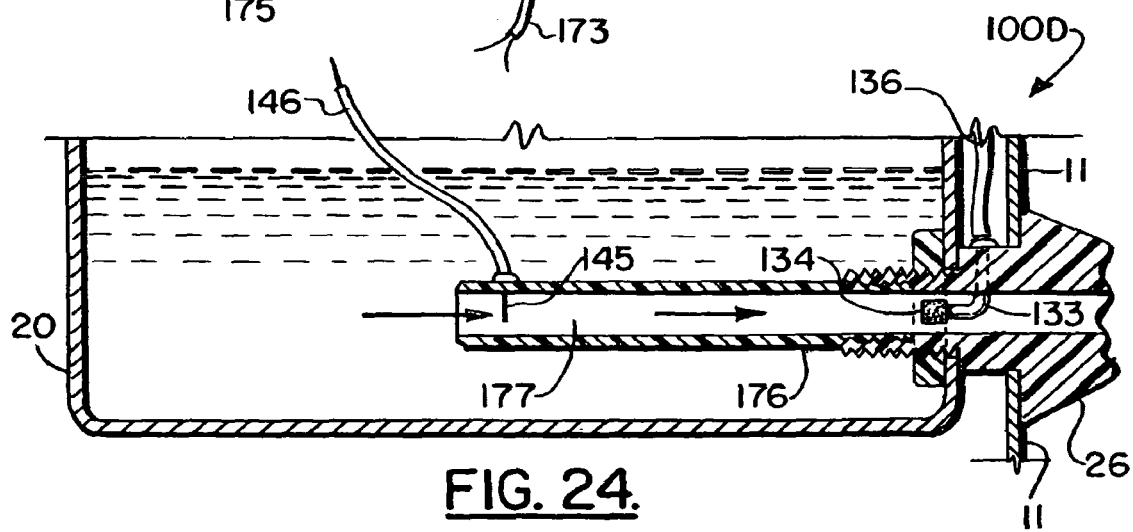
FIG. 24 is a partial sectional, elevation view of the second embodiment of the apparatus of the present invention showing an alternate spigot construction.
Figure 25:
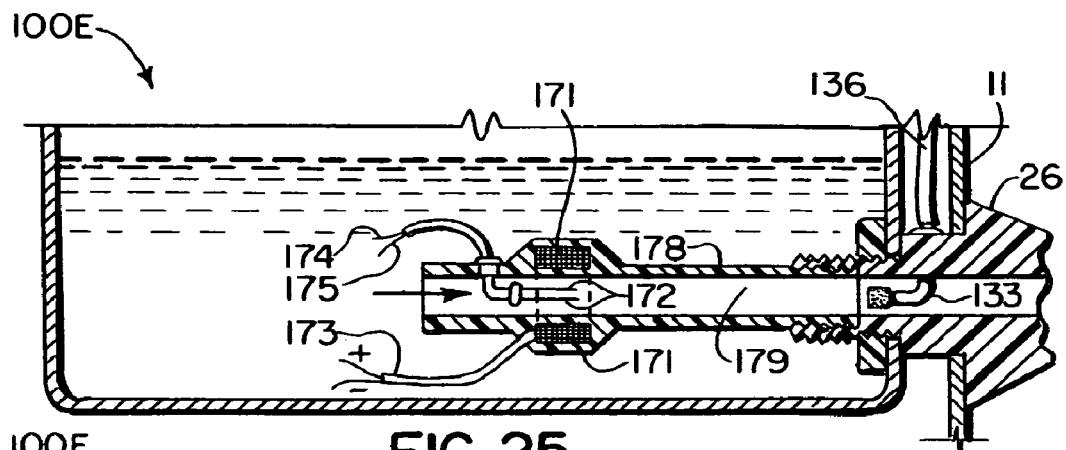
FIG. 25 is a partial sectional, elevation view of the second embodiment of the apparatus of the present invention showing an alternate spigot construction.
Figure 26:
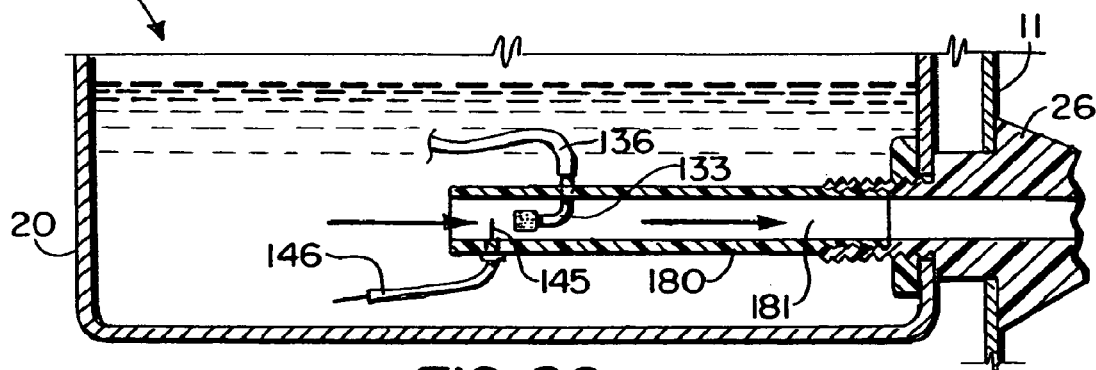
FIG. 26 is a partial sectional, elevation view of the second embodiment of the apparatus of the present invention showing an alternate spigot construction.
Figure 27:
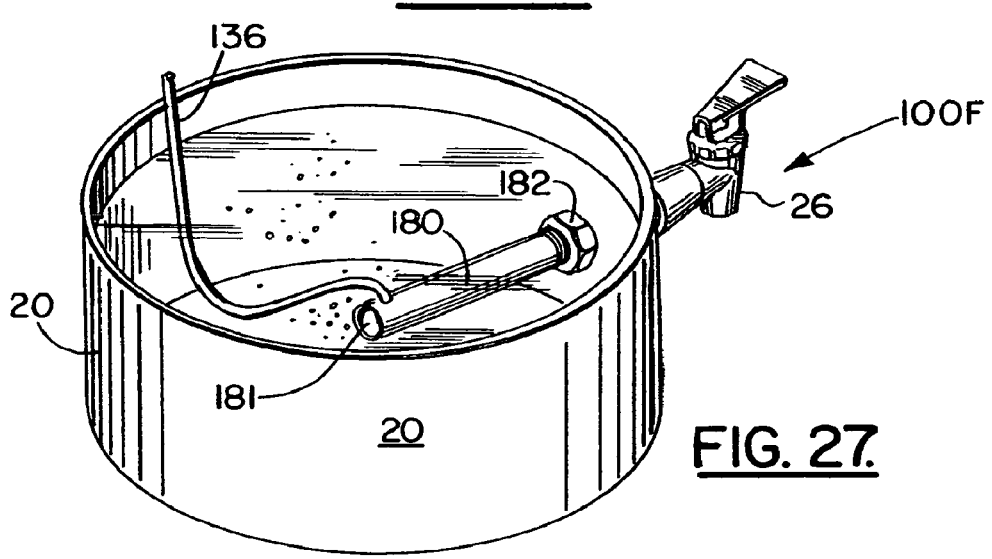
FIG. 27 is a partial perspective view of the second embodiment of the apparatus of the present invention.

In FIGS. 19-27, alternate constructions for the spigot are disclosed, designated by the numeral 100A in FIGS. 19-20; 100B in FIG. 21; 100C in FIGS. 22-23; 100D in FIG. 24; 100E in FIG. 25; and 100F in FIGS. 26-27. Spigot 100A in FIGS. 19-20 is similar to a commercially available spigot such as spigot 26 or 27. In FIG. 19, spigot 100A has a body 143, handle 144 and a flow sensor 145 that activates the ozone generator and air pump responsive to water flow that is sensed by flow sensor 145. Water flow is sensed by flow sensor 145 when spigot 100A is opened by depression of valve handle 144 and water flows in channel 105. Instrumentation line 146 activates the ozone generator and blower when valve handle 144 is depressed and flow is sensed. A flow sensor 145 and its instrumentation line 146 are commercially available. Such a sensor 145 and instrumentation 146 can be used to activate the blower and ozone generator of FIGS. 1-14.

In FIG. 21, spigot 100B has magnetic flow sensor with magnet 147 and sensors 170. In FIGS. 22, 23 spigot 100C provides a flow meter that can be an electromagnet type flow sensor with instrumentation lines 148, 149. In FIG. 22, an electrical supply 173 powers electromagnet 171 with flow sensors 172. Such an electromagnet flow sensor 171, 172 is available commercially. Instrumentation lines 174, 175 enable the flow sensor 171, 172 to operate the ozone generator and blower of FIGS. 1-14.

In FIGS. 24-27 a spigot 100D can include a conventional spigot body 26 provided with an extension tube. In FIG. 24, flow sensor 145 is mounted to extension tube 176 having flow bore 177. The extension tube 177 can be glued or threadably connected to a standard, commercially available spigot 26 or 27. Flow line 136 carrying ozone from the ozone generator of FIGS. 1-14 communicates with fitting 133 mounted directly to the conventional spigot 26. Diffuser 134 dispenses ozone to bore 177 upstream of spigot 26. The spigot apparatus 100D of FIG. 24 is use to activate the ozone generator and blower of FIGS. 1-14 when flow is sensed by flow sensor 145 and instrumentation line 146.

The spigot 100E of FIG. 25 includes extension tube 178 with bore 179. Electromagnet flow sensor 172 having electromagnet 171 powered by electricity via line 173 is mounted to tube 179. Sensor 172 communicates with and activates the ozone generator and blower of FIGS. 1-14 via instrumentation lines 174, 175. The tube 178 having bore 179 can be glued or threadably attached to a standard spigot 26 (see FIG. 25).

In FIGS. 26, 27 Spigot 100F has tube 180 with bore 181. Both flow sensor 145 and diffuser 134 with fitting 133 are mounted to tube 180. Tube 180 can be glued, threadably attached or otherwise connected to spigot 26. Nut 182 can secure spigot 100F to cabinet 111 and reservoir 20.

Figure 28:
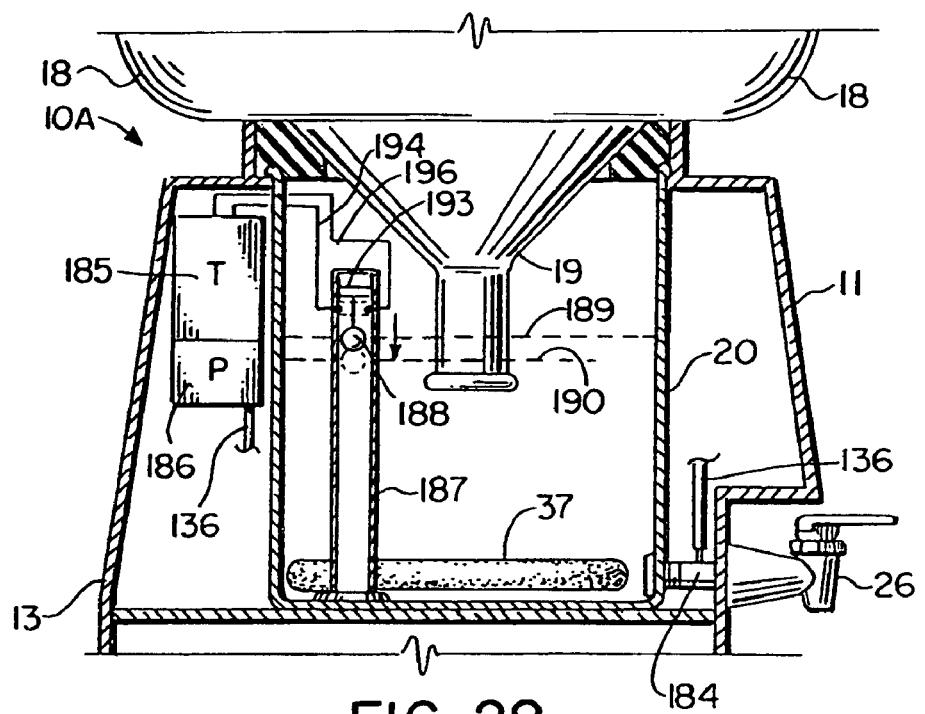
FIG. 28 is a sectional elevation view of the second embodiment of the apparatus of the present invention.

FIG. 28 is a sectional, elevation view of an alternate embodiment of the apparatus of the present invention, designated generally by the numeral 10A. In FIG. 10A, ozone is generated for sanitation of water responsive to operation of the spigot. In FIG. 10A, the ozone generator is not shown but is connected to pump P 186 that is activated using timer 185. The ozone generator of the preferred embodiment of FIGS. 1-14 could be used in combination with FIG. 28, generating ozone that is pumped using pump 186 and transmitting that ozone to diffuser 37 via flow line 136. Flow line 136 can also be transmitted to an extension tube 184 that is connected to a conventional spigot 26. As shown in FIG. 28, the extension tube 28 can extend between spigot 26 and reservoir 20. In FIG. 28, an inverted bottle type water cooler is shown having a cabinet 11 with an opening at the top as shown and described with the previous drawings of FIGS. 1-14. An inverted bottle 18 has a neck 19 that extends into reservoir 20. When the spigot 26 is activated to dispense water, the water level drops from a first water level 89 to a lower water level 90. This causes the float 188 to drop and wherein the contact 193 on the float 188 closes a circuit with the two electrical lines 194, 196. When this occurs, the timer activates the pump 186 and ozone generator for pumping ozone to either or both of diffuser 137 and extension 184. Thus, ozone is generated responsive to inactivation of the spigot 26 by a user that depresses the handle part of the spigot.

Figure 29:
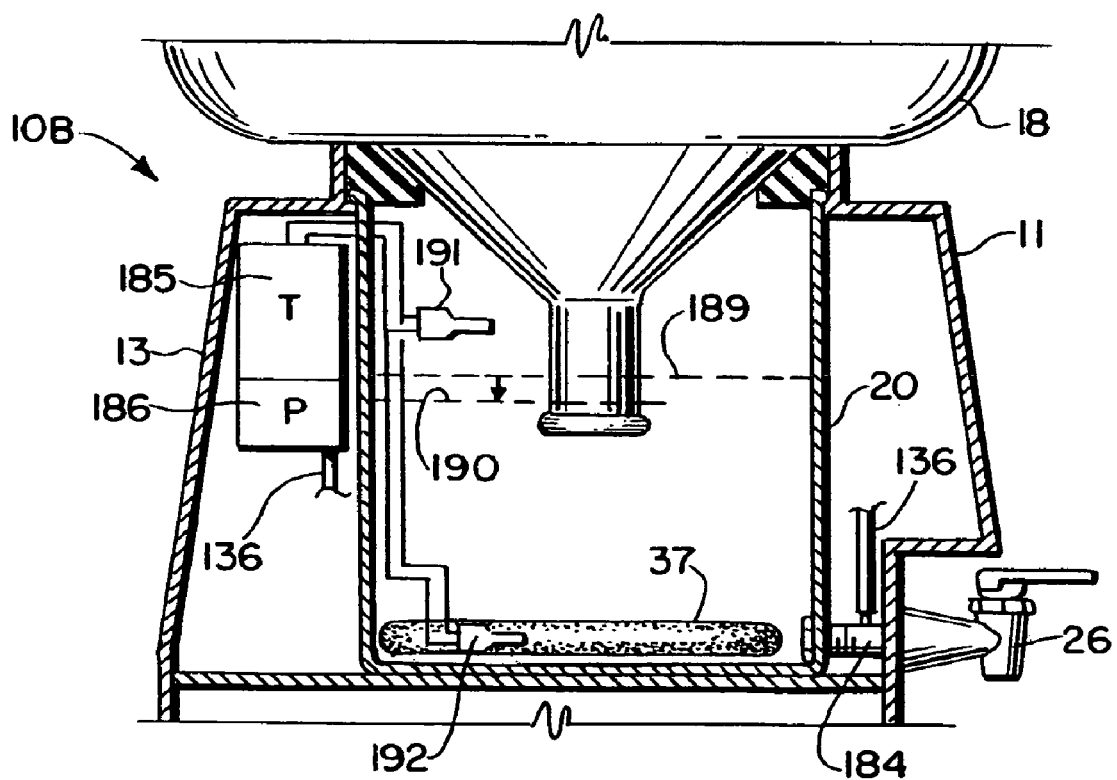
FIG. 29 is another sectional elevation view of the second embodiment of the apparatus of the present invention, used in combination with an air pressure switch.

In FIG. 29, an additional embodiment is designated by the numeral 10B. In FIG. 29, the upper end 13 of cabinet 11 is provided with a timer 185 and pump 186. The pump 186 pumps ozone that has been generated using an ozone generator as shown and described in FIGS. 1-14 or in FIGS. 30-34, 36. In FIG. 29, pressure controllers 191, 192 are provided. As the water level drops from level 189 to level 190, either one or both of the sensors 191, 192 can be used to monitor the change in pressure for activating the timer 185 and pump 186 via instrumentation lines 197, 198. As with the embodiment of FIG. 28, the water level drops from level 189 to level 190 when the spigot 26 is operated by depressing the handle. Thus, ozone is generated to reservoir 20 using diffuser 37 and/or to extension 184 using flow line 136. In this fashion, ozone is generated responsive to activation of the spigot 26.

Figure 30:
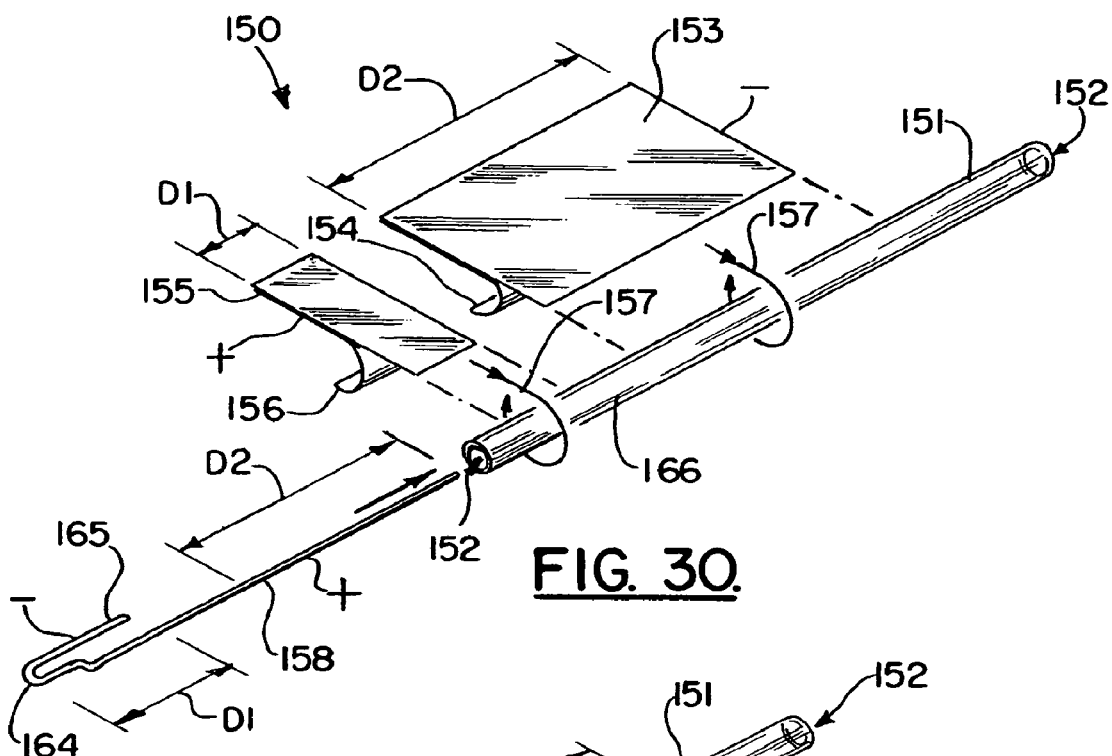
FIG. 30 is a perspective view of an alternate ozone generator construction that can be used with any of the embodiments of FIGS. 1-29.

FIGS. 30-35 show an alternate embodiment of the apparatus of the present invention, designated generally by the numeral 150 in FIGS. 30, 31, 32, 33, 35. The ozone generator or ozone discharge tube 150 of FIGS. 30-35 features a dielectric tubing 151 that can be, for example, a Corning® or Pyrex® cylindrically shaped glass tube having a central longitudinal bore 152. A pair of foil adhesive layers are applied to the external surface 166 of the tube 151. These layers include foil adhesive tape layer 153 and foil adhesive layer 155. Each of these layers can be in the form of adhesive tape having release liners. In FIG. 30, the foil adhesive tape section 153 has release liner 154. The smaller foil adhesive tape section 155 has release liner 156.

Figure 31:
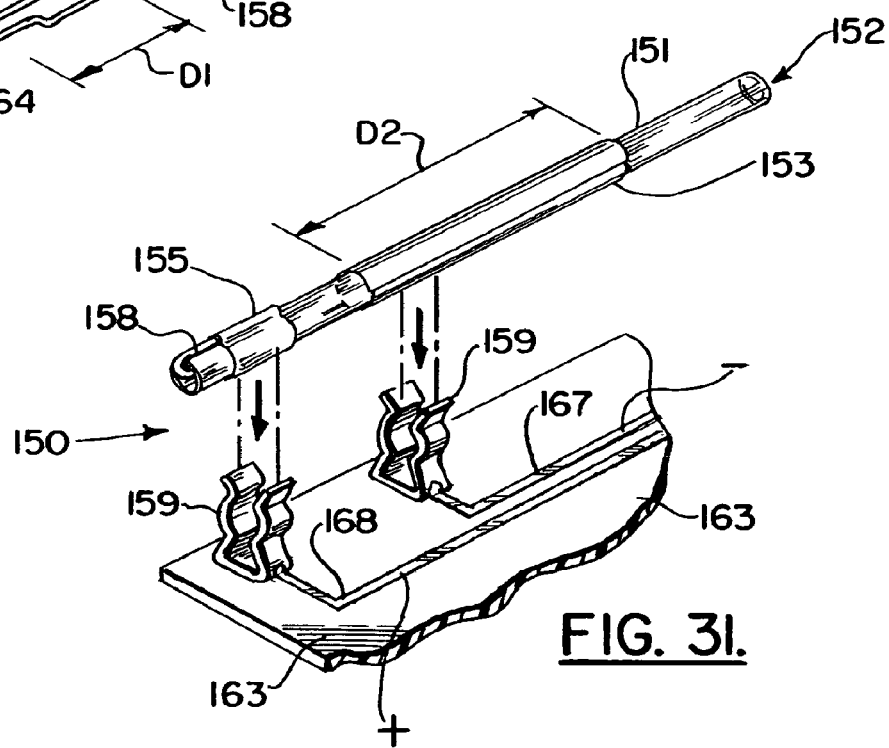
FIG. 31 is a partial perspective view of the ozone generator of FIG. 30.

Arrows 157 in FIG. 30 schematically illustrate the application of each of the foil adhesive tape sections 153, 155 to the external surface of tubing 151. Electrode 158 is placed inside of tubing 151, occupying a part of bore 152. One end portion of electrode 158 provides a clamp 164 that attaches to an end of tubing 151. An exposed portion 165 of electrode 158 is placed on the outer surface 156 of tubing 151. The foil adhesive tape section 153 is preferably of a size and shape that enables it to communicate with and cover the exposed part 165 as shown in FIGS. 30 and 31.

In FIG. 30, the exposed part 165 and foil adhesive tap section 155 are each of a width "D1" as shown. The foil adhesive tape section 153 is spaced from the foil adhesive tape section 155 and is of a size and shape to encircle the tubing 151 and to extend a length along the tubing 151 as seen in FIG. 1 that is partially filled with electrode 158. Arrows "D2" in FIGS. 30-31 show the width of sheet 153 and the part of electrode 158 that aligns with sheet 153 after placement of electrode 158 in bore 152 of tube 151. A pair of metallic spring clips 159 communicate with electrical leads 167, 168 that are mounted upon circuit board 169. In this fashion, the circuit board can provide a timing circuitry that is in electrical communication with an ozone power circuit and air blower (pump) for operating discharge tube 150 via clamps 159 and leads 168. A simple timing circuit activates the ozone generator 150 pump or air blower for a selected time interval. At about the same time, the blower 169 can be activated by the timing circuit. The timing circuit shuts off generator 150 and blower 169 after they operate for a desired time interval.

Figure 32:
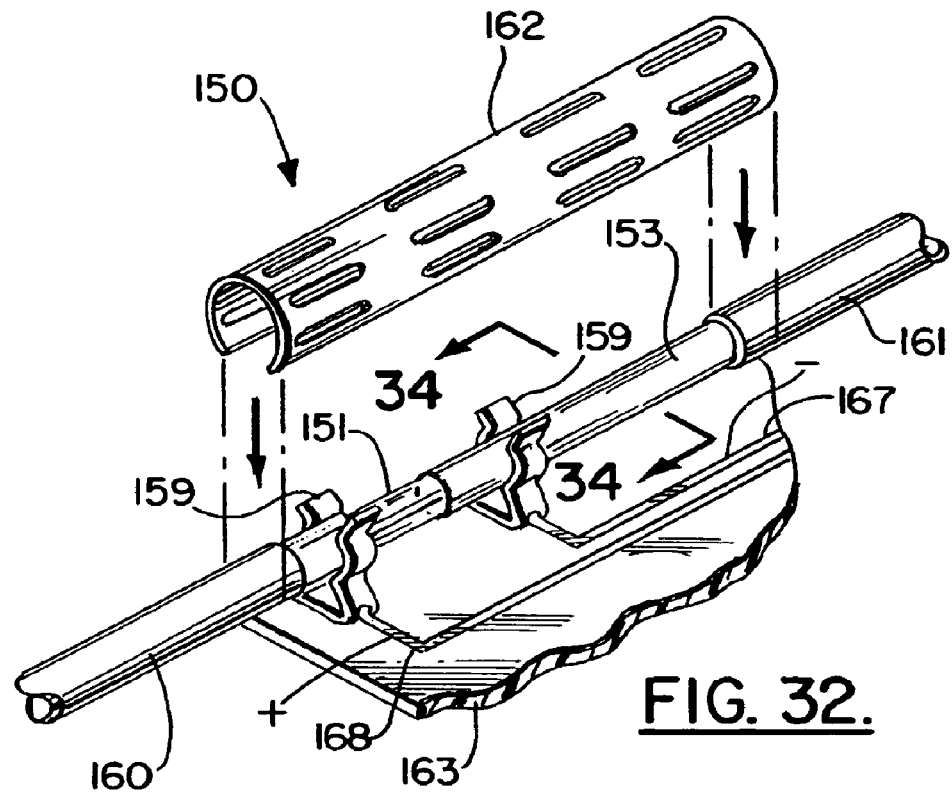
FIG. 32 is a perspective view of the ozone generator of FIGS. 30-31.
Figure 33:
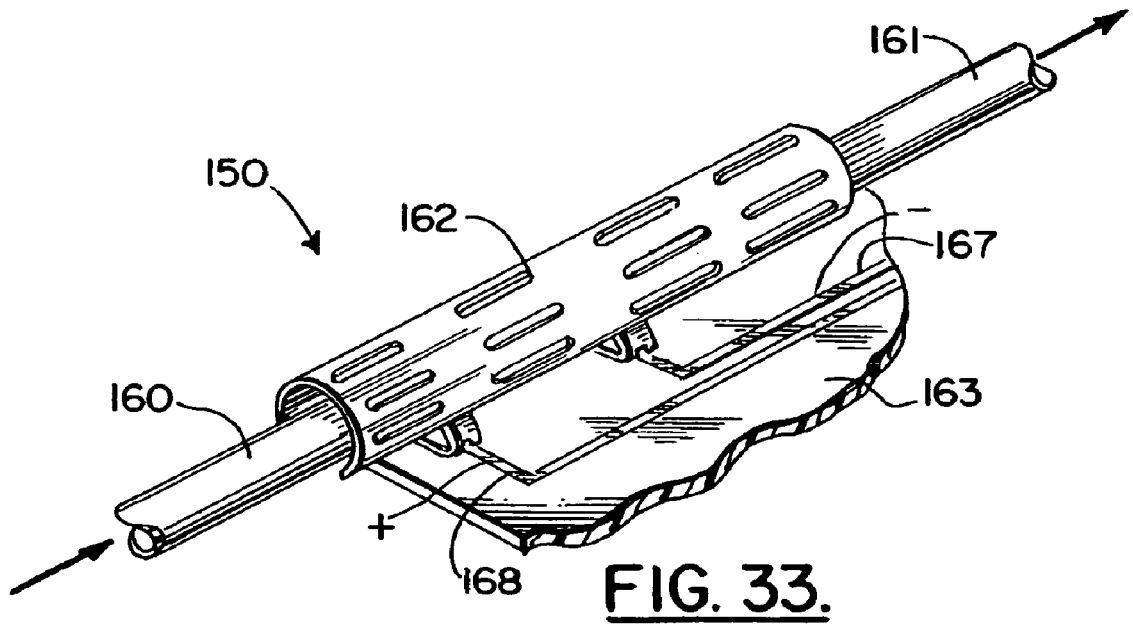
FIG. 33 is a perspective view of the ozone generator of FIGS. 30-32.
Figure 34:
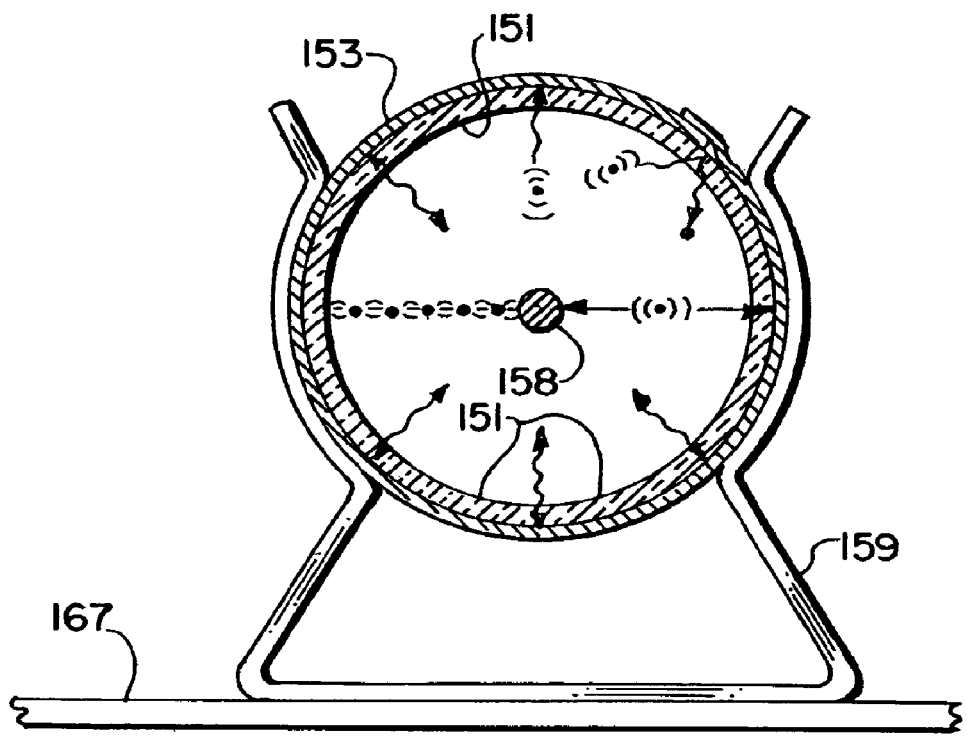
FIG. 34 is a sectional view taken along lines 34-34 of FIG. 32.
Figure 35:
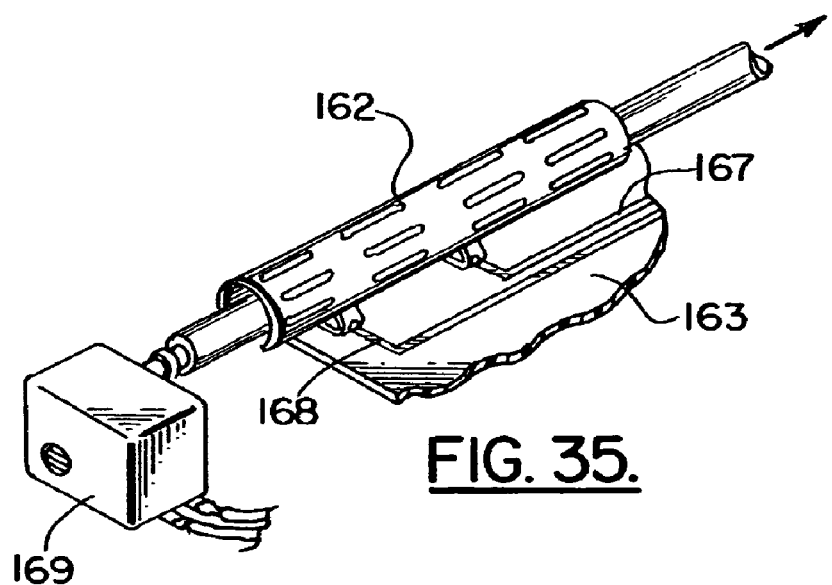
FIG. 35 is a perspective view of the improved ozone generator of FIGS. 30-34.

A flow conduit 160 is attached to an end portion of tubing 151 as shown in FIG. 32. Similarly, a discharge conduit 161 is mounted to an end portion of tubing 151 that is opposite the conduit 160. Upon assembly, the glass tubing 151 can be covered and protected by safety cover 162. An air pump 169 can be connected to the conduit 160 for driving air through the bore 152 of tubing 151. In FIG. 34, the negatively polarity (−) foil 153 acts as a reflector tube to concentrate far UV ozone at the central longitudinal axis of tubing 151 and next to electrode 158, thus increasing output. This differs from prior art arrangements wherein far UV is not reflected and concentrated but dissipates. The ozone generator 150 can be used in place of ozone generator 50 of any embodiment of FIGS. 1-16 or as the ozone generator for the embodiments shown in FIGS. 17-29.

In FIG. 34, the (−) polarity foil electrode reflector tube acts as a cylindrical mirror for concentrating oxygen cleaving range far UV at the central longitudinal axis of tubing 151 at the (+) polarity electrode 158. Far UV, being above the primary heat producing range does not contribute significantly to process air heating. The bulk of the dielectric resistance heating is absorbed by the low mass-high surface area thin radiator material (−) polarity external foil electrode and radially transferred to ambient air outside the tube. By this process, the ozone discharge tube runs cool and does not contribute to ozone degradation. This differs from some prior art arrangements of wherein far UV ionizing radiation is not reflected and concentrated by dissipates.

FIGS. 36-47 show various constructions of diffuser designs that can be used with any embodiment shown in FIGS. 1-35 of the method and apparatus of the present invention.

Figure 36:
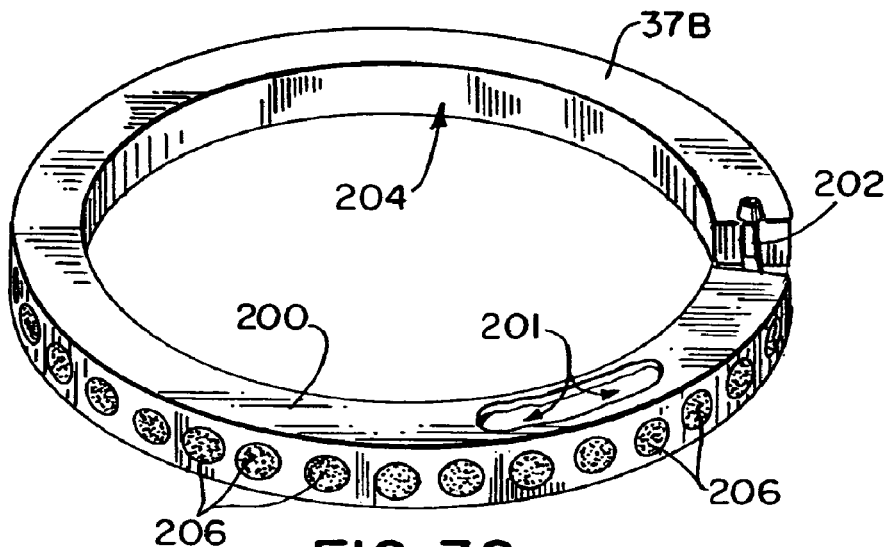
FIG. 36 is a partial perspective view of a third embodiment of the apparatus of the present invention, showing an improved diffuser.
Figure 37:
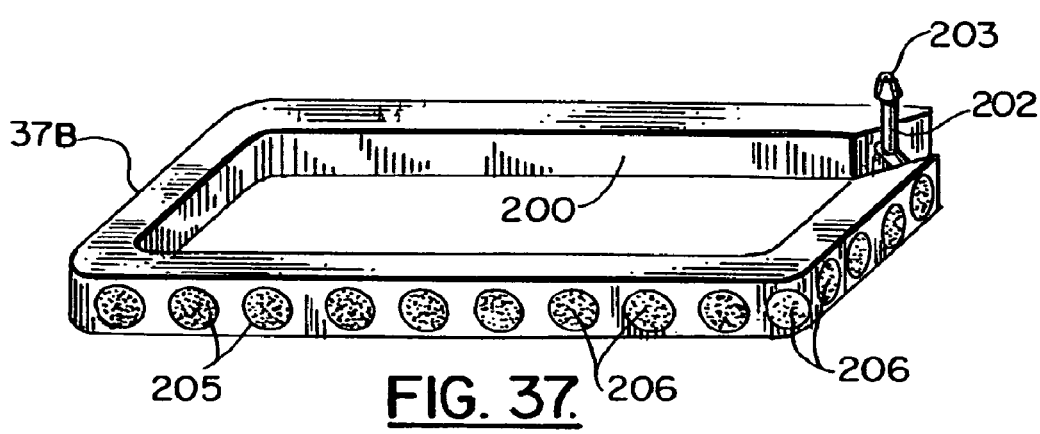
FIG. 37 is a partial perspective view of a third embodiment of the apparatus of the present invention showing an improved diffuser in a rectangular configuration.
Figure 37A:
FIGS. 37A-37C are top, side and bottom views respectively showing an individual diffuser element used with the diffuser of FIGS. 36-37.
Figure 37D:
FIGS. 37D-37F are top, side and bottom views of another configuration for a diffuser element used with the diffuser of FIGS. 36-37
Figure 37B:
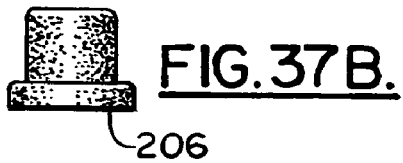
Figure 37E:
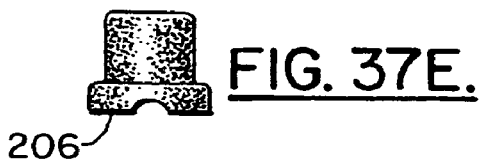
Figure 37C:
Figure 37F:

In FIG. 36, diffuser 37B is shown in perspective view. Diffuser 37B is shown in a circular pattern, but can also have the rectangular pattern shown in FIG. 37. Diffuser 37B shows a silicone tube 200 that has a hollow bore 201 for conveying air. Fitting 202 includes a connector 203 that enables air to be piped from the ozone generator of any of the embodiments shown in FIGS. 1-35 to the bore 201 of silicone tube 200. The silicone tube 200 has a wall 204 that surrounds bore 201. Wall 204 has a plurality of openings 205, each opening 205 having a diffuser insert 206 (see FIGS. 37A-37F). The inserts 206 are diffuser material such as for example, diffuser stone insert material. Diffusers 206 can be of food grade sintered metal (e.g., aluminum, stainless sheet). The insert material 206 can be as selected for any of the inserts 205 shown in FIG. 37A.

FIGS. 38-40 show another diffuser 37C in perspective views. For the embodiment shown in FIGS. 38-40, the diffuser 37C can include modules 213 connected with stab fittings 214 with an additional fitting 215 connecting modules 213 together in a circle. Fitting 215 provides an inlet 216 for piping that communicates between the ozone generator and the diffuser 37C. A blade 217 in FIG. 44 illustrates that any one of the modules 213 can be cut to a selected length.

Diffuser 37C is comprised of modules 213 connected end to end. A single module 213 is shown in FIGS. 38-29. Module 213 can be a two piece molding (FIG. 38) or a one piece molding (FIG. 39). Each module 213 includes tube 207 having flow bore 212. In FIG. 38, bore 212 can be formed by providing matching longitudinal slots, each semicircular in traverse cross section that align upon assembly of an upper section 210 and lower section 211. Diffuser sockets 209 receive inserts 206 that can be food grade sintered metal, stone, or any of the materials shown in any of the embodiments of figures disclosed herein. Sockets 209 can be surrounded by cylindrically shaped wall portions 208.

Figure 41:
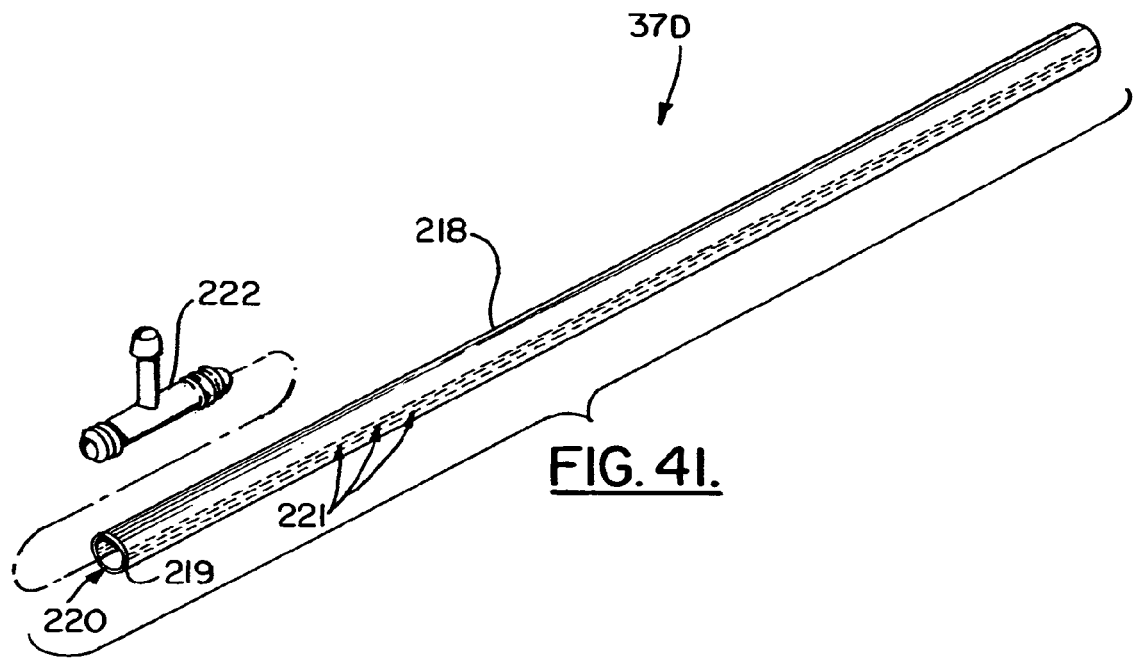
FIG. 41 is a partial elevation view of a fourth embodiment of the apparatus of the present invention showing an improved diffuser.
Figure 42:
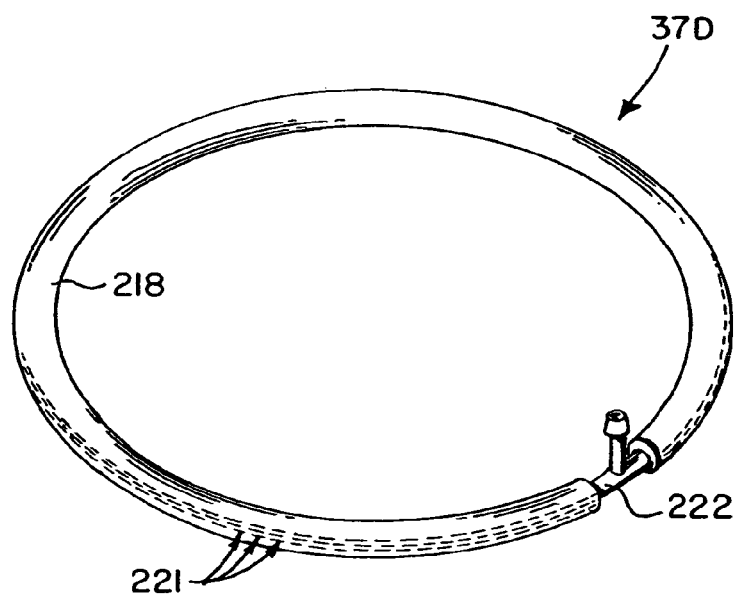
FIG. 42 is a partial perspective view the diffuser of FIG. 41.

FIGS. 41-42 show an additional diffuser 37d. Diffuser 37d includes an elongated cylindrically shaped tube 207 having a cylindrical wall 219 that surrounds hollow bore 220. Tube 218 wall 219 is provided with a plurality of small diffuser slots 221 through which ozone can exit the tubal bore 220. Barb connector 222 is a T-shaped fitting that is attached to opposing end portions of tube 218 to form a circular diffuser as shown in FIG. 42, and leaving one portion of the barb connector 222 as an inlet opening through which ozone can be transmitted to the fitting 222, to bore 220 and then through diffuser slots 221 to the surrounding reservoir 20.

Figure 43:
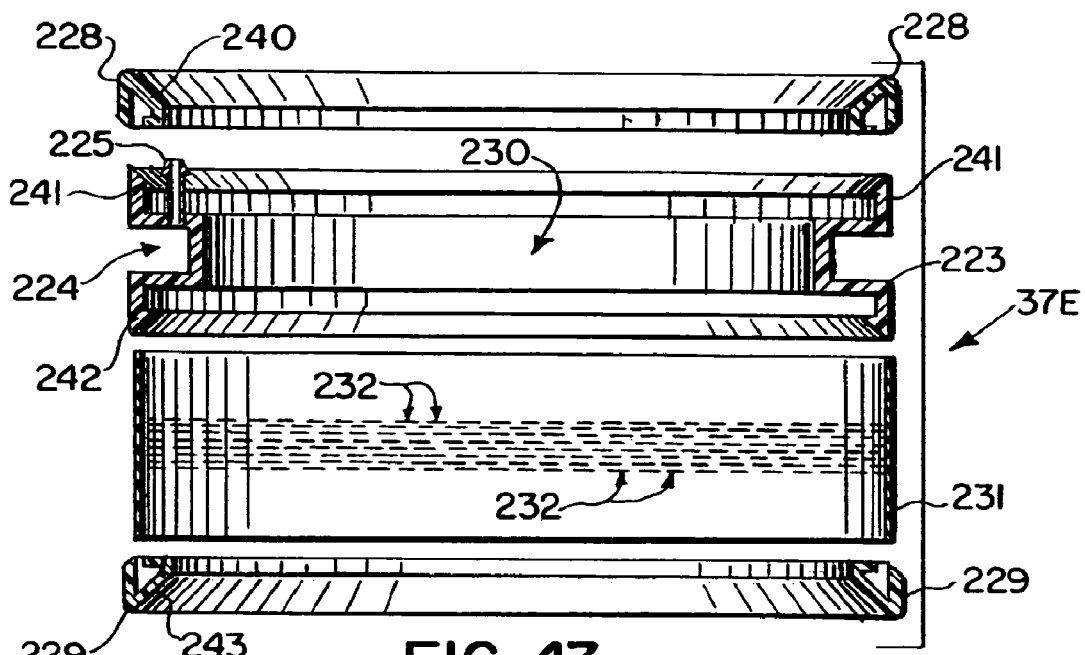
FIG. 43 is an exploded elevation view of a fifth embodiment of the apparatus of the present invention illustrating an improved diffuser.
Figure 44:
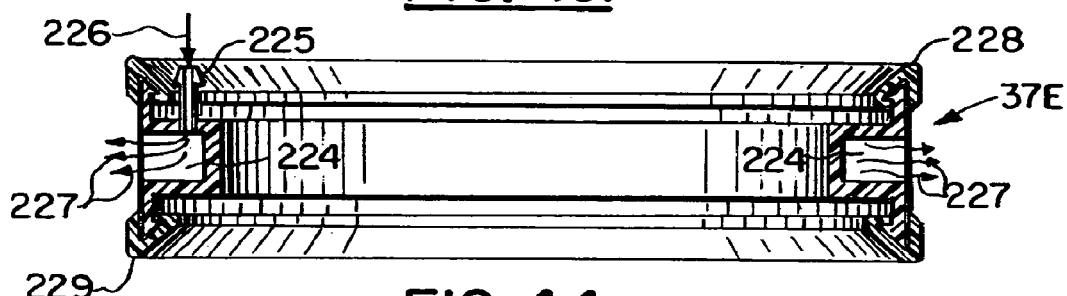
FIG. 44 is a sectional view of the diffusers of FIG. 44.
Figure 45:
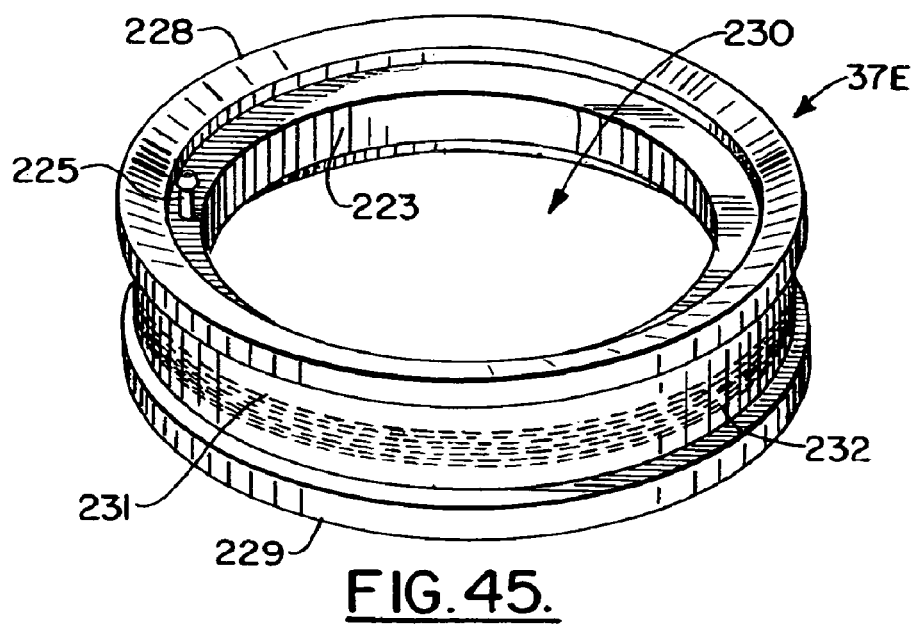
FIG. 45 is a perspective view of another diffuse for use with the present invention.

Another embodiment of a diffuser is shown in FIGS. 43-45, designated generally by the numeral 37E. Diffuser 37E includes an angular body 223 having an outwardly facing angular flow channel 224. The angular flow channel 224 is covered with an angular membrane or sheet 231 that is a thin wall membrane structure that includes a plurality of small slotted openings 232, each extending through the angular membrane sheet 231. The angular membrane sheet 231 can be of any selected ozone resistant material such as food grade silicone, EPDM rubber, Viton or the like.

Angular flow channel 224 is provided with an inlet fitting 225 through which ozone can be transmitted in the direction of arrow 226. Arrows 227 schematically illustrate the discharge of ozone from flow channel 224 through slots 232 of angular sheet 231 and then to the surrounding reservoir 20 for ozonating water contained within the reservoir 20.

Correspondingly shaped interlocking angular sections can be provided for attaching an upper retainer ring 228 and a lower retaining ring 229 to body 223 and form holding membrane sheet 231 in position. The upper retaining ring 228 provides interlocking angular section 240 that forms an interlocking connection with the angular interlocking section 241 of body 223. Similarly, the interlocking angular section 242 on body 223 forms an interlocking connection with the interlocking angular section 243 of a lower retainer ring 229, the assembly of the upper and lower retaining rings 228, 229 with body 223 being shown in FIGS. 44-45.

The completed diffuser 37E has a central opening 230. The slotted openings 232 and angular sheet 231 face away from central opening 230 so that ozone exiting slotted openings 232 can travel in the direction of arrows 227 for scrubbing the sidewall of a generally cylindrically shaped reservoir, as with the embodiments of FIGS. 1-14. In this fashion, the slotted opening 232 can be placed very close to the reservoir 20 sidewall 22 so that ozone bubbles exiting the openings 232 can scrub the sidewall 22 of the reservoir 20 and sanitize it. In keeping with the teachings of the present invention, the diffuser 37E shown in FIGS. 43-45 can be square or rectangular in order to more closely fit the shape of a square or rectangular reservoir if desired.

Figure 43A:
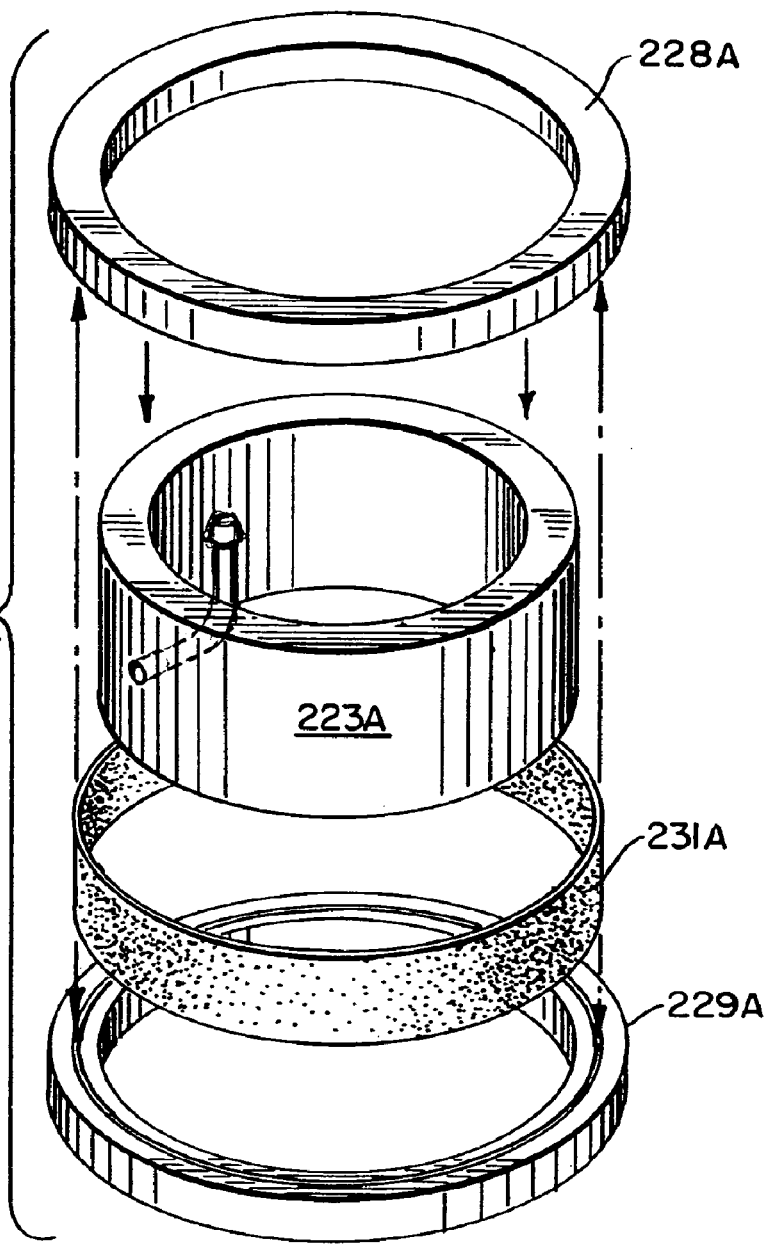
Figure 44A:
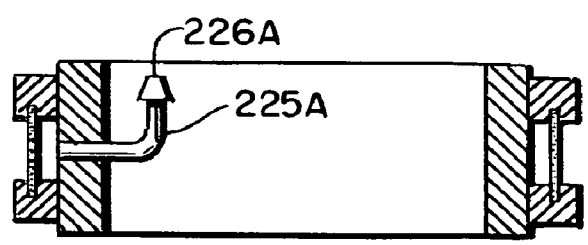
Figure 45A:
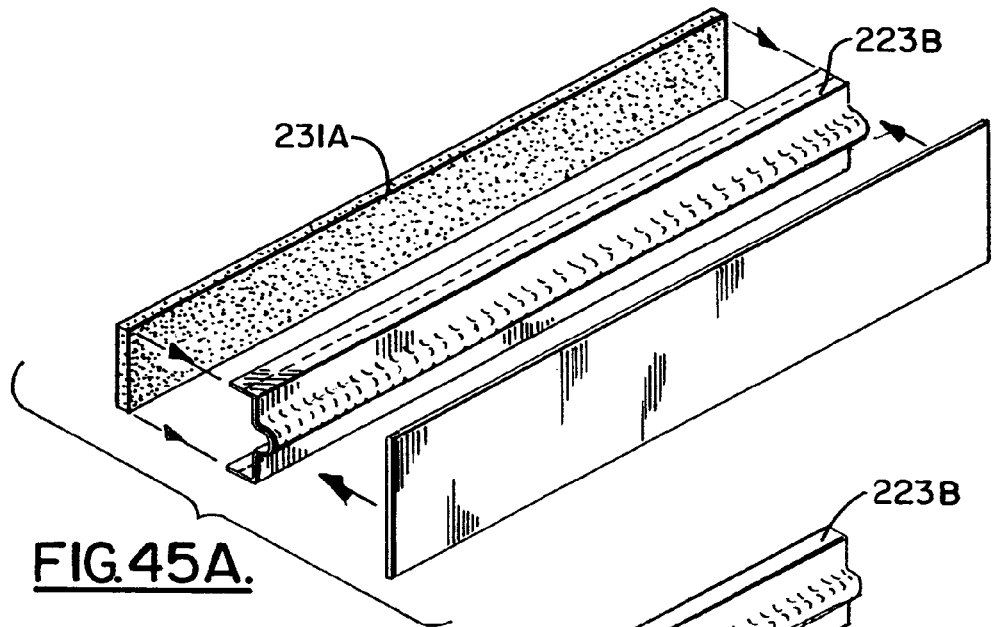
Figure 45B:
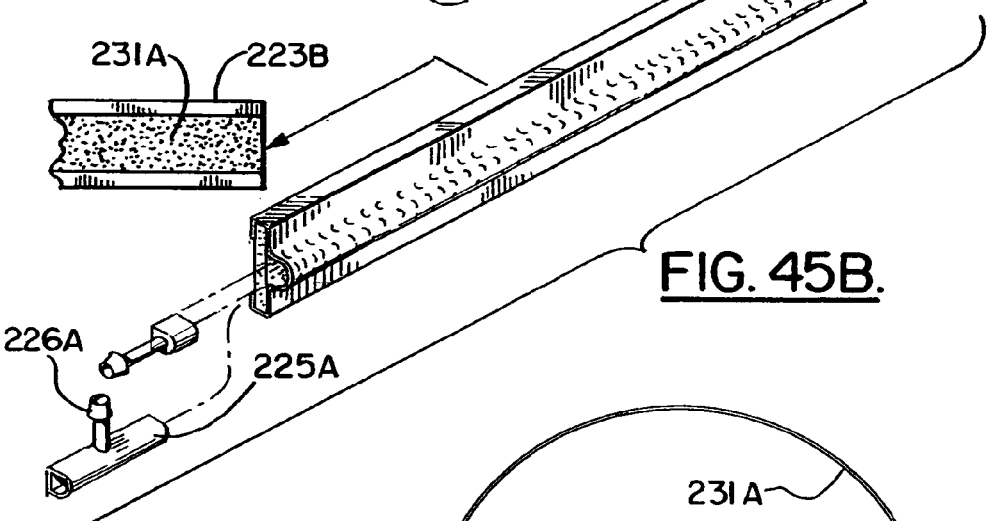
Figure 45C:
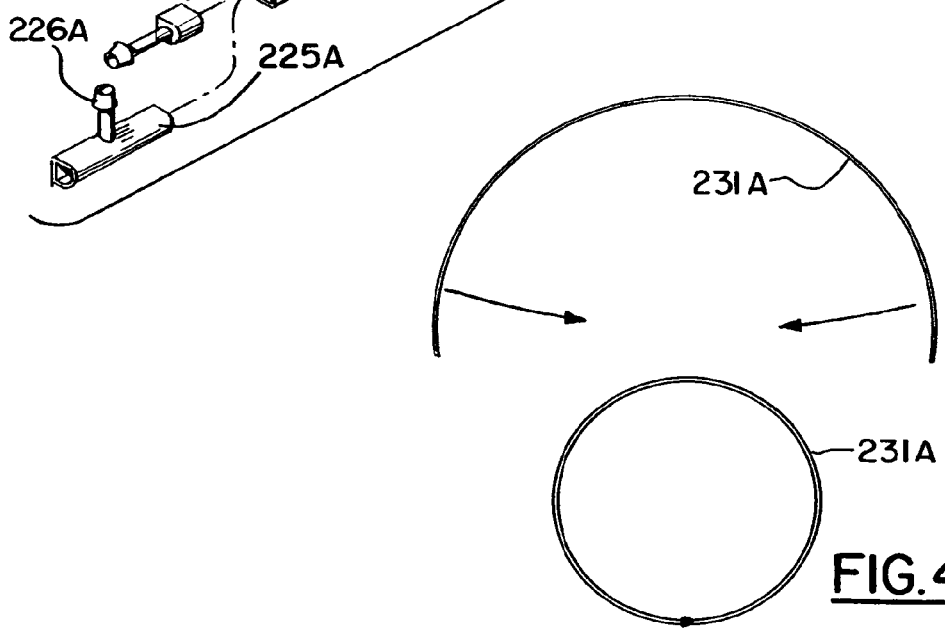

In FIGS. 43A, 44A, 45A, the diffuser shown is similar to that shown in FIGS. 43-45. The sheet 231A is a sintered metal sheet (e.g. sintered titanium) that is ozone resistant. Body 223B provides blow channel 224A. Fitting 225A transmits ozone to channel 224A via inlet 226A. Upper and lower rings 228A, 229A hold sheet 231A to body 223B.

Figure 46:
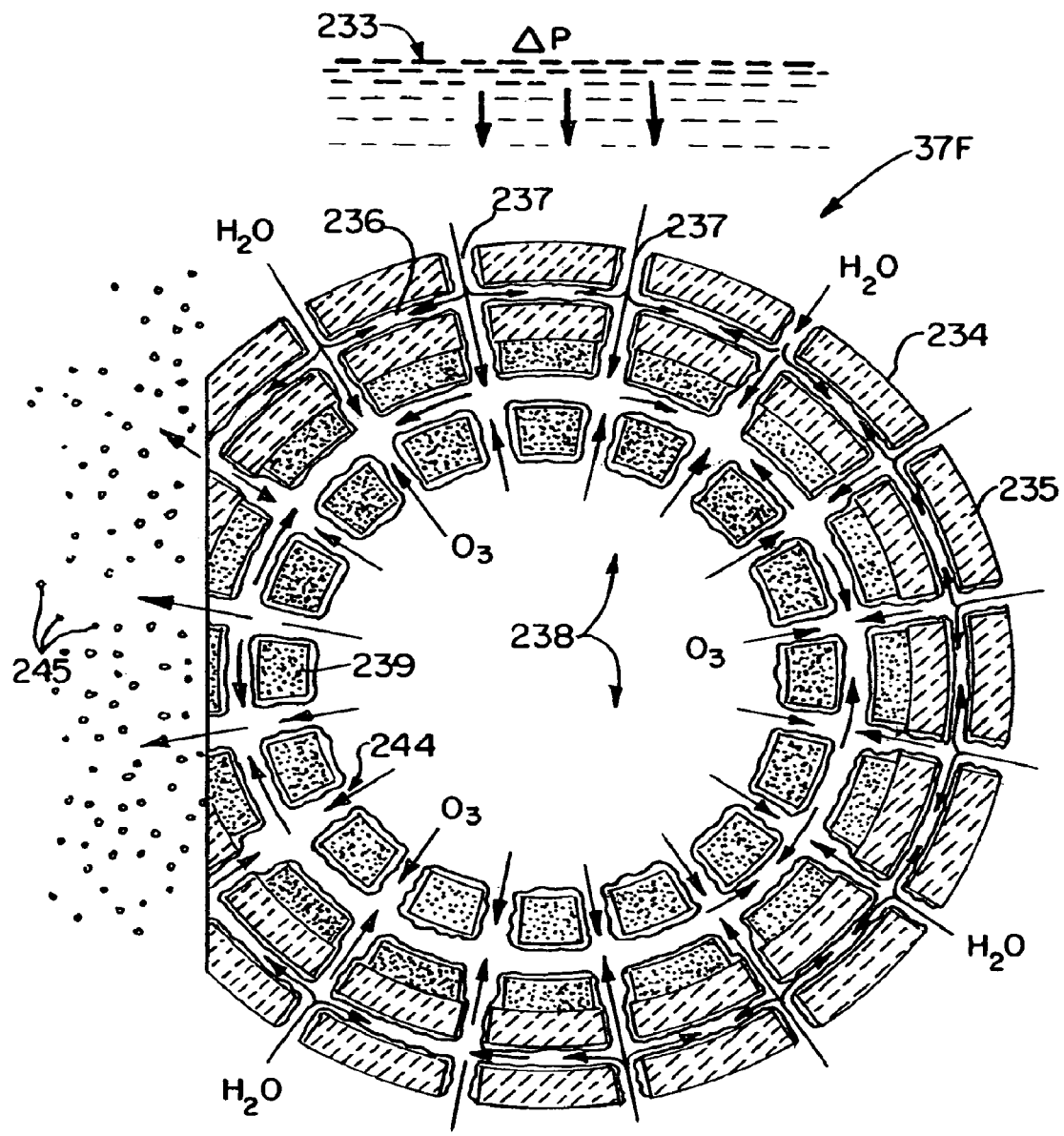
FIG. 46 is a sectional view of a sixth embodiment illustrating another diffuser construction and its operation.

In FIG. 46, another diffuser is shown, indicated by the numeral 37F. Diffuser 37F is a gas diffusion into water diffuser material configuration. The water surface 233 above diffuser 37F provides a change in pressure water column assist value. Diffuser 37F can provide a body 234 that has a low permeability material coating 235 with interconnected porisity channel 236 low permeability capillary channel 237 interconnects with circumferentially extending channel 236 as shown in FIG. 46. The pressure differential provided by the water column assist below water surface 233 and the capillary action of channels 237 wicks water back into the diffuser sensor 238. A higher permeability diffuser stone material 239 is provided next to open center 238 and is interconnected with channel 244.

Ozone is piped to the open center 238 from an ozone generator such as those described with respect to FIGS. 1-35. Ozone then travels through the channels 244 and mixes with water that is wicked via channels 236, 237, as a result of the change in pressure provided by water surface 233. The bubbles 245 that are emitted have a mixed phase gas and diffused gas water phase.

Figure 47A:
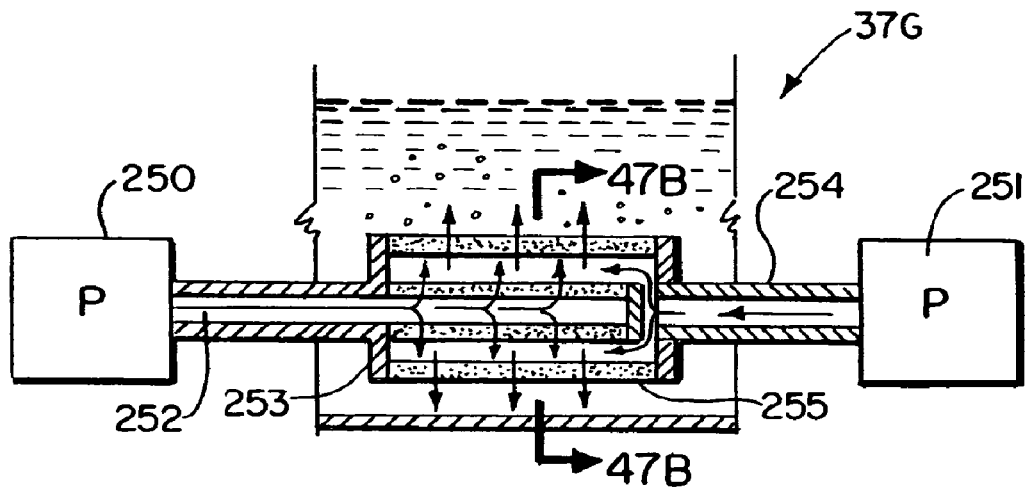
FIGS. 47A-47C are schematic views of a seventh embodiment showing another diffuser construction for use with the present invention.
Figure 47B:
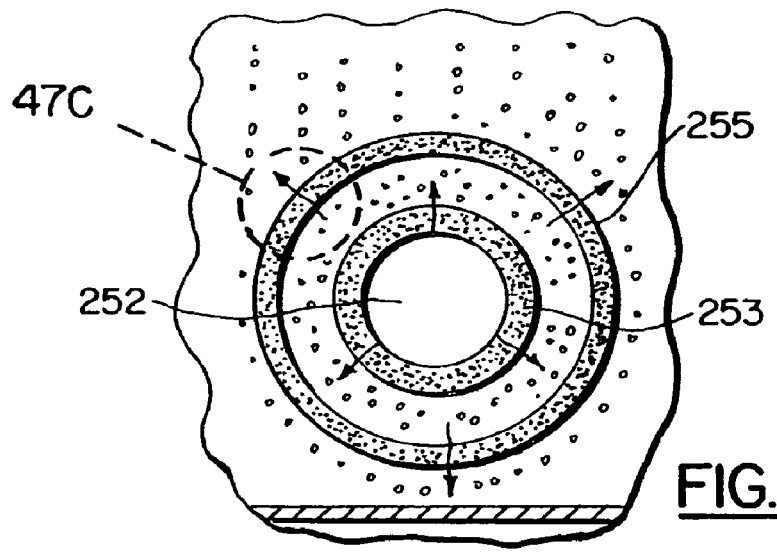
Figure 47C:
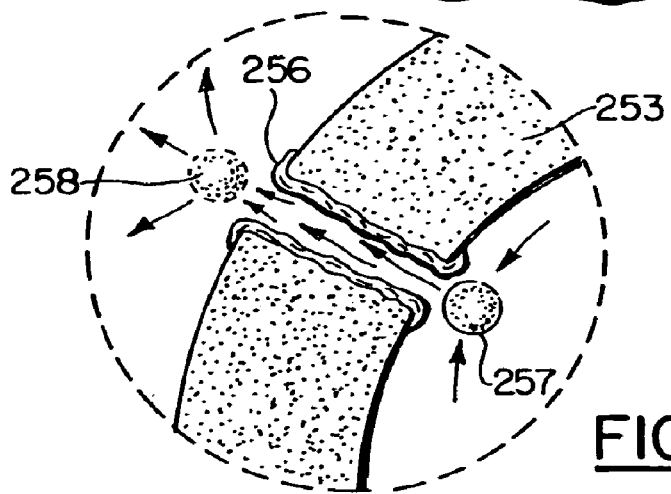

In FIGS. 47A, 47B and 47C, a diffuser is provided that is designed generally by the numeral 37G. Diffuser 37G utilizes a water supply pump 250 and a gas supply pump 251. Flow channel 252 carries pumped water to communicate with a lower permeability diffuser section 253. Pump 251 pumps ozone gas through channel 254 to a higher permeability diffuser section 255. In FIGS. 47B-47C the lower permeability diffuser section 253 is shown having a water layer 256 that lines pores of low permeability diffuser 253. In FIG. 47C, diffused gas cold water vapor droplet 257 passes through the pore of lower permeability diffuser 253 and emerges as diffused gas plus vapor at 258.

Figure 48:
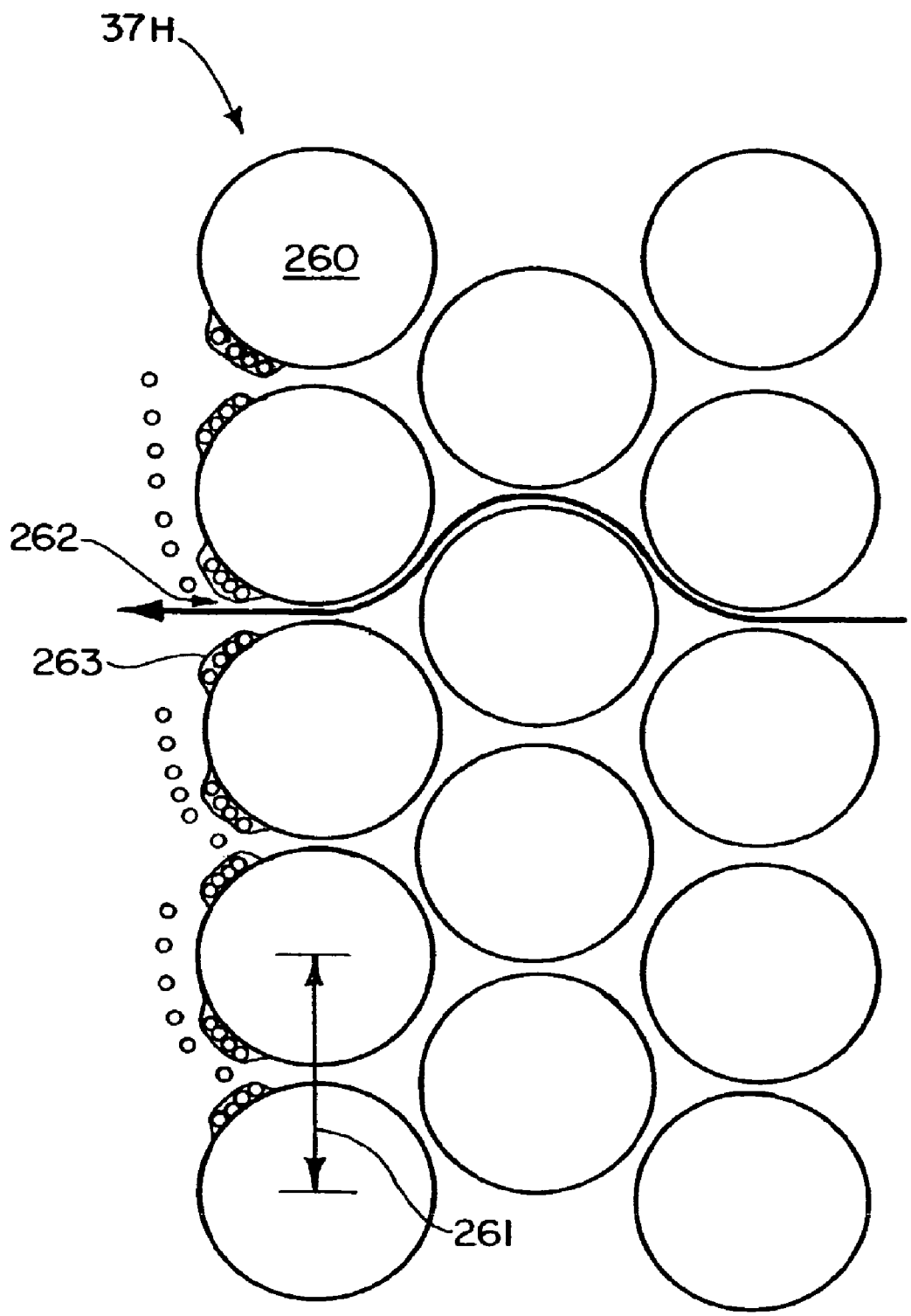
FIG. 48 is a schematic illustration of an eighth embodiment and showing another diffuser that includes a fused powder coated construction.

In FIG. 48, a diffuser 37H is shown that can be in the form of highly permeable, low initial bubble pressure, largely hydrophobic diffuser media 260. Particle spacing 261 is sufficient to allow bubbles to vent without collision or coalescence. A fused powder coating 263 of largely hydrophilic, or micro-particle material (or nano-particle material) is provided at a pore mouth or orifice 262 with bound elastic water layer membrane alteration of surface energy, hence surface permeability. This configuration generates a micro fine elastic membrane with low pressure loss through the diffuser 37H. Water is continually wicked to the pore surface, keeping it hydrated, generating a fine diameter of venturi orifice at 262.

FIGS. 49-51 show a variable flow meter with air control valve for metering low volumes of ozonated air. Control valve 270 in FIGS. 49-50 has opposed end portions with barb fittings 271, 272 so that they can be connected to plastic tubing or other slow conveying piping. Barrel 273 has a flow bore 274 that holds a ball 275 fitting 276 threadably attaches to the top of barrel 273. The stab fitting 271 on fitting 276 extends to bore 274 as shown in FIGS. 50 and 51.

Threaded sleeve 277 attaches to an enlarged lower end portion of 278 of barrel 273. An O ring 279 can be placed in between flange 280 of tube 277 and flange 281 of stab fitting 272. Valving member 282 includes a flange 283 with external thread 284 that engage the internal threads 285 sleeve 277. During use, a user can grip the narrowed knurled surface 286 of sleeve 277 and turn it to control the position of valving number 282 relative to conically shaped seat 287, thus regulating the amount of air that flows through the bore 274. Ball 275 provides an indication of flow, as barrel 273 can be clear and numbered with indicia as shown.

Figure 52:
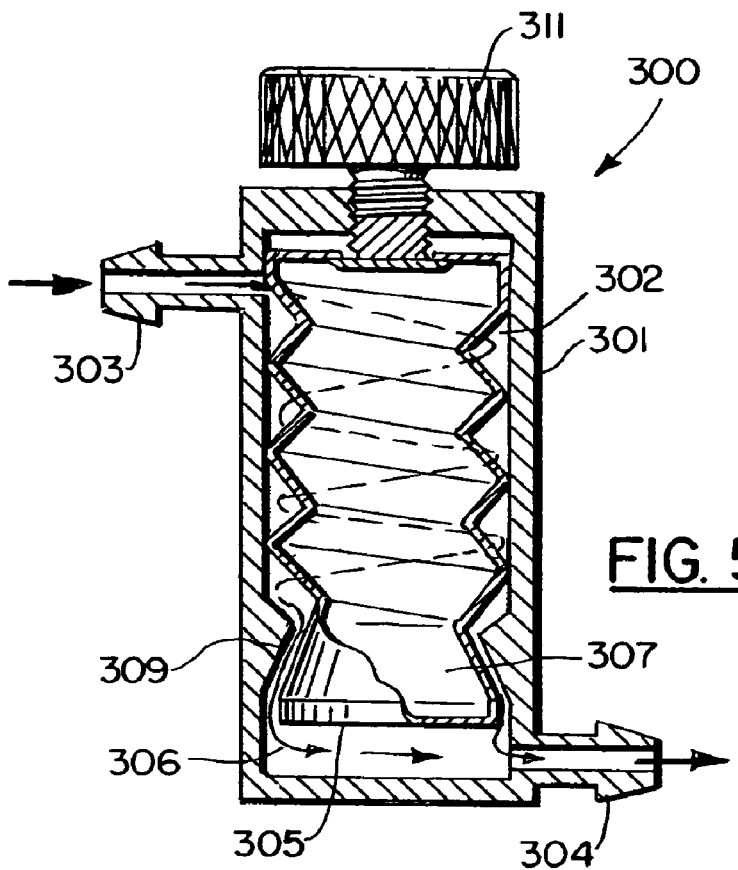
FIG. 52 is a partial sectional view of a temperature compensated, variable flow rate air control valve for use with any of the embodiments of the present invention, shown in open flow position.
Figure 53:
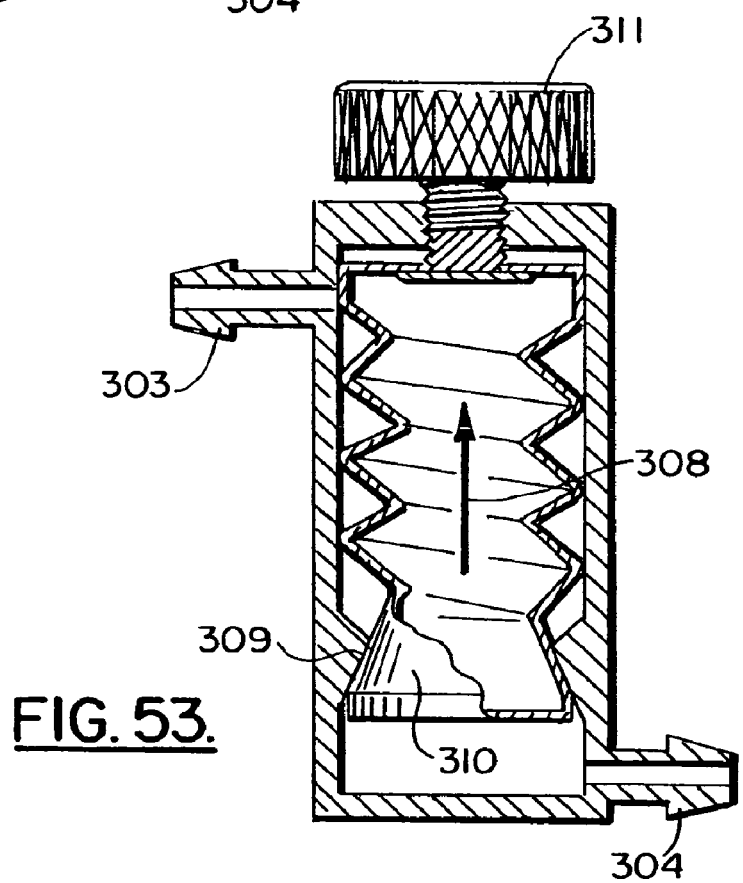
FIG. 53 is a partial, sectional view of the control valve of FIG. 52, shown in closed flow position.

In FIGS. 52 and 53, a temperature compensated variable flow rate air flow control valve 300 is shown. The control valve 300 includes a valve body 301 having an interior 302. A flow inlet 303 and a flow outlet 304 are provided as shown. A bellows 305 occupies interior 302. As ozonated air flows from inlet 303 to outlet 304, it flows circumferentially about bellows 305 as shown by arrows 306 in FIG. 52.

Bellows 305 has an interior 307 that reacts to the temperature of gas flowing from inlet 303 to outlet 304. If the flowing gas that follows the path of arrow 306 is too cold, bellows 305 retreats in the direction of arrow 308 so that valve seat 309 is closed by the conical surface 310 at the bottom of bellows 305 as shown in FIG. 53 and adjustment knob 311 can be provided for fine tuning the position of bellows 305. Bellows 305 can be a helicoil plated copper bellows that is highly sensitive to heat transfer, providing an expansion and contraction thermostat material.

Figure 54:
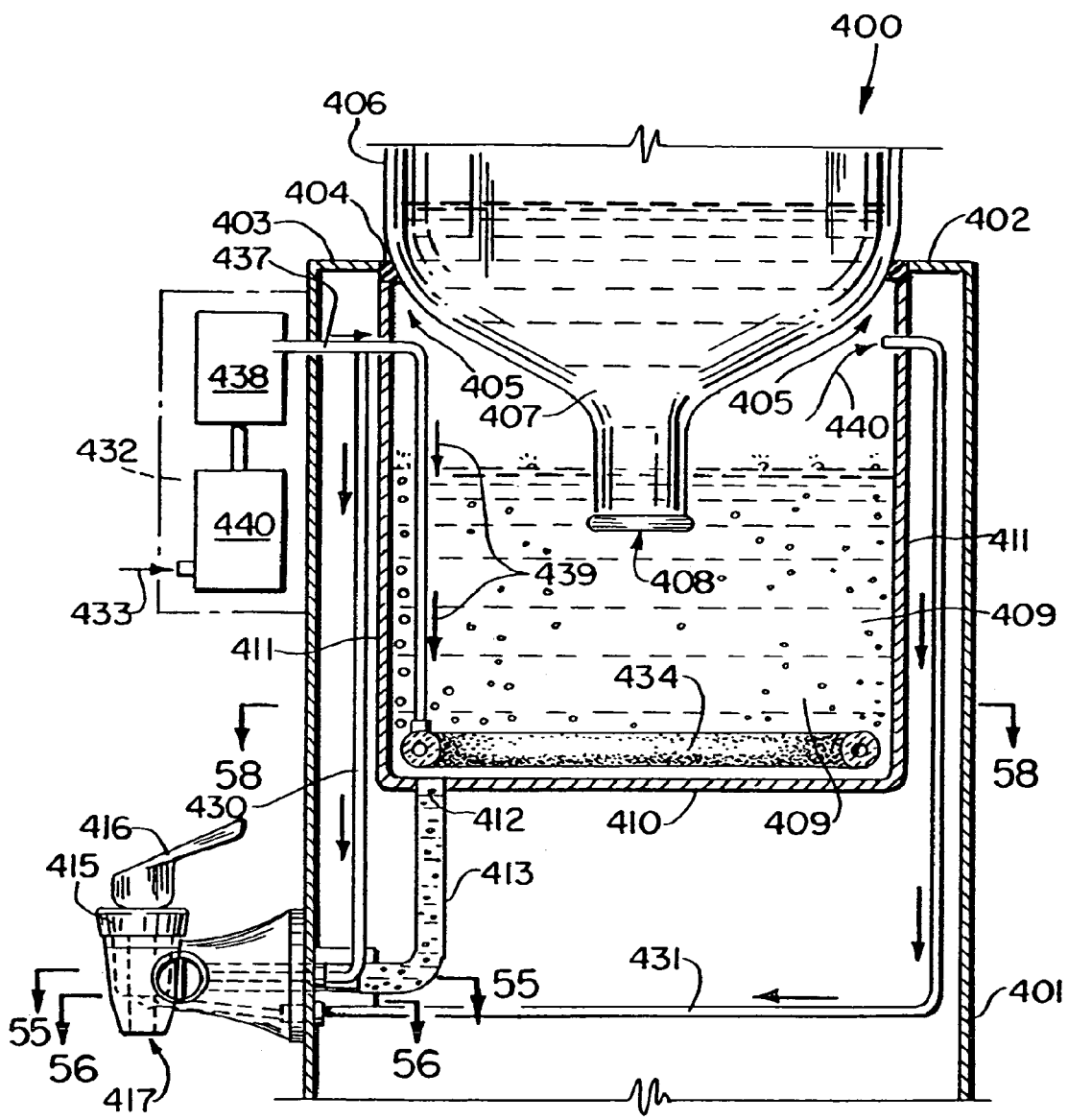
FIG. 54 is a sectional elevation view of a preferred embodiment of the apparatus of the present invention.

FIGS. 54-58 show a preferred embodiment of the apparatus of the present invention designated generally by the numeral 400 in FIG. 54. Water dispenser 400 has a cabinet 401 that can be in the form of an inverted bottle water type cabinet. However, the present invention can be used with other types of cabinets, such as for example, cabinets that contain a bottle of water at the lower end portion of the cabinet, or cabinets that connect directly to a water supply, thus eliminating the supply bottle.

Cabinet 401 has an upper cover portion 402 that includes an annular flange 403 surrounding opening 405. Gasket 404 can be used to form a seal between bottle 406 and cabinet 401.

Bottle 406 has a neck 407 and an opening 408 that communicates with reservoir 409. Reservoir 409 includes a bottom 410 that can be square or circular and side walls 411. An outlet 412 at the bottom 410 of reservoir 409 communicates with flow channel 413. Flow channel 413 has a flow bore 414 for carrying water between reservoir 409 and spigot 415.

Figure 55:
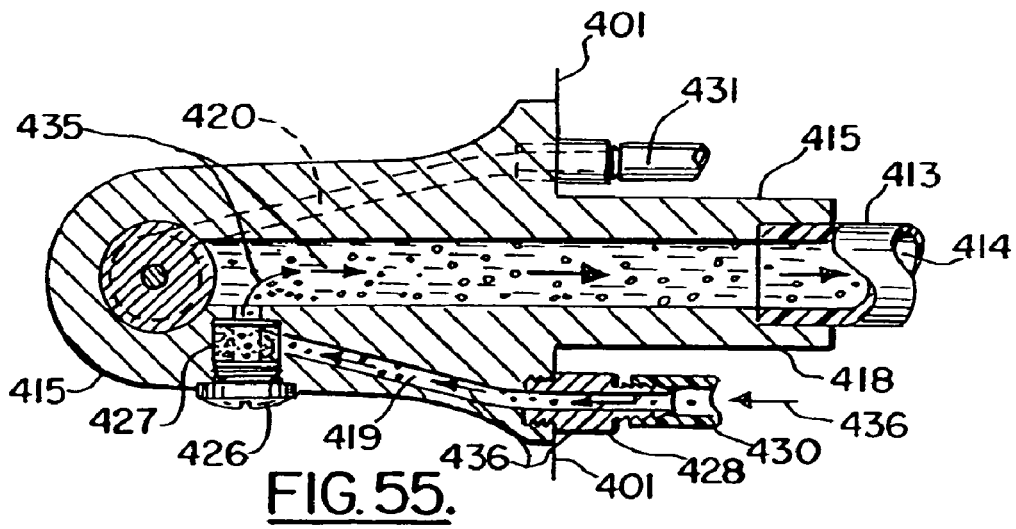
FIG. 55 is a sectional view taken along lines 55-55 of FIG. 54.
Figure 56:
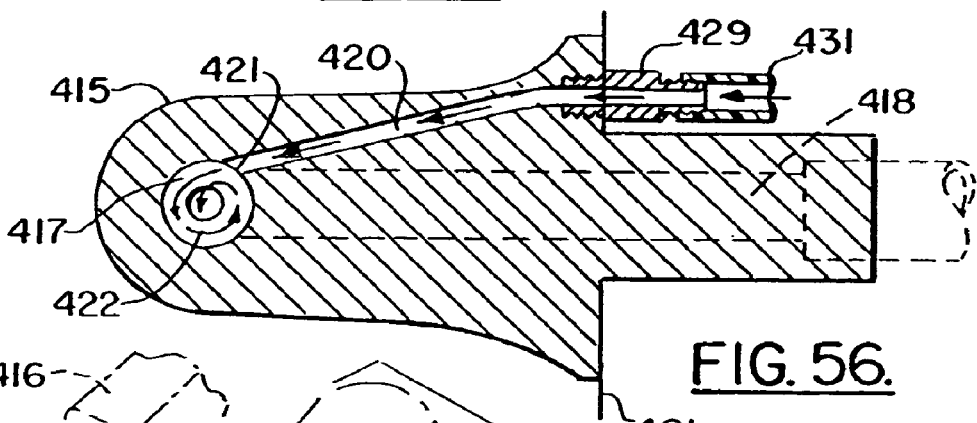
FIG. 56 is a sectional view taken along lines 56-56 of FIG. 54.
Figure 57:
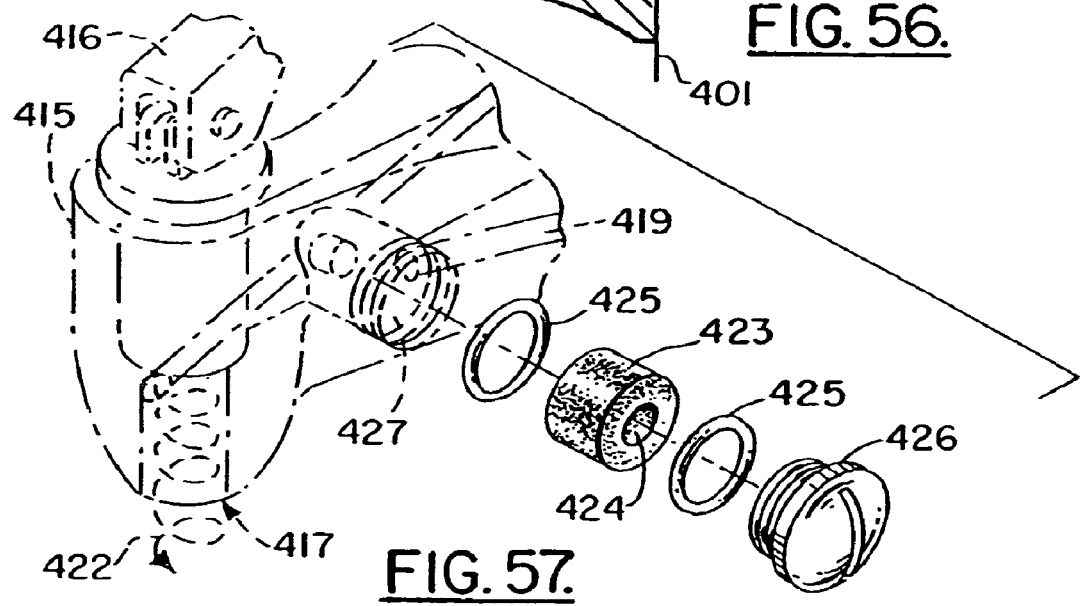
FIG. 57 is a partial perspective view of the alternate embodiment of the apparatus of the present invention.
Figure 58:
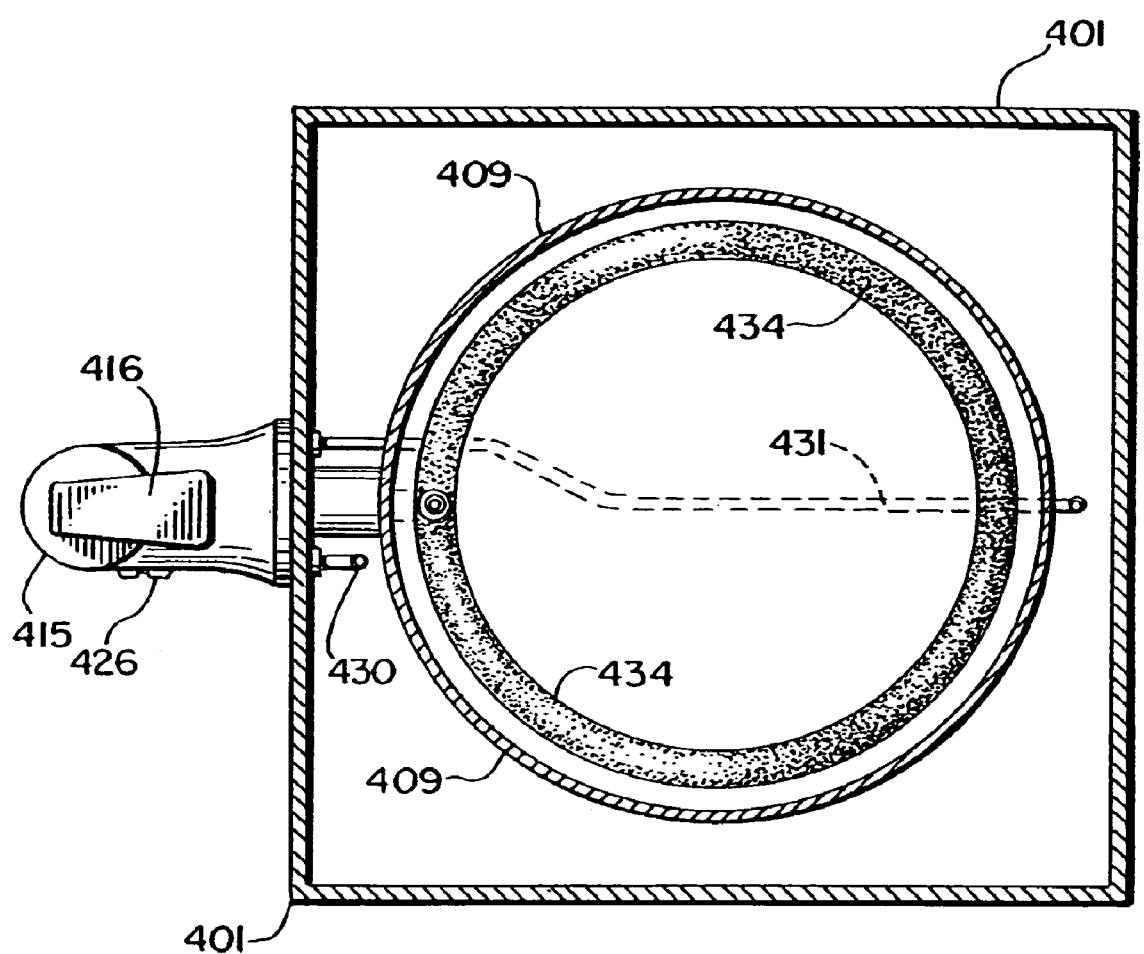
FIG. 58 is a sectional view taken along lines 58-58 of FIG. 54.

In FIGS. 55-57, spigot 415 provides a valve 416 that can be gripped and actuated by a user in order to open dispensing outlet opening 417 so that water flows via opening 417 into a selected glass, cup or like receptacle. Such a valve 416 for actuating a spigot 415 is known in the art.

Spigot flow channel 418 communicates with bore 414 of channel 413. In addition to spigot flow channel 418, there are provided on spigot 415 a pair of passages that extend through spigot 415. These passages include first passage 419 and second passage 420. The first passage 419 extends to an internally threaded opening 427. Opening 427 receives diffuser stone 423 that has an opening 424 through which air can enter opening 427 and then provide small air bubbles to spigot flow channel 418 as indicated by arrows 435 in FIG. 55.

During use, ozone is transmitted via ozone flowline 430 to fitting 428 and then to passageway 419 as indicated by the arrows 436 in FIG. 55. The ozone that flows in line 430 and in passage 419 provides small bubbles of ozone for disinfecting and sanitizing the spigot flow channel 418 and also the flow bore 414 of channel 413. Since the spigot channel 418 is near reservoir walls 411 in most or all cooling water dispensers, it will not contribute to bubbles entering the water bottle and thus dispensing water.

In FIGS. 54 and 55, the bubbles that enter spigot channel 418 can be shown flowing in the direction of arrows 435 in the horizontal section of channel 413 and then to the vertical section of channel 413 in FIG. 54 rising upwardly to outlet 412 and entering reservoir 409. Thus, the same bubbles that are used to sanitize spigot channel 418 and channel 413 also enter and assist in sanitizing reservoir 409.

Reservoir 409 is also sanitized using flowline 437 that extends from ozone generator module 432 to diffuser 434 in the direction of arrows 439 in FIG. 54. The second passage 420 receives ozone from reservoir 409. Ozone flows into ozone flowline 431 that communicates with fitting 429 and second passage 420 as shown in FIG. 17. The ozone flowing in second passage 420 communicates with spigot dispensing opening 417 at tangent position 421. This produces a spiraling flow of ozone within dispensing opening 417 as indicated schematically by the spiraling arrow 422 in FIGS. 56 and 57.

Ozone generator module 432 can be comprised of an ozone generator 438 and air blower 440. Air flow, schematically indicated by the arrow 433 can be provided using a blower for pushing the generated ozone into the flowlines 430, 431 and 437.

In FIGS. 59-62, additional constructions for the spigot and the channels that communicate with the spigot to sanitize it with ozone are shown. In FIG. 20, reservoir 441 includes a sidewall 443 and bottom 444. The reservoir 441 has a single opening 442 that receives a spigot inlet portion 455 of spigot 450. In FIGS. 20 and 21, ozone is transmitted to both the spigot 450 and the reservoir 441 via flowline 430. In FIGS. 20 and 21 flowline 430 receives flow directly from blower 440 and ozone generator 438 and flowline 431 is eliminated. Rather, ozone flows through flowline 430 to flowline 446A to diffuser 434 and to flowline 446B to diffuser 434A.

Figure 59:
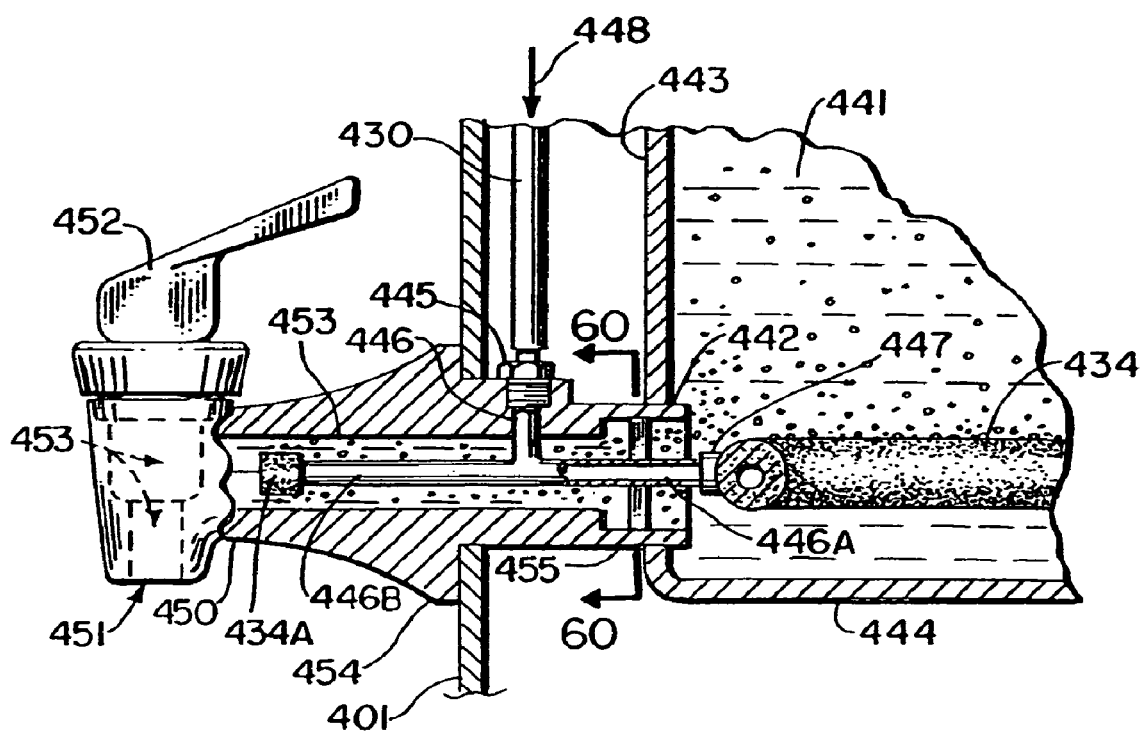
FIG. 59 is a sectional elevation view of the alternate embodiment of the apparatus of the present invention, and showing an alternate construction for the spigot.
Figure 60:
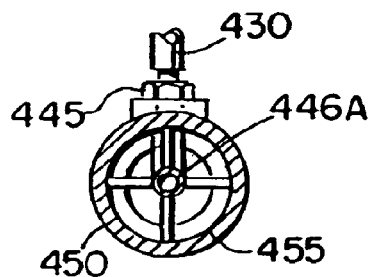
FIG. 60 is a sectional view taken along lines 60-60 of FIG. 59.

Spigot 450 includes flowline 446A,B communicating with fitting 445 as shown in FIG. 20. Flowline 446A,B includes a T-portion as shown in FIG. 59 disposed within spigot channel 453. Flowline 446A,B extends between fitting 447 and diffuser 434A. In this fashion, ozone flows from generator 438 via flowline 430 to fitting 445, to flowline 446A, to fitting 447, and then to diffuser 434. Additionally, ozone flows from generator 438 via flowline 430 to fitting 445, to flowline 446B, and then to diffuser 434A. The only opening that is formed in the walls 443, 444 of reservoir 441 is the single opening 442 that receives the spigot inlet portion 455 as shown in FIG. 59.

In order to operate the spigot 450, valve 452 is provided that opens channel 453 so that water can flow from reservoir 441 via channel 453 to outlet opening 451. Arrow 448 in FIG. 59 shows the direction of ozone flow in flowline 430 during use. Annular flange 454 of spigot 450 forms an attachment to cabinet 401, being secured in opening 442 using an interference fit, adhesive, or other suitable connection.

Figure 61:
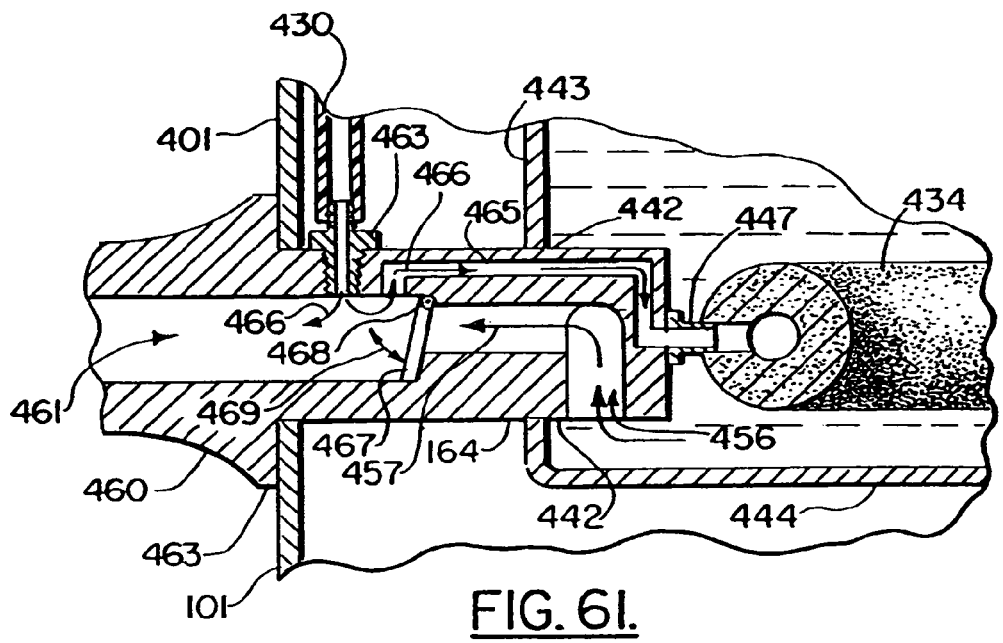
FIG. 61 is a sectional elevation view of the alternate embodiment of the apparatus of the present invention, showing another construction for the spigot.
Figure 62:
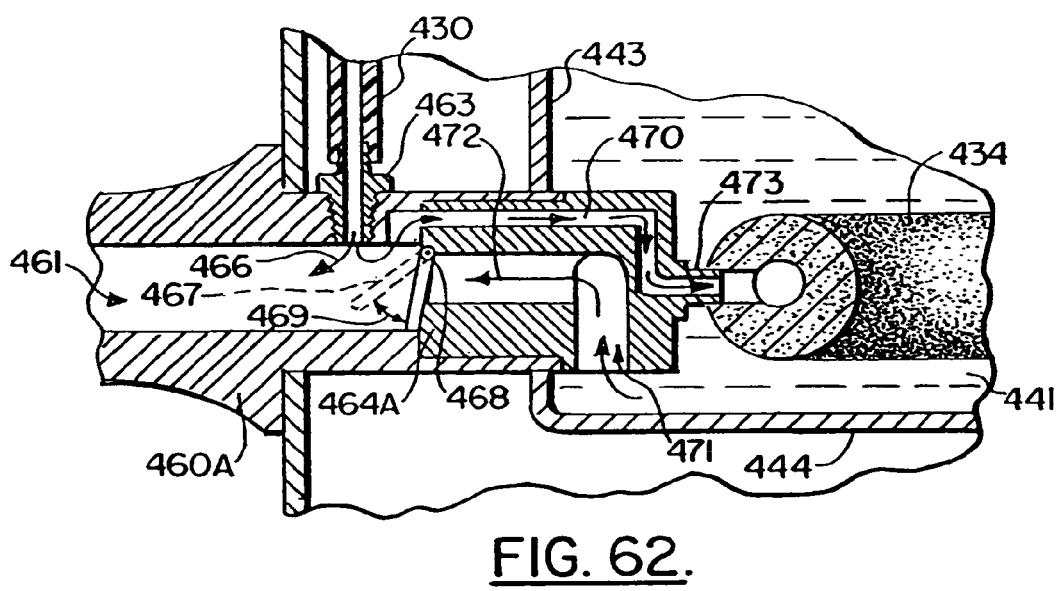
FIG. 62 is a sectional elevation view of the alternate embodiment of the apparatus of the present invention, showing another construction for the spigot.

In FIGS. 61 and 62, two additional constructions for a spigot are shown, designated as spigot 460 in FIG. 61 and spigot 460A in FIG. 62. Spigot 460 in FIG. 22 has a spigot channel 461, annular flange 462 and a spigot inlet portion 464. The spigot 460 also provides an ozone channel 465 that communicates with spigot channel 461. Valving member 467 prevents the flow of ozone from flowline 430 to directly to water inlet opening 456. Rather, when ozone is being dispensed into channel 461, back pressure causes valving member 467 to close. The valving member 467 is pivotally attached to spigot 460 at pivot 468.

The valving member 467 is normally closed due to gravity and backpressure and opens when water is being dispensed as when valve 452 is opened. Valving member 467 can be partially open due to buoyancy. However, it will close after ozone begins to flow as shown by arrows 466. The spigot 460 provides the same dispensing portion that includes a valving member 452 and a valve outlet 451 as shown in FIG. 59. Those portions have been removed from FIG. 61 for purposes of clarity.

In FIG. 61, arrow 466 shows the flow of ozone from flowline 430 through fitting 463 to ozone channel 465. The ozone flowing in channel 465 reaches fitting 447 that is connected to diffuser 434. Ozone flows from flowline 430 to diffuser 434 and without the necessity of a second opening in reservoir wall 443. Arrow 469 schematically illustrates the opening and closing of valving member 467.

In FIG. 62, another spigot 460A is shown. The spigot 468 is a construction that can be used to modify an existing spigot because the spigot inlet portion 464A is a "retrofit" part. In FIG. 62, the existing spigot on a cooler/dispenser is milled to receive the retrofit spigot inlet portion 464A. The spigot inlet portion 464A provides water inlet opening 471 and ozone channel 470. The ozone channel 470 communicates with a fitting 473 that can be integrally formed with the spigot inlet portion 464A. Arrow 472 in FIG. 62 shows the path of water being dispensed when the valve 452 is opened and water flows from reservoir 441 to water inlet opening 471 and to spigot channel 461. When water is not being dispensed and ozone is to be transmitted via flowline 430, the valving member 467 closes because of gravity and back pressure. Ozone enters the channel 461 and also the ozone channel 470.

The following table lists the parts numbers and parts descriptions as used herein and in the drawings attached hereto.

| PARTS LIST | |
|---|---|
| Part Number | Description |
| 10 | water dispenser |
| 10A | water dispenser |
| 10B | water dispenser |
| 10C | water dispenser |
| 11 | cabinet |
| 12 | lower end |
| 13 | upper end |
| 14 | cover |
| 15 | annular flange |
| 16 | gasket |
| 17 | opening |
| 18 | bottle |
| 19 | bottle neck |
| 20 | reservoir |
| 21 | interior |
| 22 | reservoir side wall |
| 23 | reservoir bottom wall |
| 24 | open top |
| 25 | water surface |
| 26 | spigot |
| 27 | spigot |
| 28 | refrigeration coil |
| 29 | compressor |
| 30 | flow line |
| 31 | flow line |
| 32 | heat exchanger |
| 33 | electrical line |
| 34 | plug |
| 35 | flow line |
| 36 | outlet port |
| 37 | diffuser |
| 37A | diffuser |
| 37B | diffuser |
| 37C | diffuser |
| 37D | diffuser |
| 37E | diffuser |
| 37F | diffuser |
| 38 | air line |
| 39 | fitting |
| 40 | housing |
| 41 | electrical line |
| 42 | controller |
| 43 | plug |
| 44 | receptacle |
| 45 | flange |
| 46 | opening |
| 47 | lower end |
| 48 | upper end |
| 49 | opening |
| 50 | ozone generator |
| 51 | transformer |
| 52 | electrical line |
| 53 | motor |
| 54 | blower |
| 55 | air line |
| 56 | air inlet |
| 57 | ozone generator housing |
| 58 | lower housing section |
| 59 | upper housing section |
| 60 | flange |
| 61 | flange |
| 62 | gasket |
| 63 | bolted connection |
| 64 | internally threaded opening |
| 65 | arrow |
| 66 | arrow |
| 67 | bubble |
| 68 | foot |
| 69 | opening |
| 70 | angle |
| 71 | filter |
| 72 | porous body |
| 73 | inner surface |
| 74 | outer surface |
| 75 | hollow bore |
| 76 | non-porous coating |

PARTS LIST

| Part Number | Description |
|---|---|
| 77 | end portion |
| 78 | end portion |
| 79 | elbow fitting |
| 80 | body |
| 81 | leg |
| 82 | leg |
| 83 | coupling material |
| 84 | bore |
| 85 | bore |
| 86 | external threads |
| 87 | stab fitting |
| 88 | grinding tool |
| 89 | shaft |
| 90 | exposed face |
| 91 | arrow |
| 92 | bubble |
| 100 | spigot |
| 100A | spigot |
| 100B | spigot |
| 100C | spigot |
| 100D | spigot |
| 100E | spigot |
| 100F | spigot |
| 101 | spigot housing |
| 102 | handle |
| 103 | annular flange |
| 104 | threads |
| 105 | horizontal bore |
| 106 | vertical bore |
| 107 | flow outlet |
| 108 | valve body |
| 109 | annular shoulder |
| 110 | operating rod socket |
| 111 | operating rod |
| 112 | return spring |
| 113 | socket |
| 114 | cap |
| 115 | internal threads |
| 116 | external threads |
| 117 | retainer |
| 118 | annular flange |
| 119 | annular flange |
| 120 | annular groove |
| 121 | transverse opening |
| 122 | transverse opening |
| 123 | pin |
| 124 | cam surface |
| 125 | collar |
| 126 | central opening |
| 127 | dual contact barrel |
| 128 | receptacle |
| 129 | plug |
| 130 | electrical line |
| 131 | electrical line |
| 132 | waterproof seal |
| 133 | ozone supply fitting |
| 134 | diffuser |
| 135 | barb connector |
| 136 | flow tube |
| 137 | flow bore |
| 138 | electrical lead |
| 139 | electrical lead |
| 140 | passageway |
| 141 | user |
| 142 | arrow |
| 143 | spigot body |
| 144 | valve handle |
| 145 | flow sensor |
| 146 | instrumentation line |
| 147 | magnetic flow sensor |
| 148 | electrical line |
| 149 | electrical line |
| 150 | ozone discharge tube |
| 151 | dielectric tubing |
| 152 | longitudinal bore |
| 153 | foil adhesive tape section |
| 154 | release liner |
| 155 | foil adhesive tape section |
| 156 | release liner |
| 157 | arrow |
| 158 | electrode |
| 159 | spring clip |
| 160 | conduit |
| 161 | conduit |
| 162 | safety cover |
| 163 | circuit board |
| 164 | clamp |
| 165 | exposed part |
| 166 | outer surface |
| 167 | lead |
| 168 | lead |
| 169 | blower |
| 170 | flow sensor |
| 171 | electromagnet |
| 172 | flow sensor |
| 173 | electrical supply line |
| 174 | instrumentation line |
| 175 | instrumentation line |
| 176 | extension tube |
| 177 | flow bore |
| 178 | extension tube |
| 179 | flow bore |
| 180 | extension tube |
| 181 | flow bore |
| 182 | nut |
| 183 | external threads |
| 184 | extension tube |
| 185 | timer |
| 186 | pump |
| 187 | float valve controller |
| 188 | float |
| 189 | water level |
| 190 | water level |
| 191 | air pressure controller |
| 192 | fluid pressure controller |
| 193 | contact |
| 194 | electrical line |
| 195 | arrow |
| 196 | electrical line |
| 197 | instrumentation line |
| 198 | instrumentation line |
| 200 | silicone tube |
| 201 | bore |
| 202 | fitting |
| 203 | connector |
| 204 | wall |
| 205 | opening |
| 206 | diffuser insert |
| 207 | tube |
| 208 | wall |
| 209 | Socket |
| 210 | top section |
| 211 | bottom section |
| 212 | bore |
| 213 | module |
| 214 | stab fitting |
| 215 | fitting |
| 216 | inlet |
| 217 | blade |
| 218 | tube |
| 219 | wall |
| 220 | bore |
| 221 | slot |
| 222 | connector |
| 223 | annular body |
| 223A | body |
| 223B | body |
| 224 | annular channel |
| 224A | flow channel |
| 225 | inlet fitting |
| 225A | fitting |
| 226 | arrow |

PARTS LIST

| Part Number | Description |
|---|---|
| 226A | inlet |
| 227 | arrow |
| 228 | upper retainer |
| 228A | upper ring |
| 229 | lower retainer |
| 229A | lower ring |
| 230 | opening |
| 231 | annular sheet |
| 231A | sintered metal sheet |
| 232 | slotted opening |
| 233 | water surface |
| 234 | body |
| 235 | coating |
| 236 | channel |
| 237 | channel |
| 238 | center |
| 239 | diffuser material |
| 240 | interlocking annular section |
| 241 | interlocking annular section |
| 242 | interlocking annular section |
| 243 | interlocking annular section |
| 244 | channel |
| 245 | bubbles |
| 250 | pump |
| 251 | pump |
| 252 | channel |
| 253 | diffuser section |
| 254 | channel |
| 255 | diffuser section |
| 256 | lining |
| 257 | droplet |
| 258 | gas and vapor mixture |
| 260 | media |
| 261 | bubble spacing |
| 262 | orifice |
| 263 | coating |
| 270 | control valve |
| 271 | fitting |
| 272 | fitting |
| 273 | barrel |
| 274 | bore |
| 275 | ball |
| 276 | fitting |
| 277 | enlarged lower end |
| 278 | lower end |
| 279 | O-ring |
| 280 | flange |
| 281 | flange |
| 282 | valve member |
| 283 | flange |
| 284 | threads |
| 285 | internal threads |
| 286 | Knurled surface |
| 287 | valve seat |
| 300 | valve |
| 301 | body |
| 302 | interior |
| 303 | flow inlet |
| 304 | outlet |
| 305 | bellows |
| 306 | arrow |
| 307 | interior |
| 308 | arrow |
| 309 | valve seat |
| 310 | conical surface |
| 311 | knob |
| 400 | water dispenser |
| 401 | cabinet |
| 402 | cover |
| 403 | annular flange |
| 404 | gasket |
| 405 | opening |
| 406 | bottle |
| 407 | neck |
| 408 | opening |
| 409 | reservoir |
| 410 | bottom |
| 411 | wall |
| 412 | outlet |
| 413 | channel |
| 414 | flow bore |
| 415 | spigot |
| 416 | valve |
| 417 | dispensing opening |
| 418 | spigot flow channel |
| 419 | first passage |
| 420 | second passage |
| 421 | tangent position |
| 422 | spiral arrow |
| 423 | diffuser |
| 424 | opening |
| 425 | O-ring |
| 426 | closure cap |
| 427 | internally threaded opening |
| 428 | fitting |
| 429 | fitting |
| 430 | ozone flowline |
| 431 | ozone flowline |
| 432 | ozone generator module |
| 438 | ozone generator |
| 439 | arrow |
| 440 | blower |
| 441 | reservoir |
| 442 | opening |
| 443 | wall |
| 444 | bottom |
| 445 | fitting |
| 446 | flowline |
| 446A | flowline portion |
| 446B | flowline portion |
| 447 | fitting |
| 448 | arrow |
| 450 | spigot |
| 451 | outlet |
| 452 | valve |
| 453 | spigot channel |
| 454 | annular flange |
| 455 | spigot inlet portion |
| 456 | water inlet opening |
| 457 | arrow |
| 460 | spigot |
| 460A | spigot |
| 461 | channel |
| 462 | annular flange |
| 463 | fitting |
| 464 | spigot inlet portion |
| 464A | spigot inlet portion |
| 465 | ozone channel |
| 466 | arrow |
| 467 | valving member |
| 468 | pivot |
| 469 | arrow |
| 470 | ozone channel |
| 471 | water inlet opening |
| 472 | arrow |
| 473 | fitting |

The foregoing embodiments are presented by way of example only; the scope of the present invention is to be limited only by the following claims.

The invention claimed is:

1. A method of sanitizing water dispenser having a cabinet with water supply that includes a reservoir, and an operable spigot on the cabinet enables water to be dispensed from the cabinet and its water supply comprising the steps of:
 a) generating ozone with an ozone generator;
 b) collecting the generated ozone inside of an ozone generator housing;

c) transmitting ozone from the ozone generator housing to the water supply reservoir so that bubbles rise upwardly in the reservoir; and d) wherein in step "c" the ozone enters the reservoir via a plurality of diffuser elements that are mounted in the wall of a polymeric tube that has a tube wall surrounding a tube lumen.

2. The method of claim 1 further comprising the step of spacing the diffuser element from the center of the reservoir so that ozone from the diffuser scrubs the reservoir wall.

3. The method of claim 1 wherein bubbles rise upwardly in the reservoir a distance of between about two and ten inches.

4. The method of claim 1 wherein bubbles rise upwardly a distance of between about four and eight inches.

5. The method of claim 1 wherein the ozone generated in step "b" is spike ozonation that is generated for a duration of between about one and five minutes.

6. The method of claim 1 wherein the ozone generated in step "b" is spike ozonation that is generated for a duration of between about two and three minutes.

7. The method of claim 4 wherein the ozone generated in step "b" is spike ozonation that is generated for a duration of between about one and three minutes.

8. The method of claim 1 wherein a plurality of the diffuser elements are of sintered metal and further comprising the step of controlling bubble size with the porosity of the sintered metal.

9. The method of claim 8 wherein the sintered metal is an ozone resistant titanium metal.

10. The method of claim 1 wherein a plurality of the diffuser elements are of porous ceramic material and further comprising the step of controlling bubble size with the porosity of the ceramic.

11. The method of claim 10 wherein the ceramic material is an insoluble dry ceramic material.

12. The method of claim 1 wherein a plurality of the diffuser elements are of a flanged button shape.

13. The method of claim 1 wherein a plurality of the diffuser elements are of a conical button shape.

14. A method of sanitizing water dispenser having a cabinet with water supply that includes a reservoir, and an operable spigot on the cabinet enables water to be dispensed from the cabinet and its water supply comprising the steps of:

a) generating ozone with an ozone generator;

b) collecting the generated ozone inside of an ozone generator housing;

c) transmitting ozone from the ozone generator housing to the water supply reservoir so that bubbles rise upwardly in the reservoir; and d) wherein in step "c" the ozone enters the reservoir via a plurality of diffuser elements that are mounted in the wall of a polymeric tube that has a tube wall surrounding a tube lumen.

15. The method of claim 14 further comprising the step of spacing the diffuser element from the center of the reservoir so that ozone from the diffuser scrubs the reservoir.

16. The method of claim 14 wherein bubbles rise upwardly in the reservoir a distance of between about two and ten inches.

17. The method of claim 14 wherein bubbles rise upwardly a distance of between about four and eight inches.

18. The method of claim 14 wherein the ozone generated in step "b" is spike ozonation that is generated for a duration of between about one and five minutes.

19. The method of claim 14 wherein the ozone generated in step "b" is spike ozonation that is generated for a duration of between about two and three minutes.

20. The method of claim 14 wherein the ozone generated in step "b" is spike ozonation that is generated for a duration of between about one and three minutes.

21. The method of claim 14 wherein a plurality of the diffuser elements are of sintered metal and further comprising the step of controlling bubble size with the porosity of the sintered metal.

22. The method of claim 14 wherein a plurality of the diffuser elements are of porous ceramic material and further comprising the step of controlling bubble size with the porosity of the ceramic.

23. The method of claim 14 wherein the sintered metal is an ozone resistant titanium metal.

24. The method of claim 14 wherein the ceramic material is an insoluble dry ceramic.

25. The method of claim 14 wherein a plurality of the diffuser elements are of a flanged button shape.

26. The method of claim 14 wherein a plurality of the diffuser elements are of a conical button shape.

* * * * *